United States Patent
Bair et al.

(10) Patent No.: US 9,676,721 B2
(45) Date of Patent: Jun. 13, 2017

(54) COMPOUNDS AND COMPOSITIONS FOR THE INHIBITION OF NAMPT

(75) Inventors: Kenneth W. Bair, Watertown, MA (US); Alexandre J. Buckmelter, Watertown, MA (US); Bingsong Han, Watertown, MA (US); Jian Lin, Watertown, MA (US); Dominic J. Reynolds, Watertown, MA (US); Chase C. Smith, Watertown, MA (US); Zhongguo Wang, Watertown, MA (US); Xiaozhang Zheng, Watertown, MA (US)

(73) Assignee: FORMA TM, LLC, Watertown, MA (US)

( * ) Notice: Subject to any disclaimer, the term of this patent is extended or adjusted under 35 U.S.C. 154(b) by 688 days.

(21) Appl. No.: 13/820,489

(22) PCT Filed: Sep. 2, 2011

(86) PCT No.: PCT/US2011/050323
§ 371 (c)(1),
(2), (4) Date: Jul. 22, 2013

(87) PCT Pub. No.: WO2012/031199
PCT Pub. Date: Mar. 8, 2012

(65) Prior Publication Data
US 2013/0295051 A1 Nov. 7, 2013

Related U.S. Application Data

(60) Provisional application No. 61/379,800, filed on Sep. 3, 2010, provisional application No. 61/386,033, filed on Sep. 24, 2010, provisional application No. 61/476,590, filed on Apr. 18, 2011.

(51) Int. Cl.

| | | |
|---|---|---|
| *C07D 213/75* | (2006.01) | |
| *C07D 213/74* | (2006.01) | |
| *C07D 471/04* | (2006.01) | |
| *A61K 31/4406* | (2006.01) | |
| *A61K 31/4409* | (2006.01) | |
| *C07D 401/04* | (2006.01) | |
| *A61K 31/437* | (2006.01) | |
| *A61K 45/06* | (2006.01) | |

(52) U.S. Cl.
CPC .......... *C07D 213/75* (2013.01); *A61K 31/437* (2013.01); *A61K 31/4406* (2013.01); *A61K 31/4409* (2013.01); *A61K 45/06* (2013.01); *C07D 213/74* (2013.01); *C07D 401/04* (2013.01); *C07D 471/04* (2013.01)

(58) Field of Classification Search
None
See application file for complete search history.

(56) References Cited

U.S. PATENT DOCUMENTS

| | | |
|---|---|---|
| 4,895,840 A | 1/1990 | Shanklin, Jr. |
| 5,696,140 A | 12/1997 | Bramm et al. |
| 6,255,323 B1 | 7/2001 | Huang et al. |
| 6,525,077 B2 | 2/2003 | Binderup et al. |
| 6,642,215 B2 | 11/2003 | Madsen et al. |
| 7,253,193 B2 | 8/2007 | Binderup et al. |
| 2009/0162454 A1 | 6/2009 | Roulston et al. |

FOREIGN PATENT DOCUMENTS

| | | |
|---|---|---|
| CN | 1854135 A | 11/2006 |
| EP | 0747374 A1 | 11/1996 |
| WO | 9854143 A1 | 5/1998 |
| WO | 9854144 A1 | 12/1998 |
| WO | 9854145 A1 | 12/1998 |
| WO | 00/61559 A1 | 10/2000 |
| WO | 00/61561 A1 | 10/2000 |
| WO | 0061561 A1 | 10/2000 |
| WO | 0172960 A2 | 10/2001 |
| WO | 0242265 A2 | 5/2002 |
| WO | 02094265 A1 | 11/2002 |
| WO | 02094322 A2 | 11/2002 |
| WO | 03088908 A2 | 10/2003 |
| WO | WO 2005/075436 A2 * | 8/2005 |
| WO | 2005113534 A2 | 12/2005 |

(Continued)

OTHER PUBLICATIONS

Side Reactions in Organic Synthesis, Dorwald, F. A., 2005, Wiley: VCH, Weinheim, p. IX.*
Patent Examination Report No. 1 for Australian Patent Application No. 2011295727, mailed on Feb. 4, 2014.
Communication pursuant to Article 94(3) EPC for Application No. 11 757 484.4-1451, mailed on Jan. 24, 2014.
Pernille-Julia Vig Hjarnaa, et al., CHS 828, a Novel Pyridyl Cyanoguanidine with Potent Antitumor Activity in Vitro and in Vivo., Cancer Research, Nov. 15, 1999, pp. 5751-5757, vol. 50, Leo Pharmaceutical Products, Denmark and Division of Clinical Pharmacology, University Hospital, Uppsala University, Uppsala, Sweden.

(Continued)

*Primary Examiner* — Savitha Rao
*Assistant Examiner* — Gregg Polansky
(74) *Attorney, Agent, or Firm* — Gearhart Law LLC

(57) ABSTRACT

The present invention relates to compounds and compositions for the inhibition of NAMPT, their synthesis, applications and antidotes. An illustrative compound of the invention is shown below.

(I)

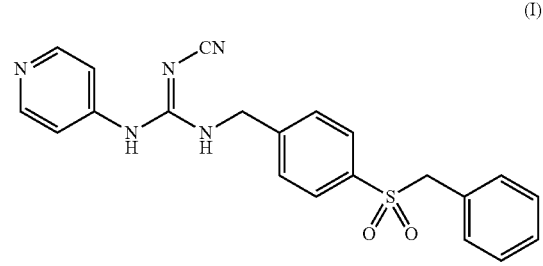

7 Claims, No Drawings

(56) References Cited

FOREIGN PATENT DOCUMENTS

| WO | 2006066584 A1 | 6/2006 |
|---|---|---|
| WO | 2009072004 A1 | 6/2009 |
| WO | 2009086835 A1 | 7/2009 |
| WO | 2010142735 A1 | 12/2010 |

OTHER PUBLICATIONS

L. B. Hougha, et al., Antinociceptive Activity of Furan-Containing Congeners of Improgan and Ranitidine, NIH Public Access Author Manuscript Bioorg Med Chem Lett. Author Manuscript, Oct. 15, 2008, pp. 1-9.

Yujia Dai et al., Thienopyrimidine Ureas as Novel and Potent Multitargeted Receptor Tyrosine Kinase Inhibitors, J. Med. Chem, Aug. 26, 2005, pp. 6066-6083, 48 (19), American Chemical Society Publications, Only Abstract provided.

Lovborg et al., Structure-activity relationship analysis of cytotoxic cyanoguanidines: selection of CHS 828 as candidate drug, BMC Research Notes, Jun. 29, 2009, pp. 1-7, http://www.biomedcentral.com/1756-0500/2/114, BioMed Central Ltd.

English Translation of First Office Action for Chinese Patent Application No. 201180053283.0, dated May 28, 2014.

English Translation of Second Office Action for Chinese Patent Application No. 201180053283.0, dated Nov. 27, 2014.

Notice of Reasons for Rejection for Japanese Patent Application No. 2013-527342, dated Jun. 2, 2015.

English Translation of Final Office Action for Chinese Patent Application No. 201180053283.0, dated May 19, 2015.

\* cited by examiner

COMPOUNDS AND COMPOSITIONS FOR THE INHIBITION OF NAMPT

PRIORITY CLAIM

This application claims priority from PCT International Application No. PCT/US2011/050323 filed on Sep. 2, 2011, which claims priority from U.S. provisional patent applications 61/379,800 filed on Sep. 3, 2010, 61/386,033 filed on Sep. 24, 2010, and 61/476,590 filed on Apr. 18, 2011, all of which are fully incorporated herein by reference in their entirety.

FIELD OF THE INVENTION

The present invention relates to compounds and composition for inhibition of Nicotinamide phosphoribosyltransferase ("NAMPT"), their synthesis, applications and antidote.

BACKGROUND OF THE INVENTION

Nicotinamide adenine dinucleotide (NAD) plays fundamental roles in both cellular energy metabolism and cellular signaling. In energy metabolism, the chemistry of the pyridine ring allows NAD to readily accept and donate electrons in hydride transfer reactions catalyzed by numerous dehydrogenases.

The preparation of a class of compounds, comprising several subclasses, which act as inhibitors of the formation of nicotinamide adenyl nucleotide, and their use thereof as anti-tumour agents, is already described in the patent applications WO00/50399, WO97/48695, WO97/48696, WO97/48397, WO99/31063, WO99/31060, WO99/31087, WO99/31064, WO00/50399, and WO03/80054.

One of these inhibitors, (E)-N-[4-(1-benzoylpiperidin-4-yl)butyl]-3-(pyridine-3-yl)-acrylamide also known as APO866, FK866, WK175, or WK22.175 and hereinafter referred to as FK866 [International Non-proprietary Name], is especially described in the literature as an anticancer agent. FK866 may be used for treatment of diseases implicating deregulated apoptosis such as cancer. It has been demonstrated in the prior art that FK866 interferes with nicotinamide adenyl dinucleotide (also known and hereinafter referred to as NAD) biosynthesis and induces apoptotic cell death without any DNA damaging effects.

Additionally, FK866 ((E)-N-[4-(1-benzoylpiperidin-4-yl)butyl]-3-(pyridin-3-yl)acrylamide) induces apoptosis in HepG2 cells without having primary effects on cellular energy metabolism. (Hasmann M, Schemainda I. FK866, a Highly Specific Noncompetitive Inhibitor of Nicotinamide Phosphoribosyltransferase, Represents a Novel Mechanism for Induction of Tumor Cell Apoptosis. Cancer Res 2003; 63:7436-7442. [PubMed: 14612543]) Instead of causing immediate cytotoxicity, it inhibits NAMPT and depletes the cells of NAD, suggesting that FK866 could be a promising agent against cancer cells that rely on nicotinamide to synthesize NAD. The crystal structure of the NAMPT-FK866 complex reveals that the compound binds at the nicotinamide-binding site of NAMPT to inhibit its activity. FK866 has been tested in a murine renal cell carcinoma model and shown to display anti-tumor, antimetastatic, and anti-angiogenic activities (Drevs J, et al. Antiangiogenic potency of FK866/K22.175, a new inhibitor of intracellular NAD biosynthesis, in murine renal cell carcinoma. Anticancer Res 2003; 23:4853-4858. [PubMed:14981935]).

In a mouse mammary carcinoma model, FK866 also induces a delay in tumor growth and an enhancement in tumor radiosensitivity accompanied with dose-dependent decreases in NAD levels, pH, and energy status. A chemosensitizing effect of FK866 has also been observed on anti-neoplastic 1-methyl-3-nitro-1-nitrosoguanidinium (MNNG)-induced cell death in THP-1 and K562 leukemia cell lines (Pogrebniak A, et al. Chemopotentiating effects of a novel NAD biosynthesis inhibitor, FK866, in combination with antineoplastic agents. Eur J Med Res 2006; 11:313-321. [PubMed: 17052966]).

The efficacy of GMX1777 was evaluated in xenograft models and the pharmacokinetic profile of GMX1778 and its effect on nicotinamide adenine dinucleotide cellular levels was measured by liquid chromatography/mass spectrometry. (Beauparlant P., et al. Preclinical development of the nicotinamide phosphoribosyl transferase inhibitor prodrug GMX1777. Anticancer Drugs. 2009 June; 20(5):346-54).

GMX1777 is a water-soluble intravenously administered prodrug of GMX1778 that Gemin X in-licensed from LEO Pharma (LEO numbers: EB1627 and CHS828, respectively). These compounds and other substituted cyanoguanidines have the structures of Table 1.

TABLE 1

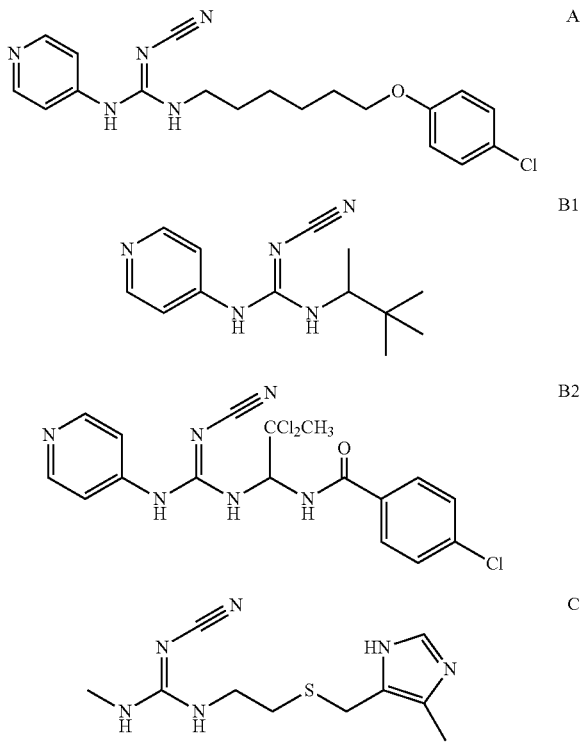

Substituted Cyanoguanidines with Defined Pharmacological Effects:
A Cytotoxic CHS 828;
B Potassium channel openers pinacidil (B1) and 12 g of compound as described in Perez-Medrano et al (B2); and
C Histamine-II receptor antagonist cimetidine. (from Lövborg et al. *BMC Research Notes* 2009 2:114 doi: 10.1186/1756-0500-2-114)

More recently, CHS-828 has been identified as a NAMPT inhibitor (Olesen U H, et al. Anticancer agent CHS-828 inhibits cellular synthesis of NAD. Biochem Biophys Res Commun 2008; 367:799-804. [PubMed: 18201551]). CHS- 828 has been shown that this compound potently inhibits cell growth in a broad range of tumor cell lines, although the detailed mechanism for this inhibitory effect of CHS-828 remains undetermined (Ravaud A, et al. Phase I study and guanidine kinetics of CHS-828, a guanidine-containing compound, administered orally as a single dose every 3 weeks in solid tumours: an ECSG/EORTC study. Eur J Cancer 2005; 41:702-707. [PubMed: 15763645]). Both FK866 and CHS-828 are currently in clinical trials for cancer treatments.

There are numerous uses for drugs which inhibit NAMPT.

Lack of NAMPT expression strongly affects development of both T and B lymphocytes. By using mutant forms of this protein and a well-characterized pharmacological inhibitor (FK866), authors demonstrated that the ability of the NAMPT to regulate cell viability during genotoxic stress requires its enzymatic activity. Collectively, these data demonstrate that NAMPT participates in cellular resistance to genotoxic/oxidative stress, and it may confer to cells of the immune system the ability to survive during stressful situations such as inflammation. (Rongvaux, A., et al. *The Journal of Immunology*, 2008, 181: 4685-4695).

NAMPT may also have effects on endothelium (EC) in relation to high glucose levels, oxidative stress and on aging. It is also believed that NAMPT may enable proliferating human EC to resist the oxidative stress of aging and of high glucose, and to productively use excess glucose to support replicative longevity and angiogenic activity.

SUMMARY OF THE INVENTION

One aspect of this invention is the provision of compounds, compositions, kits, and antidotes for the NAMPT pathway in mammals having a compound of the formula I:

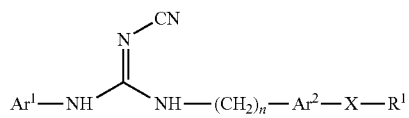

I wherein
Ar$^1$ is aryl, heteroaryl, arylalkyl or heteroarylalkyl, wherein the heteroatom of each of said heteroaryl and heteroaryl independently numbers 1, 2 or 3, and is independently selected from N, S or O, further wherein each of said aryl, heteroaryl, arylalkyl and heteroarylalkyl may optionally independently be either substituted or fused with aryl or heteroaryl, still further wherein any of said aryl, heteroaryl, arylalkyl and heteroarylalkyl is either unsubstituted or optionally independently substituted with one or more substituents which can be the same or different and are independently selected from the group consisting of deuterium, halo, cyano, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, alkyl, alkenyl, alkynyl, alkoxy-, -aryloxy-, (alkoxyalkyl)oxy-, (alkoxyalkyl)amino-, -cycloalkyl, -heterocycloalkyl, -aryl, —C(O)-alkyl, —C(O)-aryl, —S(O)-aryl, —NH—C(O)-alkyl, —NH—C(O)-aryl and heteroaryl, with the proviso that no two adjacent ring heteroatoms on a ring are both S or both O;
n is 0, 1, 2, 3 or 4;
Ar$^2$ is aryl or heteroaryl, with each of said aryl and heteroaryl being either unsubstituted or optionally independently substituted with 1, 2, 3 or 4 substituents which can be the same or different and are independently selected from the group consisting of deuterium, halo, cyano, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, alkyl, alkenyl, alkynyl, alkoxy-, -aryloxy-, (alkoxyalkyl)oxy-, (alkoxyalkyl)amino-, -cycloalkyl, -heterocycloalkyl, -aryl, —C(O)-alkyl, —C(O)-aryl, —S(O)-aryl, —NH—C(O)-alkyl, —NH—C(O)-aryl and heteroaryl, with the proviso that no two adjacent ring heteroatoms on a ring are both S or both O;
X is S, S(O), S(O)$_2$, O or C(O);
R$^1$ is cycloalkyl, —CH$_z$F$_{3-z}$, aryl, heterocycloalkyl, heteroaryl, alkyl, alkenyl, alkynyl, (aryl)alkyl-, (heteroaryl)alkyl- or (heterocycloalkyl)alkyl-, (i) wherein each of said cycloalkyl, aryl, heterocycloalkyl, heteroaryl and alkyl is either unsubstituted or optionally independently substituted with 1, 2, 3, 4 or 5 substituents which can be the same or different and are independently selected from the group consisting of deuterium, halo, cyano, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, alkyl, alkenyl, alkynyl, alkoxy-, aryloxy-, (alkoxyalkyl)amino-, -cycloalkyl, -heterocycloalkyl, -aryl, —S(O)$_2$-alkyl, —S(O)$_2$-aryl, —S(O)$_2$—CF$_3$, —C(O)N(alkyl)$_2$, —C(O)alkyl, —NH—C(O)-alkyl, —NH—C(O)-aryl, methylenedioxy, heteroaryl, arylalkyl-, (heteroaryl)alkyl-, and (heterocycloalkyl)alkyl-, (ii) further wherein each of said cycloalkyl, aryl, heterocycloalkyl, and heteroaryl may additionally be fused with independently selected aryl, heteroaryl, heterocycloalkyl or cyloalkyl; and z is 0, 1 or 2;

and pharmaceutically acceptable salts, solvates, esters, prodrugs or isomers thereof.

Another aspect of the invention is compounds of Formula I where X=SO$_2$, and the formula becomes Formula II:

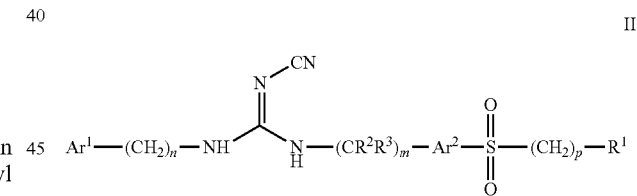

II wherein
Ar$^1$ is aryl or heteroaryl, wherein said aryl or heteroaryl is unsubstituted or substituted with one or more substituents independently selected from the group consisting of:
deuterium, halo, cyano, alkyl, hydroxyalkyl, cyanoalkyl, haloalkyl, alkenyl, alkynyl, alkoxy, haloalkoxy, aryloxy, —NR$^a$R$^b$, —C(O)N(R$^a$R$^b$), —C(O)-alkyl, —C(O)-aryl, —S(O)-aryl, —NH—C(O)-alkyl, —NH—C(O)-aryl, -(alkoxyalkyl)oxy-, cycloalkyl, heterocycloalkyl, aryl, and heteroaryl;
Ar$^2$ is unsubstituted aryl or heteroaryl;
R$^1$ is cycloalkyl, aryl, heterocycloalkyl, or heteroaryl,
(i) wherein each of said cycloalkyl, aryl, heterocycloalkyl and heteroaryl is either unsubstituted or optionally independently substituted with 1, 2, 3, 4 or 5 substituents which can be the same or different and are independently selected from the group consisting of:
deuterium, halo, cyano, alkyl, cyanoalkyl, haloalkyl, alkenyl, alkynyl, alkoxy, alkylalkoxy, haloalkoxy, aryloxy, —NR$^a$R$^b$, —CONR$^a$R$^b$, —S(O)$_2$-alkyl, —S(O)$_2$-aryl, —S(O)$_2$N(alkyl)$_2$, —S(O)$_2$—CF$_3$, —C(O)alkyl, —NH—C(O)alkyl, —NH—C(O)aryl, methylenedioxy, —(CH$_2$)$_q$cycloalkyl, —(CH$_2$)$_q$aryl, —(CH$_2$)$_q$heteroaryl, and —(CH$_2$)$_q$heterocycloalkyl,
(ii) wherein each of said cycloalkyl, aryl, heterocycloalkyl, and heteroaryl may additionally be unsubstituted or substituted by one or more halo, cyano, alkyl or alkoxy or may be be fused with independently selected aryl, heteroaryl, heterocycloalkyl or cyloalkyl;

R$^a$ and R$^b$ are independently H, alkyl, alkoxy, aryl, alkoxyalkyl, —S(O)$_2$alkyl and cycloalkyl or R$^a$ and R$^b$ can form a 5 or 6 membered heterocycloalkyl group together with the nitrogen atom to which they are attached, wherein said heterocycloalkyl group may contain one or more additional heteroatom(s) selected from N, S or O;

R$^2$ and R$^3$ are H or deuterium;

m, n, p and q are independently 0, 1 or 2.

Another aspect of this invention is the provision of methods of treating a disease via the inhibition of NAMPT in a subject (e.g., a human) in need thereof by administering to the subject an effective amount of the compound or the pharmaceutical formulation of the present invention.

Still another aspect of this invention is to provide a method for treating, preventing, inhibiting or eliminating a disease or condition in a patient by inhibiting NAMPT in said patient by administering a therapeutically effective amount of at least one compound of this disclosure, wherein said disease or condition is selected from the group consisting of cancer, ovarian cancer, breast cancer, uterine cancer, colon cancer, cervical cancer, lung cancer, prostate cancer, skin cancer, bladder cancer, pancreatic cancer, leukemia, lymphoma, Hodgkin's disease, viral infections, Human Immunodeficiency Virus, hepatitis virus, herpes virus, herpes simplex, inflammatory disorders, irritable bowel syndrome, inflammatory bowel disease, rheumatoid arthritis, asthma, chronic obstructive pulmonary disease, osteoarthritis, osteoporosis, dermatitis, atoptic dermatitis, psoriasis, systemic lupus erythematosis, multiple sclerosis, psoriatic arthritis, ankylosing spodylitis, graft-versus-host disease, Alzheimer's disease, cerebrovascular accident, atherosclerosis, diabetes, glomerulonephiritis, metabolic syndrome, non-small cell lung cancer, small cell lung cancer, multiple myeloma, leukemias, lymphomas, squamous cell cancers, kidney cancer, uretral and bladder cancers, cancers of head and neck, cancers of the brain and central nervous system.

Another preferred embodiment is a pharmaceutical formulation comprising a pharmaceutically acceptable compound of the present invention, which provides, upon administration to a human, a decrease in tumor burden and/or metastases. The pharmaceutical formulation can be administered by oral means or other suitable means.

Yet another embodiment is a method of treating ovarian cancer in a subject (e.g., a human) in need thereof by administering to the subject an effective amount of the compound or the pharmaceutical formulation of the present invention.

Yet another embodiment is a method of treating colon cancer in a subject (e.g., a human) in need thereof by administering to the subject an effective amount of the compound or the pharmaceutical formulation of the present invention.

Yet another embodiment is a method of treating breast cancer in a subject (e.g., a human) in need thereof by administering to the subject an effective amount of the pharmaceutical formulation of the present invention. in a subject (e.g., a human) in need thereof by administering to the subject an effective amount of the compound or the pharmaceutical formulation of the present invention.

Yet another embodiment is a method of treating leukemia in a subject (e.g., a human) in need thereof by administering to the subject an effective amount of the compound or the pharmaceutical formulation of the present invention.

Yet another embodiment is a method of treating colon cancer, before or after surgical resection and/or radiation therapy, in a subject (e.g., a human) in need thereof by administering to the subject an effective amount of the compound or the pharmaceutical formulation of the present invention.

Yet another embodiment is a method of treating cancer, before or after surgical resection and/or radiation therapy, in a subject (e.g., a human) in need thereof by administering to the subject an effective amount of the compound or the pharmaceutical formulation of the present invention, including adjunctive therapy to treat nausea, with or without dexamethasone.

Yet another embodiment is a method of treating cancer, before or after surgical resection and or radiation therapy, in a subject (e.g., a human) in need thereof by administering to the subject an effective amount of the compound or the pharmaceutical formulation of the present invention, including adjunctive therapy with one or more additional therapeutic agents, or their pharmaceutically acceptable salts thereof. Non-limiting examples of such additional therapeutic agents include cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil or 5-FU); anti-metabolites (such as methoxtrexate); alkylating agents (such as temozolomide, cyclophosphamide); Farnesyl protein transferase inhibitors (such as, SARASAR™ (4-[2-[4-[(11R)-3,10-dibromo-8-chloro-6,11-dihydro-5H-benzo[5,-6]cyclohepta[1,2-b]pyridin-11-yl-]-1-piperidinyl]-2-oxoethyl]-1-piperidine-carboxamide, or SCH 66336), tipifarnib (Zarnestra® or R115777 from Janssen Pharmaceuticals), L778,123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.); signal transduction inhibitors (such as, Iressa® (from Astra Zeneca Pharmaceuticals, England), Tarceva® (EGFR kinase inhibitors), antibodies to EGFR (e.g., C225), GLEEVEC® (C-abl kinase inhibitor from Novartis Pharmaceuticals, East Hanover, N.J.); interferons such as, for example, Intron® (from Merck & Company), Peg-Intron® (from Merck & Company); hormonal therapy combinations; aromatase combinations; ara-C, adriamycin, cytoxan, and gemcitabine.

Other anti-cancer (also known as anti-neoplastic) agents include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN®. from Sanofi-Synthelabo Pharmaceuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade®, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Ifosfomide, Rituximab, C225, and Campath, 5-fluorouracil and leucovorin, with or without a 5-HT$_3$ receptor inhibitor (e.g., dolansetron, granisetron, ondansetron) with or without dexamethasone.

If formulated as a fixed dose, such combination products employ the compounds of this invention within the dosage range described herein (or as known to those skilled in the art) and the other pharmaceutically active agents or treatments within its dosage range. For example, the CDC2 inhibitor olomucine has been found to act synergistically with known cytotoxic agents in inducing apoptosis (J. Cell Sci., (1995) 108, 2897). The compounds of the invention may also be administered sequentially with known anticancer or cytotoxic agents when a combination formulation is inappropriate. In any combination treatment, the invention is not limited in the sequence of administration; compounds of the Formulas may be administered either prior to or after administration of the known anticancer or cytotoxic agent. For example, the cytotoxic activity of the cyclin-dependent kinase inhibitor flavopiridol is affected by the sequence of administration with anticancer agents. Cancer Research, (1997) 57, 3375. Such techniques are within the skills of persons skilled in the art as well as attending physicians.

Any of the aforementioned methods may be augmented by administration of fluids (such as water), loop diuretics, one or more of a chemotherapeutic or antineoplastic agent, such as leucovorin and fluorouracil, and an adjunctive chemotherapeutic agent (such as filgrastim and erythropoietin), or any combination of the foregoing.

Yet another embodiment is a method for administering a compound of the instant invention to a subject (e.g., a human) in need thereof by administering to the subject the pharmaceutical formulation of the present invention.

Yet another embodiment is a method of preparing a pharmaceutical formulation of the present invention by mixing at least one pharmaceutically acceptable compound of the present invention, and, optionally, one or more pharmaceutically acceptable additives or excipients.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally or intravenously.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 1000 mg, preferably from about 1 mg to about 500 mg, more preferably from about 1 mg to about 250 mg, still more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of the invention is a pharmaceutical composition comprising a compound according to the invention and a cell rescuing agent that can be selected from the group consisting of nicotinamide, nicotinic acid and nicotinamide mononucleotide (NMN).

Definitions

As used above, and throughout this disclosure, the following terms, unless otherwise indicated, shall be understood to have the following meanings. If a definition is missing, convention definition as known to one skilled in the art controls.

"Patient" includes both human and animals.

"Mammal" means humans and other mammalian animals.

The term "inhibitor" refers to a molecule such as a compound, a drug, an enzyme activator or a hormone that blocks or otherwise interferes with a particular biologic activity.

The terms "effective amount" or "therapeutically effective amount" refer to a sufficient amount of the agent to provide the desired biological result. That result can be reduction and/or alleviation of the signs, symptoms, or causes of a disease, or any other desired alteration of a biological system. For example, an "effective amount" for therapeutic use is the amount of the composition comprising a compound as disclosed herein required to provide a clinically significant decrease in a disease. An appropriate "effective" amount in any individual case may be determined by one of ordinary skill in the art using routine experimentation. Thus, the expression "effective amount" generally refers to the quantity for which the active substance has therapeutic effects. In the present case the active substance is the inhibitor of the formation of Nicotinamide phosphoribosyltransferase (NAMPT).

As used herein, the terms "treat" or "treatment" are synonymous with the term "prevent" and are meant to indicate a postponement of development of diseases, preventing the development of diseases, and/or reducing severity of such symptoms that will or are expected to develop. Thus, these terms include ameliorating existing disease symptoms, preventing additional symptoms, ameliorating or preventing the underlying metabolic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

By "pharmaceutically acceptable" or "pharmacologically acceptable" is meant a material which is not biologically or otherwise substantially undesirable, i.e., the material may be administered to an individual without causing any substantially undesirable biological effects or interacting in a substantially deleterious manner with any of the components of the composition in which it is contained. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

"Carrier materials" or what are also referred to as "excipients" include any commonly used excipients in pharmaceutics and should be selected on the basis of compatibility and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may comprise, e.g., acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, and the like. See, e.g., Hoover, John E., *Remington's Pharmaceutical Sciences*, Mack Publishing Co., Easton, Pa. 1975.

As used herein, the term "subject" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the present invention, the mammal is a human.

As used herein, "alkyl" means a straight chain or branched saturated chain having from 1 to 10 carbon atoms. Representative saturated alkyl groups include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, n-pentyl, isopentyl, neopentyl, n-hexyl and the like, and longer alkyl groups, such as heptyl, and octyl and the like. An alkyl group can be unsubstituted or substituted. Alkyl groups containing three or more carbon atoms may be straight, branched or cyclized. As used herein, "lower alkyl" means an alkyl having from 1 to 6 carbon atoms.

As used herein, an "alkenyl group" includes an unbranched or branched hydrocarbon chain having one or more double bonds therein. The double bond of an alkenyl group can be unconjugated or conjugated to another unsaturated group. Illustrative alkenyl groups include, but are not limited to, ($C_2$-$C_8$) alkenyl groups, such as ethylenyl, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl and the like. An alkenyl group can be unsubstituted or substituted.

The term "hydroxyalkyl" denotes an alkyl group as defined above wherein at least one of the hydrogen atoms of the alkyl group is replaced by a hydroxy group. Examples of hydroxyalkyl include, but are not limited to, methyl, ethyl, propyl, isopropyl, isobutyl, sec-butyl, tert-butyl, pentyl or n-hexyl wherein one or more hydrogen atoms are replaced by OH, as well as those hydroxyalkyl groups specifically illustrated by the examples herein below.

The term "cyanoalkyl" denotes an alkyl group as defined above wherein at least one of the hydrogen atoms of the alkyl group is replaced by a cyano (—CN) group.

As used herein, "alkynyl group" includes an unbranched or branched hydrocarbon chain having one or more triple bonds therein. The triple bond of an alkynyl group can be unconjugated or conjugated to another unsaturated group. Suitable alkynyl groups include, but are not limited to, ($C_2$-$C_6$) alkynyl groups, such as ethynyl, propynyl, butynyl, pentynyl, hexynyl, methylpropynyl, 4-methyl-1-butynyl, 4-propyl-2-pentynyl, 4-butyl-2-hexynyl and the like. An alkynyl group can be unsubstituted or substituted.

The term "haloalkyl" denotes an alkyl group as defined above wherein at least one of the hydrogen atoms of the alkyl group is replaced by a halogen atom, preferably fluoro or chloro, most preferably fluoro. Examples of haloalkyl include, but are not limited to, methyl, ethyl, propyl, isopropyl, isobutyl, sec-butyl, tert-butyl, pentyl or n-hexyl wherein one or more hydrogen atoms are replaced by Cl, F, Br or I atom(s), as well as those haloalkyl groups specifically illustrated by the examples herein below. Among the preferred haloalkyl groups are monofluoro-, difluoro- or trifluoro-methyl, -ethyl or -propyl, for example 3,3,3-trifluoro-propyl, 2-fluoroethyl, 2,2,2-trifluoroethyl, fluoromethyl, trifluoromethyl.

The terms "trifluoromethyl," "sulfonyl," and "carboxyl" include $CF_3$, $SO_2$, and $CO_2H$, respectively.

The term "hydroxy" means an OH group.

The term "alkoxy" as used herein includes —O-(alkyl), wherein alkyl is defined above.

The term "aminoalkyl" as used herein means a group having one or more nitrogen atoms and one or more alkyl groups as defined above binding to the nitrogen.

"Aralkyl" or "arylalkyl" means an aryl-alkyl-group in which the aryl and alkyl are as define herein. Preferred aralkyls comprise a lower alkyl group. Non-limiting examples of suitable aralkyl groups include benzyl, 2-phenethyl and naphthalenylmethyl. The bond to the parent moiety is through the alkyl.

"Heteroarylalkyl" means a heteroaryl moiety as defined herein linked via an alkyl moiety (defined above) to a parent core. Non-limiting examples of suitable heteroaryls include 2-pyridinylmethyl, quinolinylmethyl and the like.

The term "bicyclic heteroaryl" means a structure having atoms arranged in two rings fused together with at least two atoms common to each ring, and at least one of the rings being a heteroaryl ring. Non limiting examples of bicyclic heteroaryl comprise bicyclic heteroaryl groups comprising 1, 2. 3 or 4 heteroatoms independently selected from N, S or O. Illustrative examples of bicyclic heteroaryls include but are not limited to:

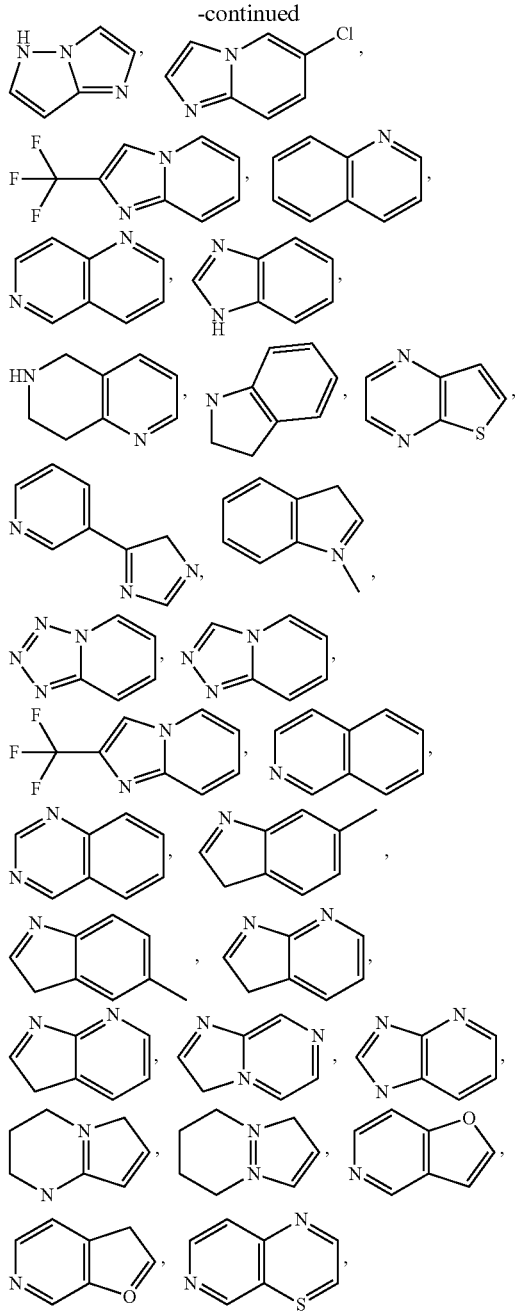

and the like.

Further examples of bicyclic heteroaryls include but are not limited to:

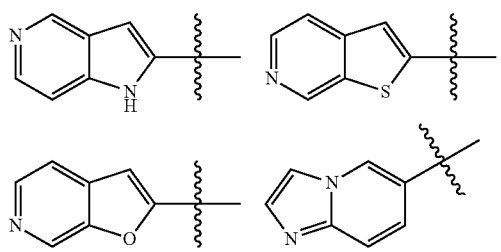

-continued

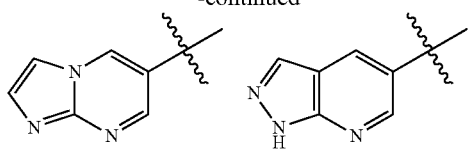

These bicyclic heteroaryl groups can be substituted as defined for Ar¹ herein.

"Heterocyclylalkyl" or means a heterocyclyl moiety as defined herein linked via an alkyl moiety (defined above) to a parent core. Non-limiting examples of suitable heterocyclylalkyls include piperidinylmethyl, piperazinylmethyl and the like.

It should also be noted that any carbon as well as heteroatom with unsatisfied valences in the text, schemes, examples and Tables herein is assumed to have the sufficient number of hydrogen atom(s) to satisfy the valences.

When any variable (e.g., aryl, heterocycle, $R^2$, etc.) occurs more than one time in any constituent or in the Formulas, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

The term "deuterium" as used herein means a stable isotope of hydrogen having odd numbers of protons and neutrons.

The term "halo" as used herein means a substituent having at least one halogen selected from fluorine, chlorine, bromine, and iodine.

The term "cyano" as used herein means a substituent having a carbon atom joined to a nitrogen atom by a triple bond.

The term "amino" as used herein means a substituent containing at least one nitrogen atom.

The term "(amino)alkoxy" as used herein means a substituent having at least one amino group and at least one alkoxy group.

The term "aryloxy" as used herein means a substituent of the form Ar—O— where Ar is an aryl group as defined herein.

The term "methylenedioxy" as used herein means a functional group with the structural formula —O—CH$_2$—O— which is connected to the molecule by two chemical bonds via the oxygens.

As used herein, "alkoxyalkyl" means -(alkyl)-O-(alkyl), wherein each "alkyl" is independently an alkyl group defined above.

The term "(alkoxyalkyl)amino" as used herein means a substituent having at least one alkoxyalkyl group as defined above and at least one amino group as defined above.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein. Illustrative examples of aryl groups include, but are not limited to phenyl, naphthalene and the following moieties:

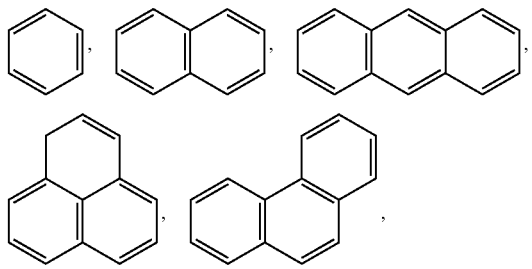

and the like.

Illustrative and non limiting examples of substituted aryl groups include:

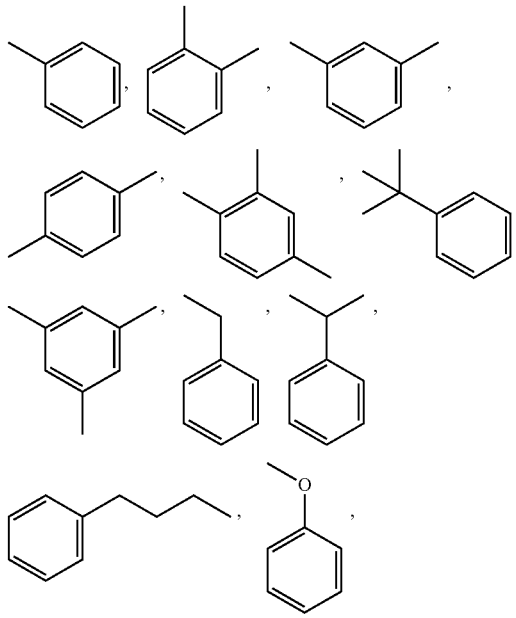

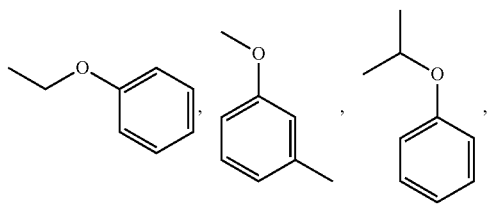

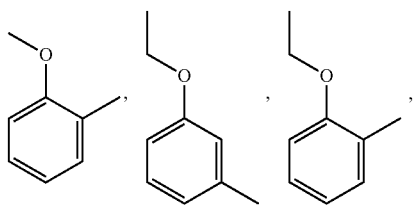

-continued

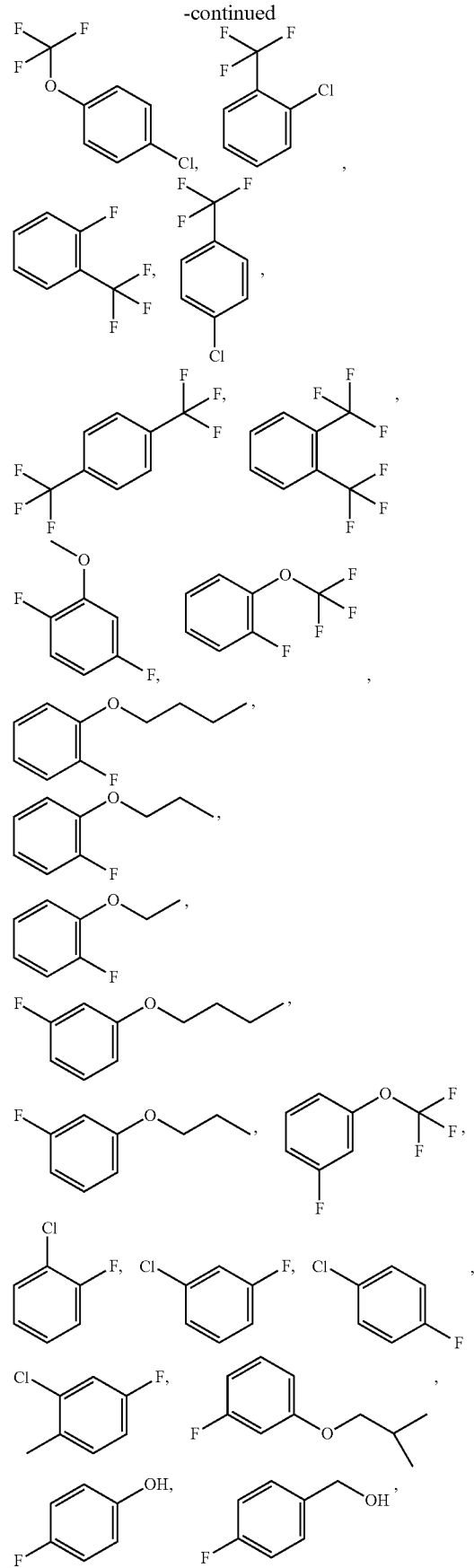
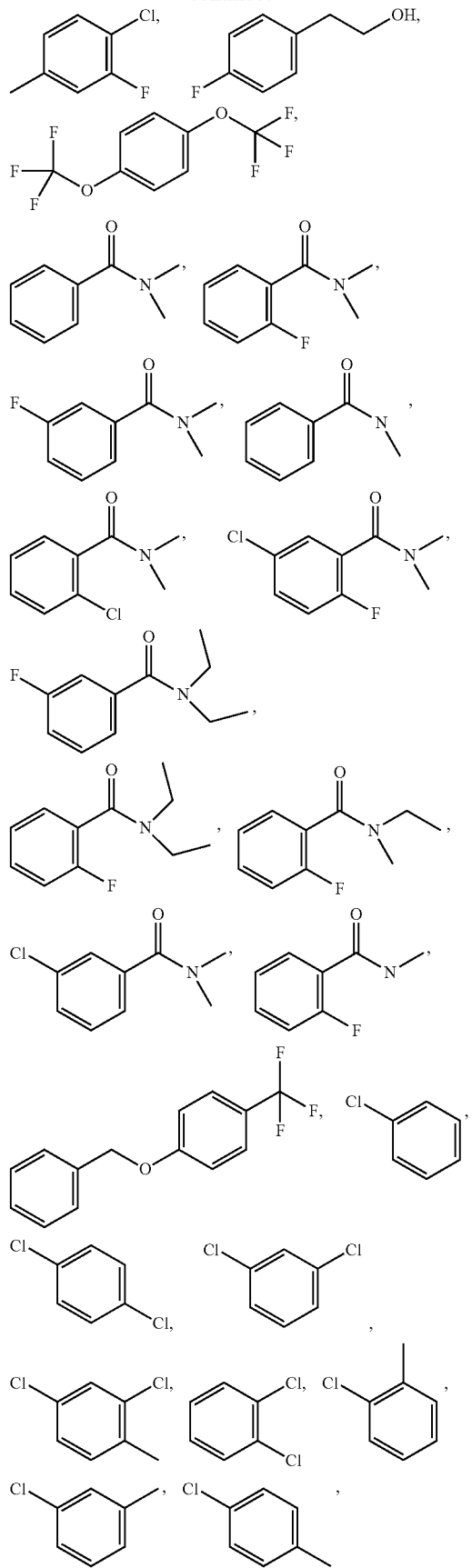

-continued

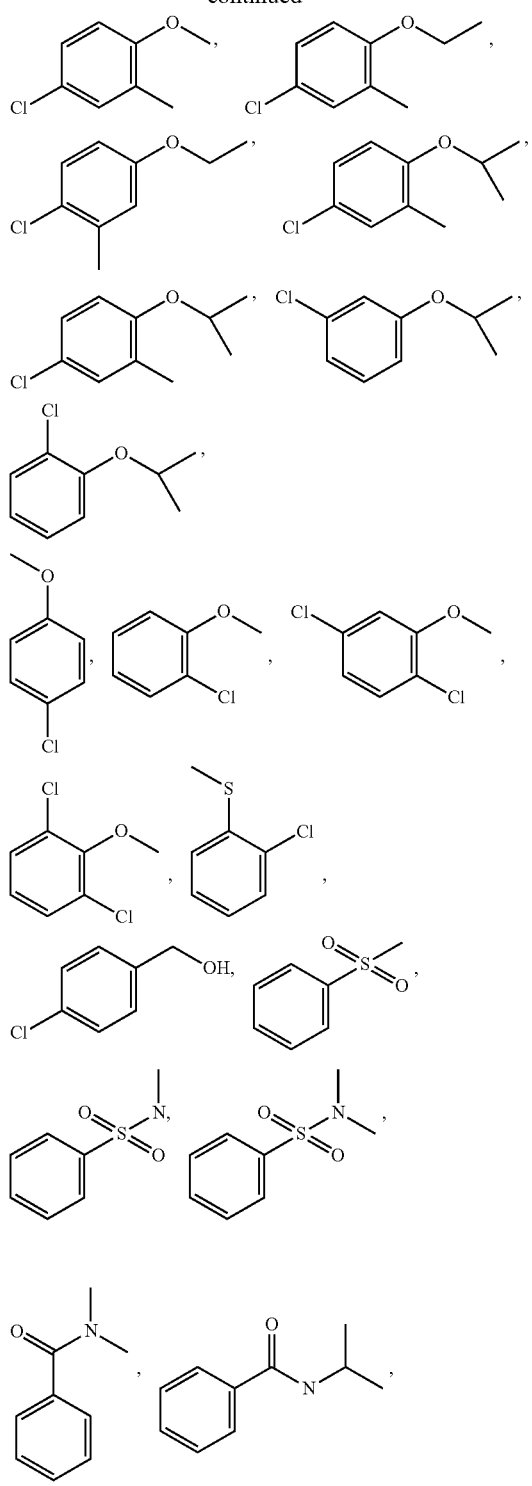

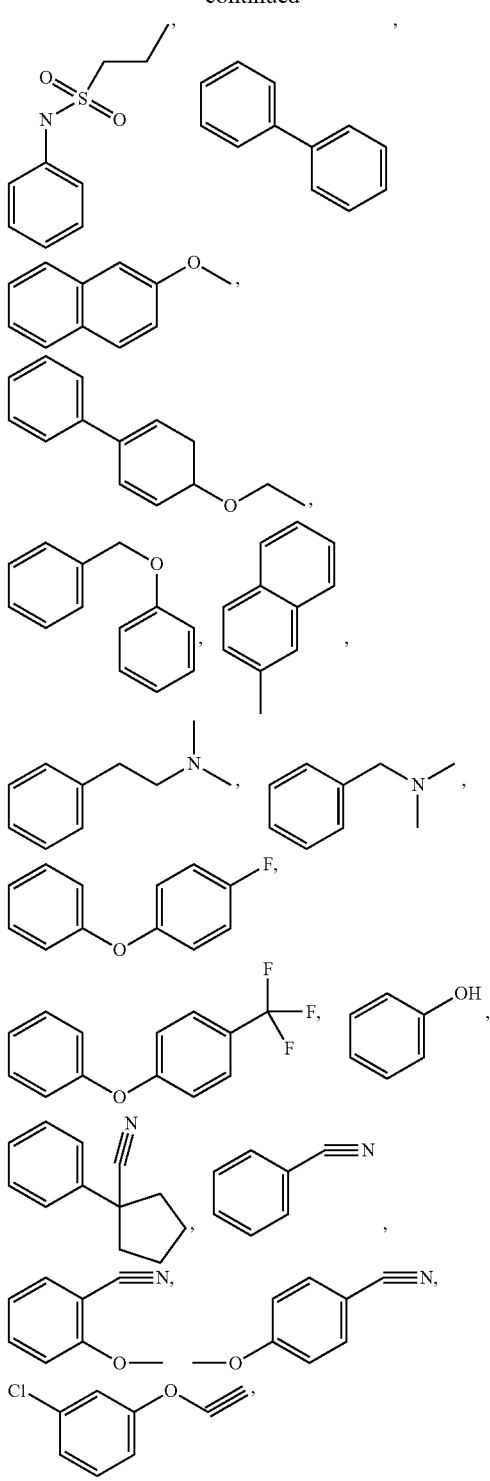

and the like.

As used herein, the term "heteroaryl" refers to a monocyclic, or fused polycyclic, aromatic heterocycle (ring structure having ring atoms selected from carbon atoms as well as nitrogen, oxygen, and sulfur heteroatoms) having from 3 to 24 ring atoms per ring. Illustrative examples of heteroaryl and substituted heteroaryl groups include, but are not limited to the following moieties:

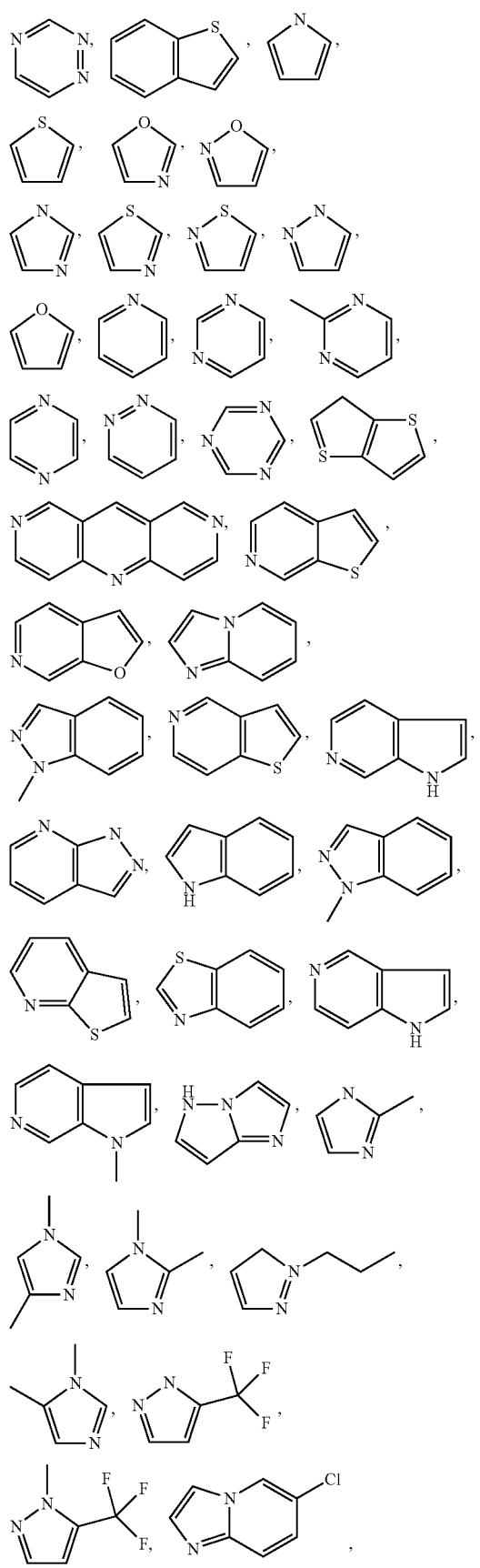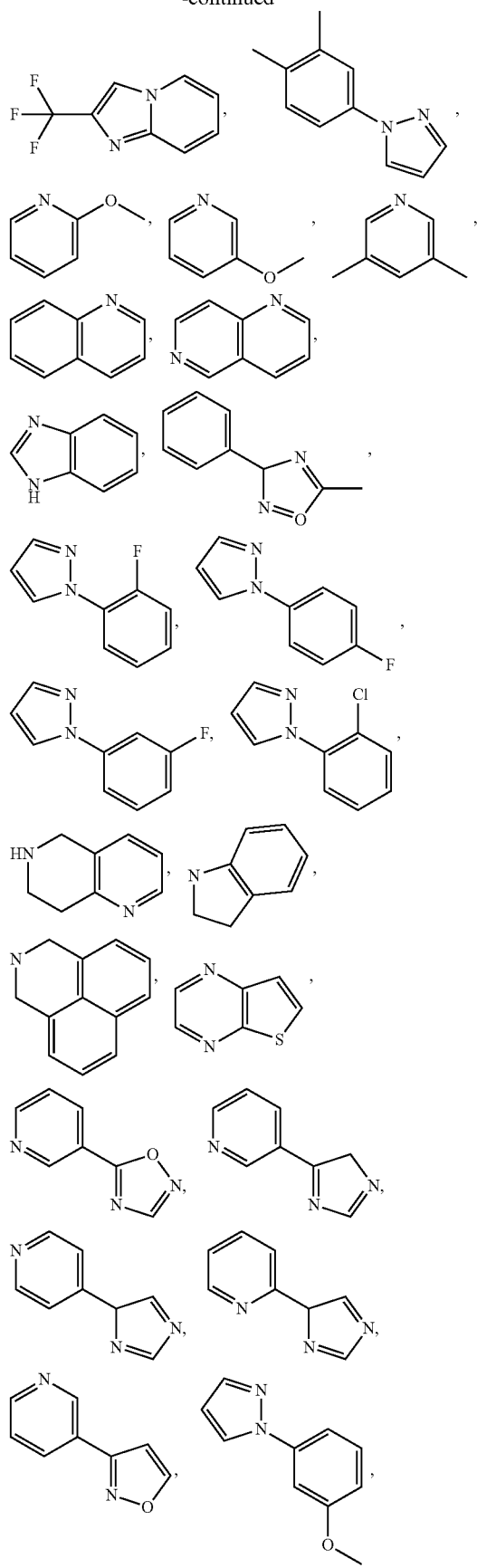

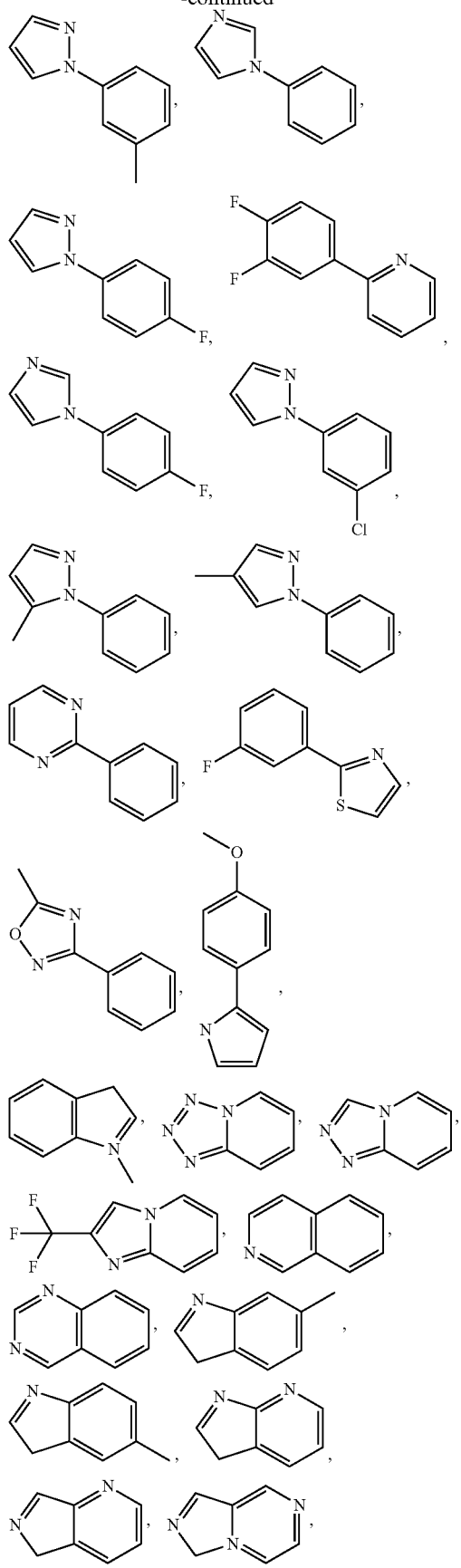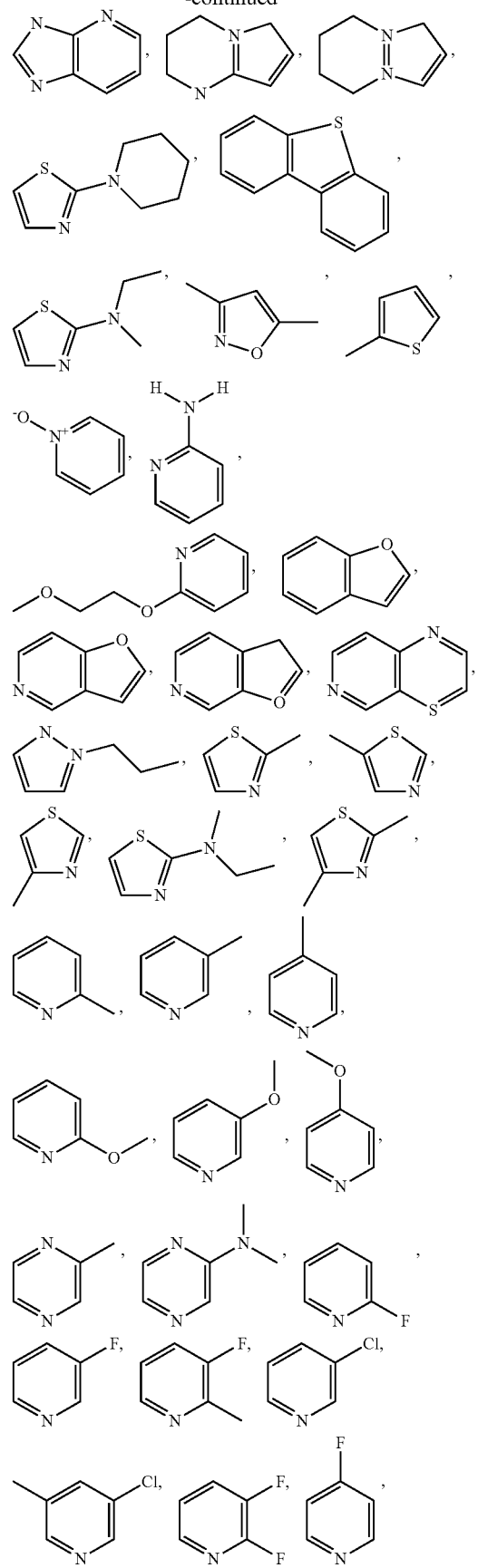

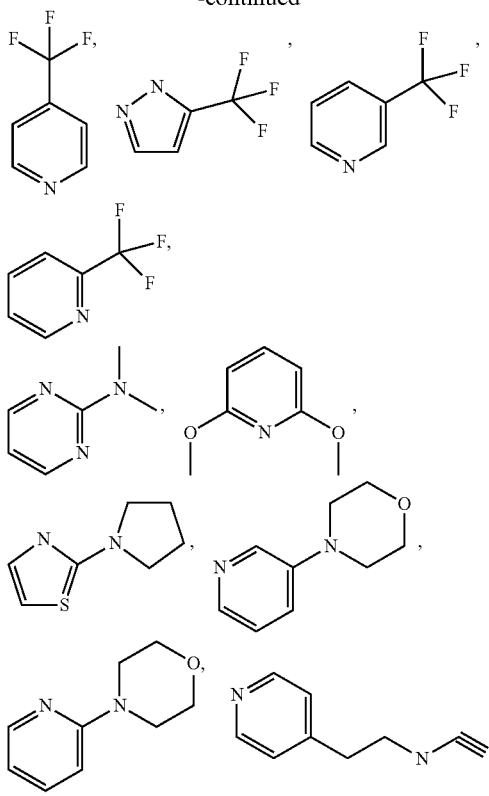

and the like.

As used herein, the term "cycloalkyl" refers to a saturated or partially saturated, monocyclic or fused or spiro polycyclic, carbocycle having from 3 to 24 or 3 to 6 carbon atoms per ring: e.g. ($C_3$-$C_6$)-cycloalkyl. Illustrative examples of cycloalkyl groups include, but are not limited to, the following moieties:

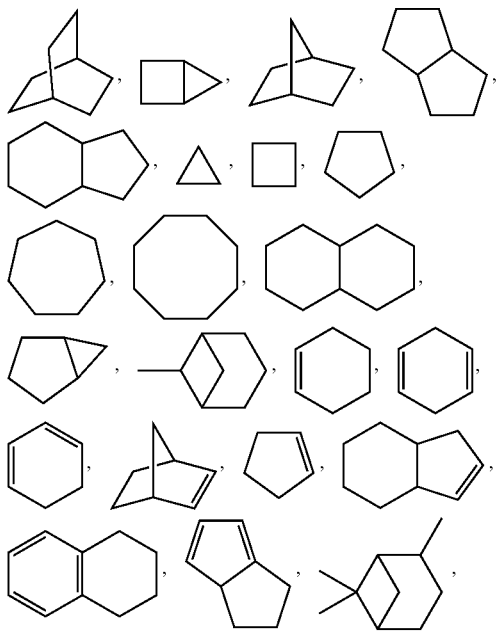

and the like.

As used herein, the term "heterocyclyl" or "heterocycloalkyl" refers to a monocyclic, or fused or spiro, polycyclic, ring structure that is saturated or partially saturated and has from 3 to 24 or 5 to 6 ring atoms per ring selected from C atoms and N, O, and S heteroatoms. Illustrative examples of heterocycloalkyl and substituted heterocycloalkyl groups include, but are not limited to:

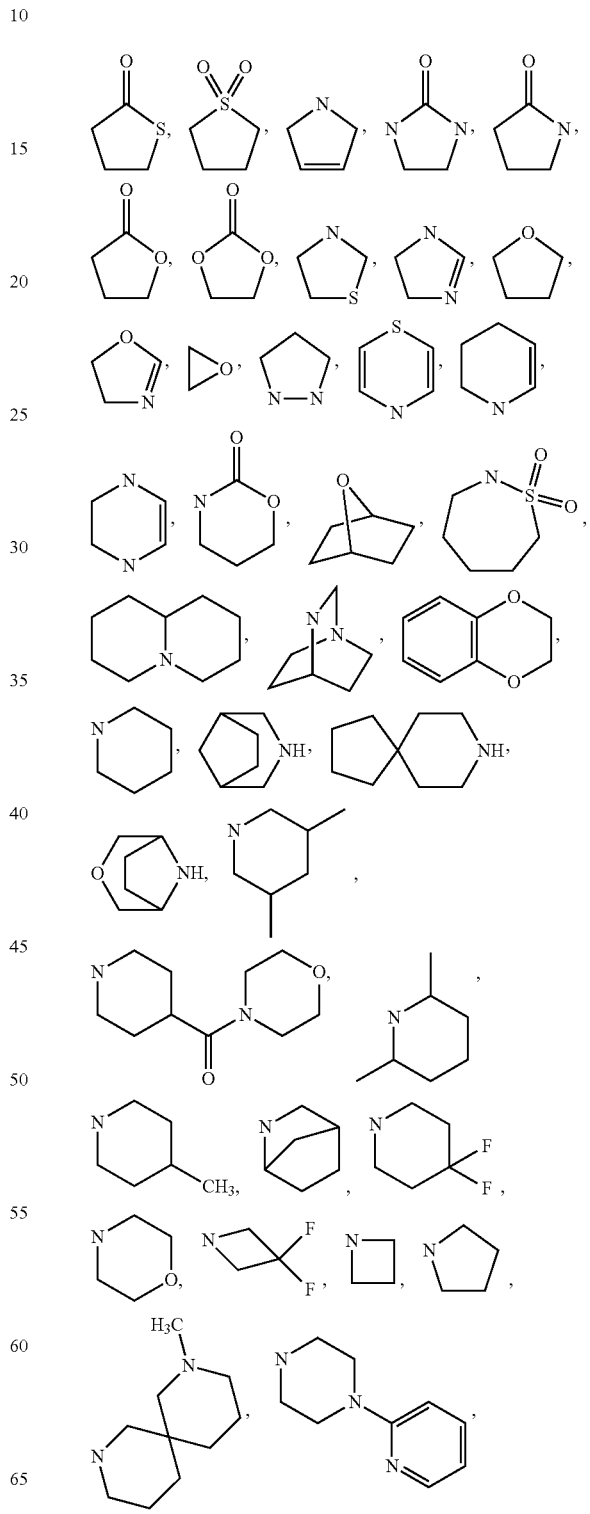

-continued
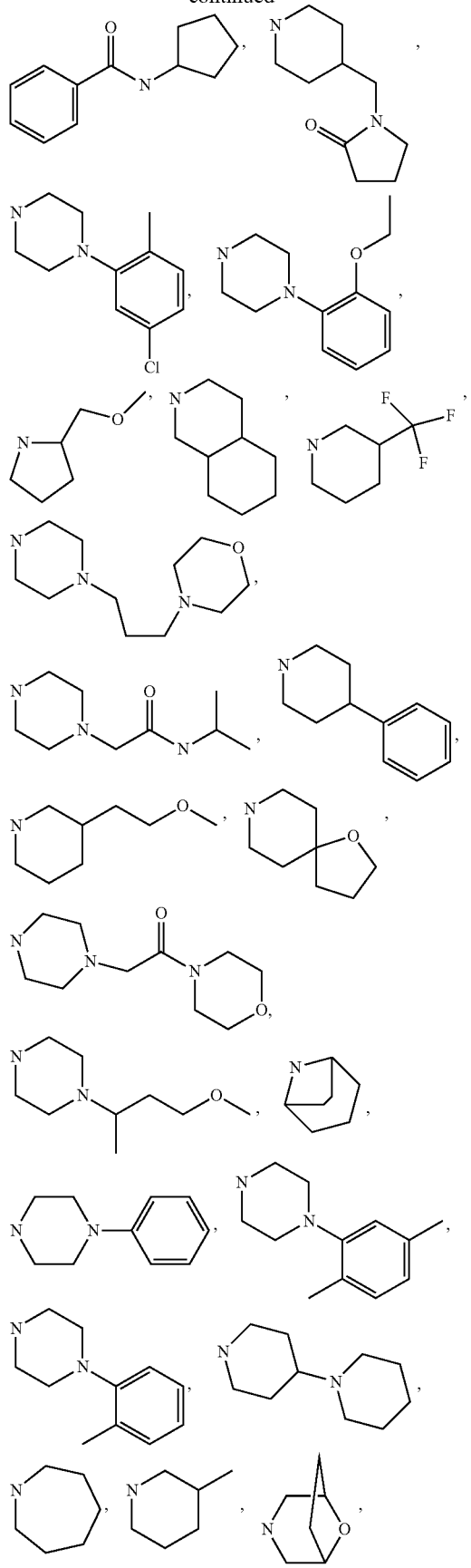
-continued
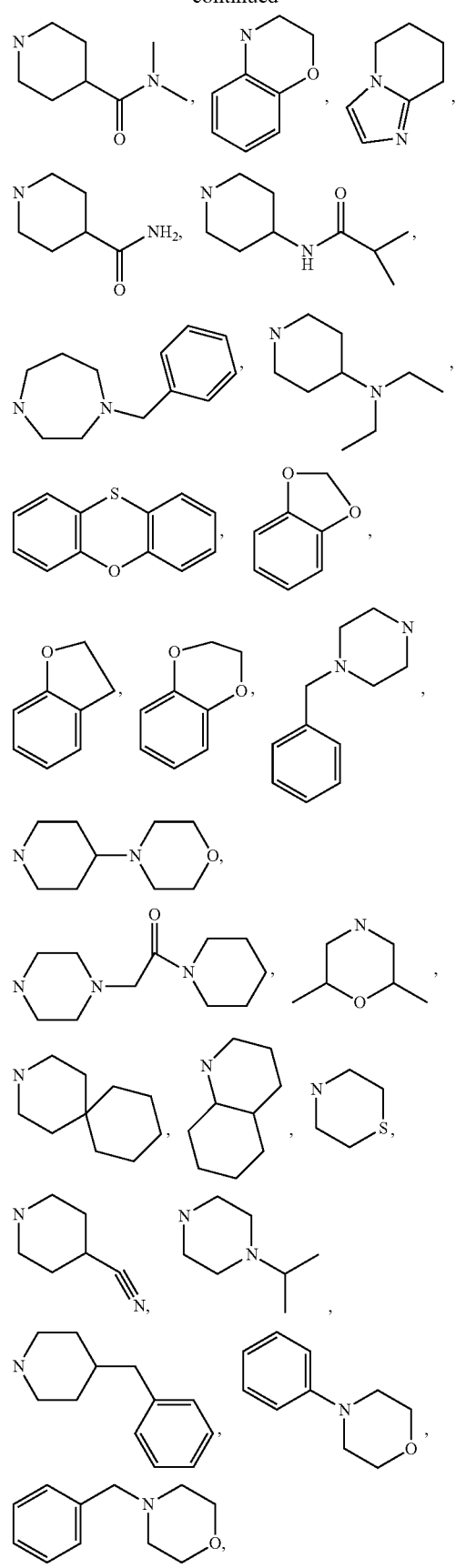

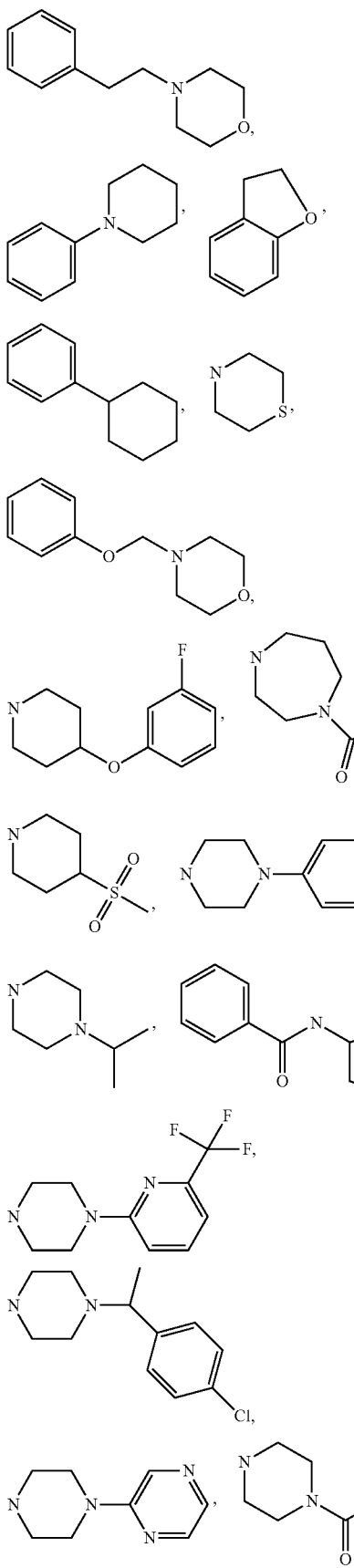
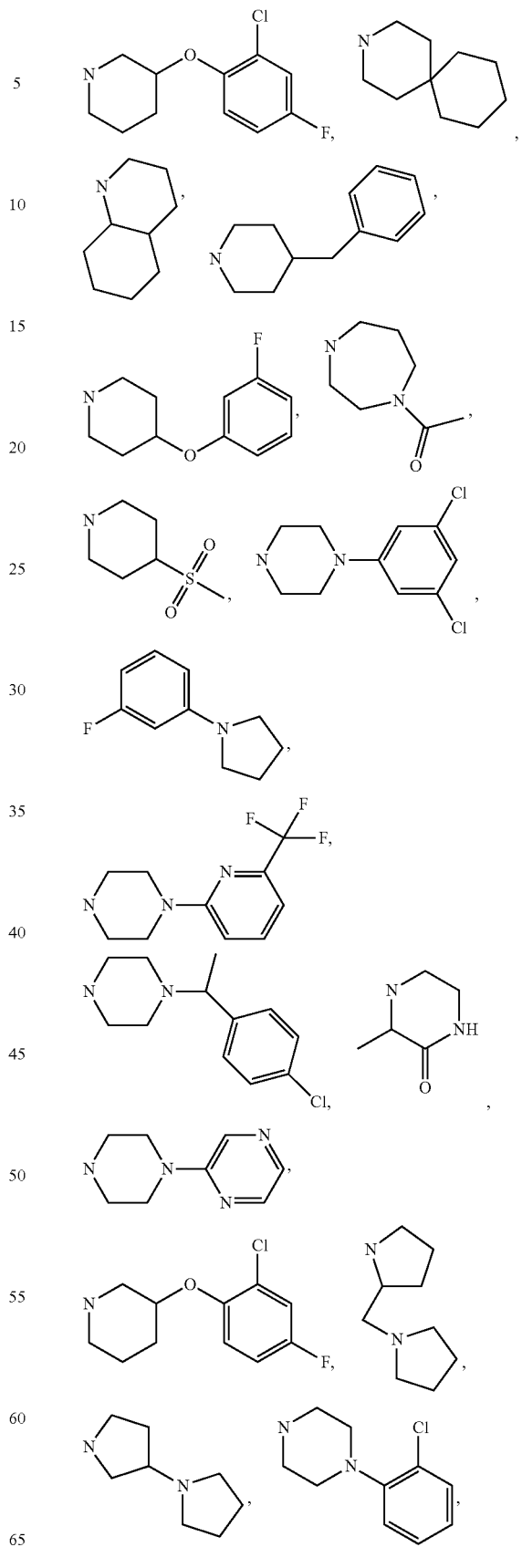

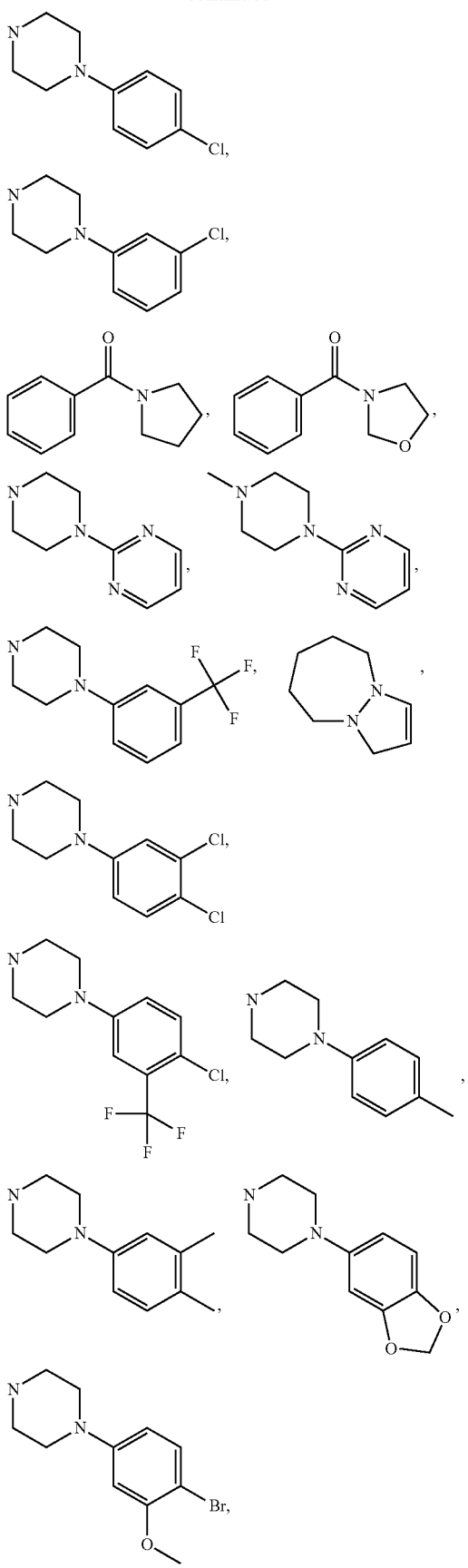
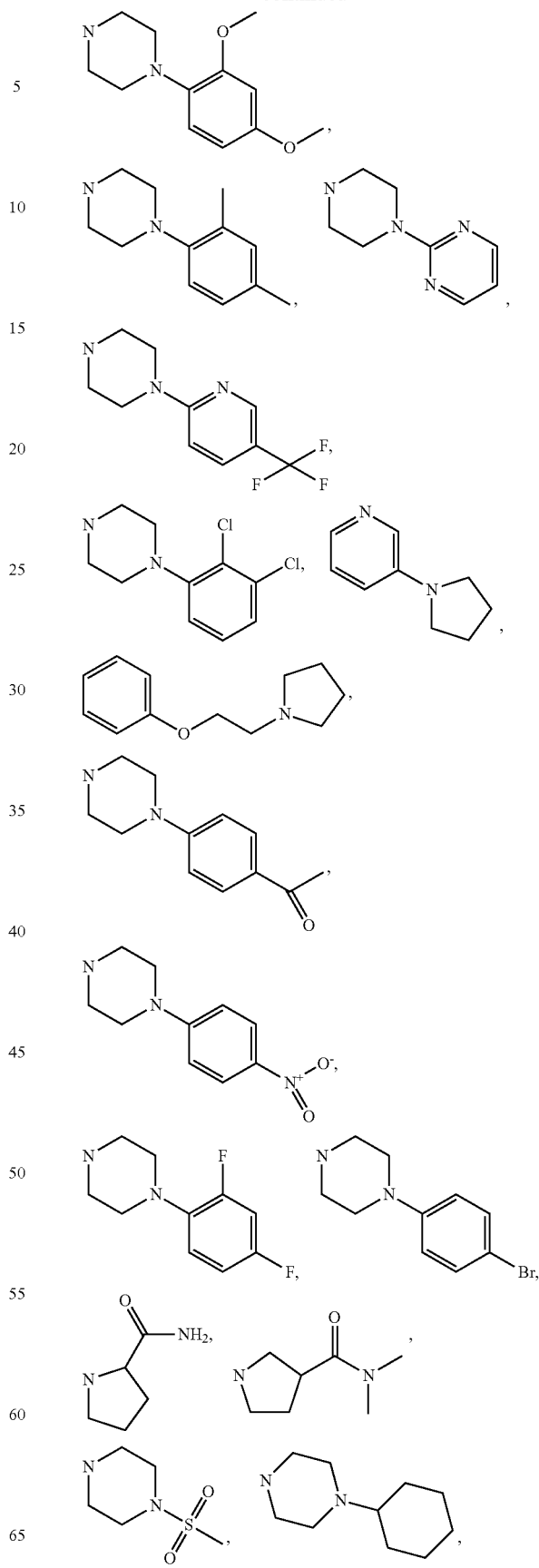

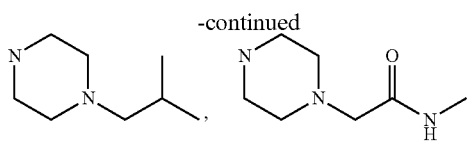

and the like.

Numerical ranges, as used herein, are intended to include sequential whole numbers. For example, a range expressed as "from 0 to 4" would include 0, 1, 2, 3 and 4.

As used herein, the term "substituted" means that the specified group or moiety bears one or more suitable substituents.

As used herein, the term "unsubstituted" means that the specified group bears no substituents.

As used herein, the term "optionally substituted" means that the specified group is unsubstituted or substituted by one or more substituents.

When a multifunctional moiety is shown, the point of attachment to the core is indicated by a line. For e.g. (cycloalkyloxy)alkyl- refers to alkyl being the point of attachment to the core while cycloalkyl is attached to alkyl via the oxy group.

The expression "adjunctive chemotherapeutic agent" generally refers to agents which treat, alleviate, relieve, or ameliorate the side effects of chemotherapeutic agents. Such agents include those which modify blood cell growth and maturation. Examples of adjunctive chemotherapeutic agents include, but are not limited to, filgrastim and erythropoietin. Other such adjunctive chemotherapeutic agents include those which inhibit nausea associated with administration of the chemotherapeutic agents, such as a 5-HT$_3$ receptor inhibitor (e.g., dolansetron, granisetron, or ondansetron), with or without dexamethasone.

The terms "chemotherapeutic agent" and "antineoplastic agent" generally refer to agents which treat, prevent, cure, heal, alleviate, relieve, alter, remedy, ameliorate, improve, or affect malignancies and their metastasis. Examples of such agents (also known as "antineoplastic agents") include, but are not limited to, prednisone, fluorouracil (e.g., 5-fluorouracil (5-FU)), anastrozole, bicalutamide, carboplatin, cisplatin, chlorambucil, cisplatin, carboplatin, docetaxel, doxorubicin, flutamide, interferon-alpha, letrozole, leuprolide, megestrol, mitomycin, oxaliplatin, paclitaxel, plicamycin (Mithracin™), tamoxifen, thiotepa, topotecan, valrubicin, vinvlastin, vincristine, and any combination of any of the foregoing. Additional such agents are described later.

"Nicotinamide phosphoribosyltransferase" also named NAMPT, NMPRT, NMPRTase or NAmPRTase, (International nomenclature: E.C. 2.4.2.12) is a key enzyme in nicotinamide adenyl dinucleotide (NAD) biosynthesis from the natural precursor nicotinamide.

It must be noted that, as used in the specification and the appended claims, the singular forms "a," "an" and "the" include plural referents unless the context clearly dictates otherwise.

When used as a therapeutic agent the inhibitors of the formation of nicotinamide phosphoribosyltransferase (NAMPT) described herein may be administered with one or more physiologically acceptable excipients. A physiologically acceptable carrier or excipient is a formulation to which the compound can be added to dissolve it or otherwise facilitate its administration.

The dosage forms of the present invention, may contain a mixture of one or more compounds of this invention, and may include additional materials known to those skilled in the art as pharmaceutical excipients. Such pharmaceutical excipients include, for example, the following: Stabilizing additives may be incorporated into the delivery agent solution. With some drugs, the presence of such additives promotes the stability and dispersibility of the agent in solution. The stabilizing additives may be employed at a concentration ranging from about 0.1 and 5% (W/V), preferably about 0.5% (W/V). Suitable, but non-limiting, examples of stabilizing additives include gum acacia, gelatin, methyl cellulose, polyethylene glycol, carboxylic acids and salts thereof, and polylysine. The preferred stabilizing additives are gum acacia, gelatin and methyl cellulose.

Acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); Aerosol propellants (butane, dichlorodifluoro-methane, dichlorotetrafluoroethane, isobutane, propane, trichloromonofluoromethane); Air displacements (carbon dioxide, nitrogen); Alcohol denaturants (denatonium benzoate, methyl isobutyl ketone, sucrose octacetate); Alkalizing agents (strong ammonia solution, ammonium carbonate, diethanolamine, diisopropanolamine, potassium hydroxide, sodium bicarbonate, sodium borate, sodium carbonate, sodium hydroxide, trolamine); Anticaking agents (see glidant); Antifoaming agents (dimethicone, simethicone); Antimicrobial preservatives (benzalkonium chloride, benzalkonium chloride solution, benzelthonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol); Antioxidants (ascorbic acid, acorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient); Buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate); Capsule lubricants (see tablet and capsule lubricant); Chelating agents (edetate disodium, ethylenediaminetetraacetic acid and salts, edetic acid); Coating agents (sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyethylene glycol, polyvinyl acetate phthalate, shellac, sucrose, titanium dioxide, carnauba wax, microcrystalline wax, zein); Colorants (caramel, red, yellow, black or blends, ferric oxide); Complexing agents (ethylenediaminetetraacetic acid and salts (EDTA), edetic acid, gentisic acid ethanolmaide, oxyquinoline sulfate); Desiccants (calcium chloride, calcium sulfate, silicon dioxide); Emulsifying and/or solubilizing agents (acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 caster oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, soritan monooleate, sorbitan monopalmitate, sorbitan monostearate, stearic acid, trolamine, emulsifying wax); Filtering aids (powdered cellulose, purified siliceous earth); Flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); Glidants and/or anticaking agents (calcium silicate, magnesium silicate, colloidal silicon dioxide, talc); Humectants (glycerin, hexylene glycol, propylene glycol, sorbitol); Plasticizers (castor oil, diacetylated monoglycerides, diethyl phthalate, glycerin, mono- and di-acetylated monoglycerides, polyethylene glycol, propylene glycol, triacetin, triethyl citrate); Polymers (e.g., cellulose acetate, alkyl celloloses, hydroxyalkylcelloloses, acrylic polymers and copolymers); Solvents (acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil, water for injection, sterile water for injection, sterile water for irrigation, purified water); Sorbents (powdered cellulose, charcoal, purified siliceous earth); Carbon dioxide sorbents (barium hydroxide lime, soda lime); Stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); Suspending and/or viscosity-increasing agents (acacia, agar, alginic acid, aluminum monostearate, bentonite, purified bentonite, magma bentonite, carbomer 934p, carboxymethylcellulose calcium, carboxymethylcellulose sodium, carboxymethycellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, xanthan gum); Sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); Tablet binders (acacia, alginic acid, sodium carboxymethylcellulose, microcrystalline cellulose, dextrin, ethylcellulose, gelatin, liquid glucose, guar gum, hydroxypropyl methylcellulose, methycellulose, polyethylene oxide, povidone, pregelatinized starch, syrup); Tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); Tablet disintegrants (alginic acid, microcrystalline cellulose, croscarmellose sodium, corspovidone, polacrilin potassium, sodium starch glycolate, starch, pregelatinized starch); Tablet and/or capsule lubricants (calcium stearate, glyceryl behenate, magnesium stearate, light mineral oil, polyethylene glycol, sodium stearyl fumarate, stearic acid, purified stearic acid, talc, hydrogenated vegetable oil, zinc stearate); Tonicity agent (dextrose, glycerin, mannitol, potassium chloride, sodium chloride); Vehicle: flavored and/or sweetened (aromatic elixir, compound benzaldehyde elixir, iso-alcoholic elixir, peppermint water, sorbitol solution, syrup, tolu balsam syrup); Vehicle: oleaginous (almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, sesame oil, soybean oil, squalane); Vehicle: solid carrier (sugar spheres); Vehicle: sterile (bacteriostatic water for injection, bacteriostatic sodium chloride injection); Viscosity-increasing (see suspending agent); Water repelling agent (cyclomethicone, dimethicone, simethicone); and Wetting and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaureate, sorbitan monooleate, sorbitan monopalmitate, sorbitan monostearate, tyloxapol). This list is not meant to be exclusive, but instead merely representative of the classes of excipients and the particular excipients which may be used in dosage forms of the present invention.

The compounds of the invention can form salts which are also within the scope of this invention. Reference to a compound of the invention herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of the Formula contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula may be formed, for example, by reacting a compound of Formula with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of the invention, and salts, solvates, esters and prodrugs thereof, may exist in their tautomeric form (for example, as an amide or imino ether). All such tautomeric forms are contemplated herein as part of the present invention.

The compounds of the invention may contain asymmetric or chiral centers, and, therefore, exist in different stereoisomeric forms. It is intended that all stereoisomeric forms of the compounds of the disclosed Formulas as well as mixtures thereof, including racemic mixtures, form part of the present invention. In addition, the present invention embraces all geometric and positional isomers. For example, if a compound of a disclosed Formula incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral HPLC column.

It is also possible that the compounds of the invention may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of the invention incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Certain isotopically-labelled compounds of the invention (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of the disclosed Formulas can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of the disclosed Formulas, and of the salts, solvates, esters and prodrugs of the compounds of the disclosed Formulas, are intended to be included in the present invention.

Benefits of the present invention include oral administration of an optimal amount of a nicotinamide phosphoribosyltransferase biosynthesis inhibitor.

Benefits of the present invention include intravenous administration of an optimal amount of a nicotinamide phosphoribosyltransferase biosynthesis inhibitor.

Benefits of the present invention include intraperitoneal administration of an optimal amount of a nicotinamide phosphoribosyltransferase biosynthesis inhibitor.

Benefits of the present invention include intramural administration of an optimal amount of a nicotinamide phosphoribosyltransferase biosynthesis inhibitor.

Benefits of the present invention include intramuscular administration of an optimal amount of a nicotinamide phosphoribosyltransferase biosynthesis inhibitor.

Benefits of the present invention include subcutaneous administration of an optimal amount of a nicotinamide phosphoribosyltransferase biosynthesis inhibitor.

Benefits of the present invention include intra-tumor administration of an optimal amount of a nicotinamide phosphoribosyltransferase biosynthesis inhibitor.

Benefits of the present invention include intrathecal administration of an optimal amount of a nicotinamide phosphoribosyltransferase biosynthesis inhibitor.

Benefits of the present invention include subdural administration of an optimal amount of a nicotinamide phosphoribosyltransferase biosynthesis inhibitor.

Benefits of the present invention include periorbital administration of an optimal amount of a nicotinamide phosphoribosyltransferase biosynthesis inhibitor.

Based on these results, the present invention has important implications for the design of novel treatment strategies for patients with cancer, including leukemias and solid tumors, inflammatory diseases, osteoporosis, atherosclerosis; irritable bowel syndrome and other conditions disclosed herein or that are known to those skilled in the art.

DESCRIPTION OF CERTAIN EMBODIMENTS

An aspect of the present invention concerns compounds disclosed herein.

An aspect of the present invention concerns compounds which are or can be inhibitors of the formation of nicotinamide phosphoribosyltransferase.

An aspect of the present invention concerns the use of an inhibitor of the formation of nicotinamide phosphoribosyltransferase for the preparation of a medicament used in the treatment, prevention, inhibition or elimination of tumors.

An aspect of the present invention concerns the use of an inhibitor of the formation of nicotinamide phosphoribosyltransferase for the preparation of a medicament used in the treatment, prevention, inhibition or elimination of cancer.

An aspect of the present invention concerns the use of an inhibitor of the formation of nicotinamide phosphoribosyltransferase for the preparation of a medicament used in the treatment, prevention, inhibition or elimination of cancer, where the cancer is selected from leukemia, lymphoma, ovarian cancer, breast cancer, uterine cancer, colon cancer, cervical cancer, lung cancer, prostate cancer, skin cancer, CNS cancer, bladder cancer, pancreatic cancer and Hodgkin's disease.

The present invention also describes one or more methods of synthesizing the compounds of the present invention.

The invention also describes one or more uses of the compounds of the present invention.

The invention also describes one or more uses of the compounds of the present invention with an adjunctive agent such as use with TNF, GCSF, or other chemotherapeutic agents The invention also describes one or more uses of the pharmaceutical compositions of the present invention.

An aspect of the present invention concerns the use as an inhibitor of the formation of nicotinamide phosphoribosyltransferase for the preparation of a medicament used in the treatment of inflammatory diseases.

An aspect of the present invention concerns the use as an inhibitor of the formation of nicotinamide phosphoribosyltransferase for the preparation of a medicament used in the treatment of inflammatory diseases, such as Irritable Bowel Syndrome or Inflammatory Bowel Disease.

An aspect of the present invention concerns the use as an inhibitor of the formation of nicotinamide phosphoribosyltransferase for the preparation of a medicament used in the treatment of disease of the bone such as osteoporosis.

An aspect of the present invention concerns the use as an inhibitor of the formation of nicotinamide phosphoribosyltransferase for the preparation of a medicament used in the treatment of disease of the cardiovascular system, such as atherosclerosis.

An aspect of the present invention concerns the use as an inhibitor of the formation of nicotinamide phosphoribosyltransferase for the preparation of a medicament used in the treatment of disease or a condition caused by an elevated level of NAMPT.

Such disease or condition is one or more selected from the group consisting of cancer, ovarian cancer, breast cancer, uterine cancer, colon cancer, cervical cancer, lung cancer, prostate cancer, skin cancer, bladder cancer, pancreatic cancer, leukemia, lymphoma, Hodgkin's disease, viral infections, Human Immunodeficiency Virus, hepatitis virus, herpes virus, herpes simplex, inflammatory disorders, irritable bowel syndrome, inflammatory bowel disease, rheumatoid arthritis, asthma, chronic obstructive pulmonary disease, osteoarthritis, osteoporosis, dermatitis, atoptic dermatitis, psoriasis, systemic lupus erythematosis, multiple sclerosis, psoriatic arthritis, ankylosing spodylitis, graft-versus-host disease, Alzheimer's disease, cerebrovascular accident, atherosclerosis, diabetes, glomerulonephiritis, metabolic syndrome, non-small cell lung cancer, small cell lung cancer, multiple myeloma, leukemias, lymphomas, squamous cell cancers, kidney cancer, uretral and bladder cancers, cancers of head and neck, cancers of the brain and central nervous system (CNS).

The inventive compounds of can be useful in the therapy of proliferative diseases such as cancer, autoimmune diseases, viral diseases, fungal diseases, neurological/neurodegenerative disorders, arthritis, inflammation, anti-proliferative (e.g., ocular retinopathy), neuronal, alopecia and cardiovascular disease.

More specifically, the compounds can be useful in the treatment of a variety of cancers, including (but not limited to) the following: carcinoma, including that of the bladder, breast, colon, kidney, liver, lung, including small cell lung cancer, non-small cell lung cancer, head and neck, esophagus, gall bladder, ovary, pancreas, stomach, cervix, thyroid, prostate, and skin, including squamous cell carcinoma; hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma, and Burkett's lymphoma; hematopoietic tumors of myeloid lineage, including acute and chronic myelogenous leukemias, myelodysplastic syndrome and promyelocytic leukemia;

tumors of mesenchymal origin, including fibrosarcoma and rhabdomyosarcoma; tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

The compounds of the invention may induce or inhibit apoptosis.

The compounds of the invention may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

A further aspect of the invention is a method of inhibiting a NAMPT pathway in an animal, said method comprising administering to said animal a pharmaceutically acceptable amount of a compound of the invention to an animal in need thereof.

A further aspect of the invention is a pharmaceutical formulation comprising a compound of the invention.

Another embodiment of the invention comprises a pharmaceutical formulation of the invention, wherein the pharmaceutical formulation, upon administration to a human, results in a decrease in tumor burden.

Still another embodiment of the invention is a pharmaceutical formulation, further comprising one or more of an antineoplastic agent, a chemotherapeutic agent, or an adjunctive chemotherapeutic agent.

The pharmaceutical formulations of the invention may further comprise a therapeutic effective amount of an adjunctive chemotherapeutic agent.

The adjunctive chemotherapeutic agent may be an agent which modifies blood cell growth and maturation. Non-limiting examples of adjunctive chemotherapeutic agent are filgrastim, pegfilgrastim and erythropoietin.

The invention is also directed to a method of treating or preventing a disorder associated with excessive rate of growth of cells in a mammal comprising administering to the mammal an effective amount of the pharmaceutical formulation of the invention. Non-limiting examples of disorder include cancer or metastasis from malignant tumors.

Another aspect of the invention is a method of inhibiting tumor cell growth and rate of division in a mammal with cancer, or other disorder associated with abnormally dividing cells comprising administering to the mammal an effective amount of the pharmaceutical formulation of this invention.

Another embodiment of the invention is a method of treating bone pain due to excessive growth of a tumor or metastasis to bone in a mammal in need thereof comprising administering to the mammal an effective amount of the pharmaceutical formulation of this invention.

Still another embodiment of the invention is a method for administering a NAMPT-inhibitor-containing compound to a mammal in need thereof comprising administering to the mammal the pharmaceutical formulation of the invention. In one embodiment, the mammal is a human.

A further embodiment of the invention is a method of preparing a pharmaceutical formulation comprising mixing at least one pharmaceutically acceptable compound of the present invention, and, optionally, one or more pharmaceutically acceptable excipients or additives.

An aspect of the invention is pharmaceutical compositions comprising a compound according to the invention with a cell rescuing agent.

Another aspect of the invention is pharmaceutical compositions comprising a compound according to the invention and a cell rescuing agent selected from the group consisting of nicotinamide, nicotinic acid and nicotinamide mononucleotide (NMN).

The invention is also directed to methods of synthesizing compounds of the present invention.

Compounds of the Invention

The invention is directed to compounds as described herein and pharmaceutically acceptable salts, solvates, esters, prodrugs or isomers thereof, and pharmaceutical compositions comprising one or more compounds as described herein. The invention further relates to molecules which are useful in inhibiting the enzyme nicotinamide phosphoribosyltransferase (NAMPT) and pharmaceutically acceptable salts or isomers thereof.

One aspect of this invention is the provision of compounds, compositions, kits, and antidotes for the NAMPT pathway in mammals having a compound of the Formula I:

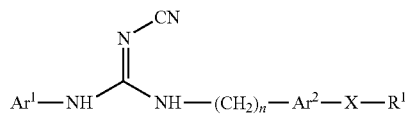

I wherein
Ar$^1$ is aryl, heteroaryl, arylalkyl or heteroarylalkyl, wherein the heteroatom of each of said heteroaryl and heteroaryl independently numbers 1, 2 or 3, and is independently selected from N, S or O, further wherein each of said aryl, heteroaryl, arylalkyl and heteroarylalkyl may optionally independently be either substituted or fused with aryl or heteroaryl, still further wherein any of said aryl, heteroaryl, arylalkyl and heteroarylalkyl is either unsubstituted or optionally independently substituted with one or more substituents which can be the same or different and are independently selected from the group consisting of deuterium, halo, cyano, amino, aminoalkyl-, (amino) alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, alkyl, alkenyl, alkynyl, alkoxy-, -aryloxy-, (alkoxyalkyl)oxy-, (alkoxyalkyl)amino-, -cycloalkyl, -heterocycloalkyl, -aryl, —C(O)-alkyl, —C(O)-aryl, —S(O)-aryl, —NH—C(O)-alkyl, —NH—C(O)-aryl and heteroaryl, with the proviso that no two adjacent ring heteroatoms on a ring are both S or both O;
n is 0, 1, 2, 3 or 4;
Ar$^2$ is aryl or heteroaryl, with each of said aryl and heteroaryl being either unsubstituted or optionally independently with 1, 2, 3 or 4 substituents which can be the same or different and are independently selected from the group consisting of deuterium, halo, cyano, amino, aminoalkyl-, (amino)alkoxy-, —CONH$_2$, —C(O) NH(alkyl), —C(O)N(alkyl)$_2$, —C(O)NH(aryl), —C(O)N (aryl)$_2$, —CH$_z$F$_{3-z}$, —OCH$_z$F$_{3-z}$, alkyl, alkenyl, alkynyl, alkoxy-, -aryloxy-, (alkoxyalkyl)oxy-, (alkoxyalkyl) amino-, -cycloalkyl, -heterocycloalkyl, -aryl, —C(O)-alkyl, —C(O)-aryl, —S(O)-aryl, —NH—C(O)-alkyl, —NH—C(O)-aryl and heteroaryl, with the proviso that no two adjacent ring heteroatoms on a ring are both S or both O;
X is S, S(O), S(O)$_2$, O or C(O);
R$^1$ is cycloalkyl, —CH$_z$F$_{3-z}$, aryl, heterocycloalkyl, heteroaryl, alkyl, alkenyl, alkynyl, (aryl)alkyl-, (heteroaryl) alkyl- or (heterocycloalkyl)alkyl-, (i) wherein each of said cycloalkyl, aryl, heterocycloalkyl, heteroaryl and alkyl is either unsubstituted or optionally independently substituted with 1, 2, 3, 4 or 5 substituents which can be the same or different and are independently selected from the group consisting of deuterium, halo, cyano, amino, aminoalkyl-, (amino)alkoxy-, —CONH$_2$, —C(O)NH (alkyl), —C(O)N(alkyl)$_2$, —C(O)NH(aryl), —C(O)N (aryl)$_2$, —CH$_z$F$_{3-z}$, —OCH$_z$F$_{3-z}$, alkyl, alkenyl, alkynyl, alkoxy-, aryloxy-, (alkoxyalkyl)amino-, -cycloalkyl, -heterocycloalkyl, -aryl, —S(O)$_2$-alkyl, —S(O)$_2$-aryl, —S(O)$_2$—CF$_3$, —C(O)N(alkyl)$_2$, —C(O)alkyl, —NH—C(O)-alkyl, —NH—C(O)-aryl, methylenedioxy, heteroaryl, arylalkyl-, (heteroaryl)alkyl-, and (heterocycloalkyl)alkyl-, (ii) further wherein each of said cycloalkyl, aryl, heterocycloalkyl, and heteroaryl may additionally be fused with independently selected aryl, heteroaryl, heterocycloalkyl or cycloalkyl; and z is 0, 1 or 2;
and pharmaceutically acceptable salts, solvates, esters, prodrugs or isomers thereof.

The following embodiments are directed to Formula I, as applicable. For any moieties that are not specifically defined, the previous definitions control. Further, the moieties aryl, heteroaryl, and heterocycloalkyl in these embodiments can be independently unsubstituted or optionally substituted or optionally fused as described earlier. Any one or more of the embodiments relating to Formula I below can be combined with one or more other embodiments for Formula I.

An embodiment of the invention is the provision of a compound of Formula I, where the various moieties are independently selected, $Ar^1$ is aryl, and n, z, X, $Ar^2$ and $R^1$ are as defined.

An embodiment of the invention is the provision of a compound of Formula I, where the various moieties are independently selected, $Ar^1$ is heteroaryl, and n, z, X, $Ar^2$ and $R^1$ are as defined.

An embodiment of the invention is the provision of a compound of Formula I, where the various moieties are independently selected, $Ar^1$ is (heteroaryl)alkyl-, and n, z, X, $Ar^2$ and $R^1$ are as defined.

An embodiment of the invention is the provision of a compound of Formula I d, where the various moieties are independently selected, $Ar^1$ is arylalkyl-, and n, z, X, $Ar^2$ and $R^1$ are as defined.

An embodiment of the invention is the provision of a compound, where the various moieties are independently selected, $Ar^1$, n, z, $Ar^2$ and $R^1$ are as defined and X is S.

An embodiment of the invention is the provision of a compound of Formula I, where the various moieties are independently selected, $Ar^1$, n, z, $Ar^2$ and $R^1$ are as defined and X is S(O).

An embodiment of the invention is the provision of a compound of Formula I, where the various moieties are independently selected, $Ar^1$, n, z, $Ar^2$ and $R^1$ are as defined and X is $S(O_2)$.

An embodiment of the invention is the provision of a compound of Formula I, where the various moieties are independently selected, $Ar^1$, n, z, $Ar^2$ and $R^1$ are as defined and X is O.

An embodiment of the invention is the provision of a compound of Formula I, where the various moieties are independently selected, $Ar^1$, n, z, $Ar^2$ and $R^1$ are as defined and X is C(O).

An embodiment of the invention is the provision of a compound of Formula I, where the various moieties are independently selected, $Ar^1$, z, X, $Ar^2$ and $R^1$ are as defined and n is 1.

An embodiment of the invention is the provision of a compound of Formula I, where the various moieties are independently selected, $Ar^1$, z, X, $Ar^2$ and $R^1$ are as defined and n is 2.

An embodiment of the invention is the provision of a compound of Formula I, where the various moieties are independently selected, $Ar^1$ is aryl, and n, X, $Ar^2$ and $R^1$ are as defined and z is 0.

An embodiment of the invention is the provision of a compound of Formula I, where the various moieties are independently selected, $Ar^1$ is aryl, and n, X, $Ar^2$ and $R^1$ are as defined and z is 1.

An embodiment of the invention is the provision of a compound of Formula I, where the various moieties are independently selected, $Ar^1$ is aryl, and n, X, $Ar^2$ and $R^1$ are as defined and z is 2.

An embodiment of the invention is the provision of a compound of Formula I, where the various moieties are independently selected, $Ar^1$, n, z, X and $R^1$ are as defined and $Ar^2$ is aryl.

An embodiment of the invention is the provision of a compound of Formula I, where the various moieties are independently selected, $Ar^1$, n, z, X and $R^1$ are as defined and $Ar^2$ is heteroaryl.

An embodiment of the invention is the provision of a compound of Formula I, where the various moieties are independently selected, $Ar^1$, n, z, X and $Ar^2$ are as defined and $R^1$ is aryl.

An embodiment of the invention is the provision of a compound of Formula I, where the various moieties are independently selected, $Ar^1$, n, z, X and $Ar^2$ are as defined and $R^1$ is heteroaryl.

An embodiment of the invention is the provision of a compound of Formula I, where the various moieties are independently selected, $Ar^1$, n, z, X and $Ar^2$ are as defined and $R^1$ is arylalkyl.

An embodiment of the invention is the provision of a compound of Formula I, where the various moieties are independently selected, $Ar^1$, n, z, X and $Ar^2$ are as defined and $R^1$ is (heteroaryl)alkyl.

An embodiment of the invention is the provision of a compound of Formula I, where the various moieties are independently selected, $Ar^1$, n, z, X and $Ar^2$ are as defined and $R^1$ is heterocycloalkyl.

An embodiment of the invention is the provision of a compound of Formula I, where the various moieties are independently selected, $Ar^1$, n, z, X and $Ar^2$ are as defined and $R^1$ is (heterocycloalkyl)alkyl-.

An embodiment of the invention is the provision of a compound of Formula I, where the various moieties are independently selected, $Ar^1$ is phenyl, and n, z, X, $Ar^2$ and $R^1$ are as defined.

An embodiment of the invention is the provision of a compound of Formula I, where the various moieties are independently selected, $Ar^1$ is pyridyl, and n, z, X, $Ar^2$ and $R^1$ are as defined.

An embodiment of the invention is the provision of a compound of Formula I, where the various moieties are independently selected, $Ar^1$ is pyridylmethyl-, and n, z, X, $Ar^2$ and $R^1$ are as defined.

An embodiment of the invention is the provision of a compound of Formula I, where the various moieties are independently selected, $Ar^1$ is imidazopyridyl-, and n, z, X, $Ar^2$ and $R^1$ are as defined.

An embodiment of the invention is the provision of a compound of Formula I, where the various moieties are independently selected, $Ar^1$ is (imidazopyridyl)methyl-, and n, z, X, $Ar^2$ and $R^1$ are as defined.

An embodiment of the invention is the provision of a compound of Formula I, where the various moieties are independently selected, $Ar^1$ is pyridyl, n, z, $Ar^2$ and $R^1$ are as defined and X is $S(O_2)$.

An embodiment of the invention is the provision of a compound of Formula I, where the various moieties are independently selected, $Ar^1$ is imidazopyridyl, n, z, $Ar^2$ and $R^1$ are as defined and X is $S(O_2)$.

An embodiment of the invention is the provision of a compound of Formula I, where the various moieties are independently selected, $Ar^1$ is pyridylmethyl, n, z, $Ar^2$ and $R^1$ are as defined and X is $S(O_2)$.

An embodiment of the invention is the provision of a compound of Formula I, where the various moieties are independently selected, $Ar^1$ is (imidazopyridyl)methyl, n, z, $Ar^2$ and $R^1$ are as defined and X is $S(O_2)$.

An embodiment of the invention is the provision of a compound of Formula I, where the various moieties are independently selected, $Ar^1$ is pyridyl, z, X, $Ar^2$ and $R^1$ are as defined and n is 1.

An embodiment of the invention is the provision of a compound of Formula I, where the various moieties are independently selected, $Ar^1$ is imidazopyridyl, z, X, $Ar^2$ and $R^1$ are as defined and n is 1.

An embodiment of the invention is the provision of a compound of Formula I, where the various moieties are independently selected, Ar¹ is pyridylmethyl, z, X, Ar² and R¹ are as defined and n is 1.

An embodiment of the invention is the provision of a compound of Formula I, where the various moieties are independently selected, Ar¹ is (imidazopyridyl)methyl-, z, X, Ar² and R¹ are as defined and n is 1.

An embodiment of the invention is the provision of a compound of Formula I, where the various moieties are independently selected, Ar¹ is pyridyl, z, X, and R¹ are as defined, Ar² is aryl, and n is 1.

An embodiment of the invention is the provision of a compound of Formula I, where the various moieties are independently selected, Ar¹ is imidazopyridyl, z, X, and R¹ are as defined, Ar² is aryl, and n is 1.

An embodiment of the invention is the provision of a compound of Formula I, where the various moieties are independently selected, Ar¹ is pyridylmethyl, z, X, and R¹ are as defined, Ar² is aryl, and n is 1.

An embodiment of the invention is the provision of a compound of Formula I, where the various moieties are independently selected, Ar¹ is (imidazopyridyl)methyl, z, X, and R¹ are as defined, Ar² is aryl, and n is 1.

An embodiment of the invention is the provision of a compound of Formula I, where the various moieties are independently selected, Ar¹ is pyridyl, z, and X are as defined, Ar² is aryl, R¹ is aryl, and n is 1.

An embodiment of the invention is the provision of a compound of Formula I, where the various moieties are independently selected, Ar¹ is pyridyl, z, and X are as defined, Ar² is aryl, R¹ is heteroaryl, and n is 1.

An embodiment of the invention is the provision of a compound of Formula I, where the various moieties are independently selected, Ar¹ is pyridyl, z, and X are as defined, Ar² is aryl, R¹ is arylalkyl, and n is 1.

An embodiment of the invention is the provision of a compound of Formula I, where the various moieties are independently selected, Ar¹ is pyridyl, z, and X are as defined, Ar² is aryl, R¹ is heteroarylalkyl-, and n is 1.

An embodiment of the invention is the provision of a compound of Formula I, where the various moieties are independently selected, Ar¹ is pyridyl, z, and X are as defined, Ar² is aryl, R¹ is heterocycloalkyl, and n is 1.

An embodiment of the invention is the provision of a compound of Formula I, where the various moieties are independently selected, Ar¹ is pyridyl, z, and X are as defined, Ar² is aryl, R¹ is (heterocycloalkyl)alkyl-, and n is 1.

An embodiment of the invention is the provision of a compound of Formula I, where the various moieties are independently selected, Ar¹ is pyridyl, z, and X are as defined, Ar² is aryl, R¹ is phenyl, and n is 1.

An embodiment of the invention is the provision of a compound of Formula I, where the various moieties are independently selected, Ar¹ is pyridyl, z, and X are as defined, Ar² is aryl, R¹ is pyridyl, and n is 1.

An embodiment of the invention is the provision of a compound of Formula I, where the various moieties are independently selected, Ar¹ is pyridyl, z, and X are as defined, Ar² is aryl, R¹ is naphthalenyl, and n is 1.

An embodiment of the invention is the provision of a compound of Formula I, where the various moieties are independently selected, Ar¹ is pyridyl, z, and X are as defined, Ar² is aryl, R¹ is quinolyl, and n is 1.

An embodiment of the invention is the provision of a compound of Formula I, where the various moieties are independently selected, Ar¹ is pyridyl, z, and X are as defined, Ar² is aryl, R¹ is isoquinolyl, and n is 1.

An embodiment of the invention is the provision of a compound of Formula I, where the various moieties are independently selected, Ar¹ is pyridyl, z, and X are as defined, Ar² is aryl, R¹ is morpholinyl, and n is 1.

An embodiment of the invention is the provision of a compound of Formula I, where the various moieties are independently selected, Ar¹ is pyridyl, z, and X are as defined, Ar² is aryl, R¹ is morpholinylalkyl, and n is 1.

An embodiment of the invention is the provision of a compound of Formula I, where the various moieties are independently selected, Ar¹ is pyridyl, z, and X are as defined, Ar² is aryl, R¹ is oxaazabicyclooctanyl, and n is 1.

The invention of this disclosure includes any combinations of the various embodiments of compounds of Formula I provided above.

Another embodiment of the invention is compounds of Formula II, which is derived from Formula I where X is SO₂:

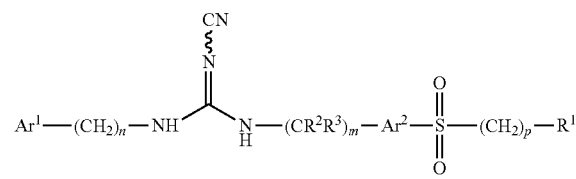

II wherein

Ar¹ is aryl or heteroaryl, wherein said aryl or heteroaryl is unsubstituted or substituted with one or more substituents independently selected from the group consisting of:
  deuterium, halo, cyano, alkyl, cyanoalkyl, haloalkyl, alkenyl, alkynyl, alkoxy, haloalkoxy, aryloxy, —NR$^a$R$^b$, —C(O)N(R$^a$R$^b$), —C(O)-alkyl, —C(O)-aryl, —S(O)-aryl, —NH—C(O)-alkyl, —NH—C(O)-aryl, -(alkoxyalkyl)oxy-, cycloalkyl, heterocycloalkyl, aryl, and heteroaryl;

Ar² is unsubstituted aryl or heteroaryl;

R¹ is cycloalkyl, aryl, heterocycloalkyl, or heteroaryl,
  (i) wherein each of said cycloalkyl, aryl, heterocycloalkyl and heteroaryl is either unsubstituted or optionally independently substituted with 1, 2, 3, 4 or 5 substituents which can be the same or different and are independently selected from the group consisting of:
    deuterium, halo, cyano, alkyl, hydroxyalkyl, cyanoalkyl, haloalkyl, alkenyl, alkynyl, alkoxy, alkylalkoxy, haloalkoxy, aryloxy, —NR$^a$R$^b$, —CONR$^a$R$^b$, —S(O)₂-alkyl, —S(O)₂-aryl, —S(O)₂N(alkyl)₂, —S(O)₂—CF₃, —C(O)alkyl, —NH—C(O)alkyl, —NH—C(O)aryl, methylenedioxy, —(CH₂)$_q$cycloalkyl, —(CH₂)$_q$aryl, —(CH₂)$_q$heteroaryl, and —(CH₂)$_q$heterocycloalkyl,
  (ii) wherein each of said cycloalkyl, aryl, heterocycloalkyl, and heteroaryl may additionally be unsubstituted or substituted by one or more halo, cyano, alkyl or alkoxy or may be fused with independently selected aryl, heteroaryl, heterocycloalkyl or cycloalkyl;

R$^a$ and R$^b$ are independently H, alkyl, alkoxy, aryl, alkoxyalkyl, —S(O)₂alkyl and cycloalkyl or R$^a$ and R$^b$ can form a 5 or 6 membered heterocycloalkyl group together with the nitrogen atom to which they are attached, wherein said heterocycloalkyl group may contain one or more additional heteroatom(s) selected from N, S or O;
$R^2$ and $R^3$ are H or deuterium;
m, n, p and q are independently 0, 1 or 2;
or pharmaceutically acceptable salts thereof.

Another embodiment of the invention is compounds of Formula IIA

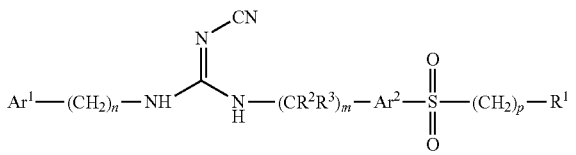

IIA wherein the various moieties are as defined above

Yet another embodiment of the invention is the compounds of Formula IIB:

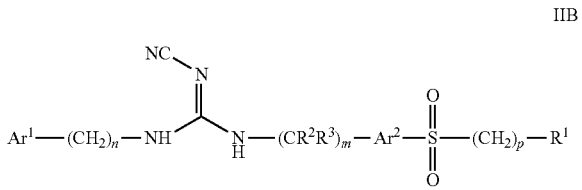

IIB where the various moieties are as defined above.

In the compounds of Formula II, IIA and IIB, the various moieties are independently selected.

The following embodiments are directed to Formulas II, IIA and IIB as applicable. For any moieties that are not specifically defined, the previous definitions control. Further, the moieties aryl, heteroaryl, and heterocycloalkyl in these embodiments can be independently unsubstituted or optionally substituted or optionally fused as described earlier. Any one or more of the embodiments related to to Formulas II, IIA and IIB below can be combined with any one or more other embodiments of Formulas II, IIA and IIB.

An embodiment of the invention is the provision of a compound of Formula II, IIA or IIB, where the various moieties are independently selected, and $Ar^1$ is aryl.

An embodiment of the invention is the provision of a compound of Formula II, IIA or IIB, where the various moieties are independently selected, and $Ar^{1-}$ is heteroaryl.

An embodiment of the invention is the provision of a compound of Formula II, IIA or IIB, where the various moieties are independently selected, and $Ar^{1-}$ is unsubstituted heteroaryl.

An embodiment of the invention is the provision of a compound of Formula II, IIA or IIB, where the various moieties are independently selected, and $Ar^{1-}$ is unsubstituted pyridine.

An embodiment of the invention is the provision of a compound of Formula II, IIA or IIB, where the various moieties are independently selected, and $Ar^{1-}$ is substituted pyridine.

An embodiment of the invention is the provision of a compound of Formula II, IIA or IIB, where the various moieties are independently selected, and $Ar^{1-}$ is pyridine substituted with alkyl.

An embodiment of the invention is the provision of a compound of Formula II, IIA or IIB, where the various moieties are independently selected, and $Ar^{1-}$ is 9 or 10 membered bicyclic heteroaryl comprising 1, 2, or 3 heteroatoms selected from N, S, or O with the proviso that no two adjacent ring heteroatoms on the ring are both S or both O.

An embodiment of the invention is the provision of a compound of Formula II, IIA or IIB, where the various moieties are independently selected, $Ar^2$ is phenyl and $Ar^1$ is imidazopyridine.

An embodiment of the invention is the provision of a compound of Formula II, IIA or IIB, where the various moieties are independently selected, and $Ar^{1-}$ is aryl.

An embodiment of the invention is the provision of a compound of Formula II, IIA or IIBG, where the various moieties are independently selected and $Ar^2$ is aryl An embodiment of the invention is the provision of a compound of Formula II, IIA or IIB, where the various moieties are independently selected and $Ar^2$ is phenyl.

An embodiment of the invention is the provision of a compound of Formula II, IIA or IIB, where the various moieties are independently selected, and $Ar^2$ is heteroaryl.

An embodiment of the invention is the provision of a compound of Formula II, IIA or IIB, where the various moieties are independently selected, $Ar^2$ is phenyl and $Ar^1$ is imidazopyridine.

An embodiment of the invention is the provision of a compound of Formula II, IIA or IIB, where the various moieties are independently selected, and $R^1$ is aryl.

An embodiment of the invention is the provision of a compound of Formula II, IIA or IIB, where the various moieties are independently selected, and $R^1$ is unsubstituted phenyl.

An embodiment of the invention is the provision of a compound of Formula II, IIA or IIB, where the various moieties are independently selected, and $R^1$ is phenyl substituted with one or more substituents selected from the group consisting of halo, hydroxyl, cyano, alkyl, alkoxy, haloalkyl, hydroxyalkyl, cyanoalkyl, haloalkoxy, alkylsulfonyl, heterocycloalkyl, —NHsulfonylalkyl, —C(O)alkyl, —C(O)heterocycloalkyl, —C(O)NHalkyl, —C(O)N(alkyl)$_2$, —CO(O)NHcycloalkyl, —C(O)NHheterocycloalkyl, aryl, heteroaryl and heteroaryl optionally substituted by alkyl.

An embodiment of the invention is the provision of a compound, of Formula II, IIA or IIB where the various moieties are independently selected, and $R^1$ is unsubstituted or substituted phenyl, $Ar^2$ unsubstituted aryl and $Ar^1$ is pyridine.

An embodiment of the invention is the provision of a compound of Formula II, IIA or IIB, where the various moieties are independently selected, and $R^1$ is unsubstituted heteroaryl.

An embodiment of the invention is the provision of a compound of Formula II, IIA or IIB, where the various moieties are independently selected, and $R^1$ is heteroaryl substituted by one or more substituents selected from the group consisting of halo, alkyl, alkoxy, heterocycloalkyl, and —N($R^aR^b$), wherein $R^aR^b$ are defined as above.

An embodiment of the invention is the provision of a compound of Formula II, IIA or IIB, where the various moieties are independently selected, and $R^1$ is heteroaryl substituted by one or more substituents selected from the group consisting of halo, alkyl, alkoxy, heterocycloalkyl, and —N($R^aR^b$), and $Ar^2$ unsubstituted aryl and $Ar^1$ is pyridine.

An embodiment of the invention is the provision of a compound of Formula II, IIA or IIB, where the various moieties are independently selected, and $R^{1-}$ is 9 or 10 membered bicyclic heteroaryl comprising 1, 2, or 3 heteroatoms selected from N, S, or O with the proviso that no two adjacent ring heteroatoms on a ring are both S or both O.

An embodiment of the invention is the provision of a compound of Formula II, IIA or IIB, where the various moieties are independently selected, and $R^{1-}$ is 9 or 10 membered bicyclic heteroaryl, where the heteroaryl is selected form the group consisting of pyridine, quinoline, benzodiozole, indazole, and 8-oxa-3-azaicyclo[3.2.1]octane.

An embodiment of the invention is the provision of a compound of Formula II, IIA or IIB, where the various moieties are independently selected, and $R^1$ is 9 or 10 membered bicyclic heteroaryl comprising 1, 2, or 3 heteroatoms selected from N, S, or O with the proviso that no two adjacent ring heteroatoms on a ring are both S or both O, and $Ar^2$ unsubstituted aryl and $Ar^1$ is pyridine.

An embodiment of the invention is the provision of a compound of Formula II, IIA or IIB, where q=0.

An embodiment of the invention is the provision of a compound of Formula II, IIA or IIB, where m=0.

An embodiment of the invention is the provision of a compound of Formula II, IIA or IIB, where n=1

An embodiment of the invention is the provision of a compound of Formula II, IIA or IIB, where p=0.

The invention of this disclosure includes any combinations of the various embodiments of compounds of Formula II, IIA and II B provided above.

In another embodiment, the invention is further illustrated by the compounds shown in Table 2.

TABLE 2

| Structure | Chemical Name |
|---|---|
| 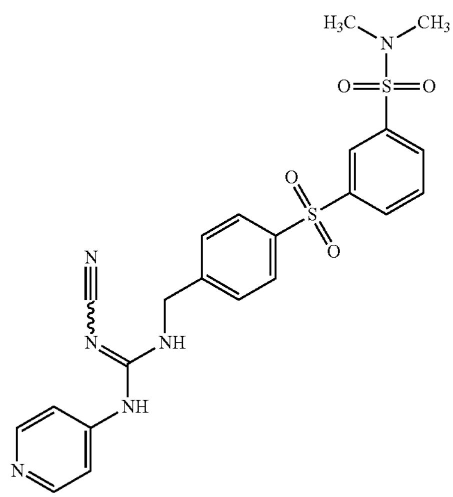 [SMILES: CN(C)S(=O)(=O)c1cccc(S(=O)(=O)c2ccc(CNC(=NC#N)Nc3ccncc3)cc2)c1] | 2-cyano-1-[(4-{[3-(dimethylsulfamoyl)benzene]sulfonyl}phenyl)methyl]-3-(pyridin-4-yl)guanidine |
| 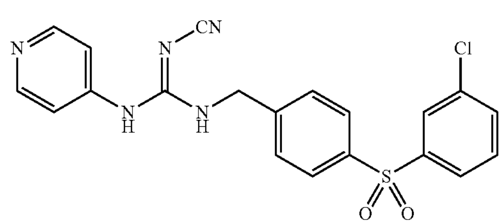 [SMILES: N#C/N=C(\NCc1ccc(S(=O)(=O)c2cccc(Cl)c2)cc1)Nc1ccncc1] | (E)-3-({4-[(3-chlorobenzene)sulfonyl]phenyl}methyl)-2-cyano-1-(pyridin-4-yl)guanidine |
| 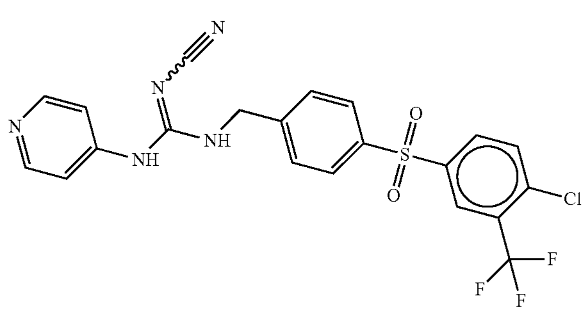 | 1-[(4-{[4-chloro-3-(trifluoromethyl)benzene]sulfonyl}phenyl)methyl]-2-cyano-3-(pyridin-4-yl)guanidine |

TABLE 2-continued

| Structure | Chemical Name |
|---|---|
|  | 2-cyano-3-(pyridin-4-yl)-1-[(4-{[3-(trifluoromethoxy)benzene]sulfonyl}phenyl)methyl]guanidine |
| 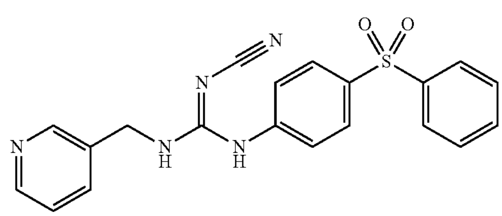 [SMILES: N#C/N=C(/NCc1cccnc1)Nc1ccc(S(=O)(=O)c2ccccc2)cc1] | 1-[4-(benzenesulfonyl)phenyl]-2-cyano-3-(pyridin-3-ylmethyl)guanidine |
|  | 2-cyano-3-(pyridin-4-yl)-1-[(4-{[3-(trifluoromethoxy)benzene]sulfonyl}phenyl)methyl]guanidine |

TABLE 2-continued

| Structure | Chemical Name |
|---|---|
| 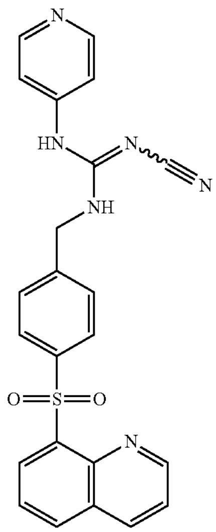 [SMILES: N#CN=C(NCc1ccc(S(=O)(=O)c2cccc3cccnc23)cc1)Nc1ccncc1] | 2-cyano-3-(pyridin-4-yl)-1-{[4-(quinoline-8-sulfonyl)phenyl]methyl}guanidine |
| 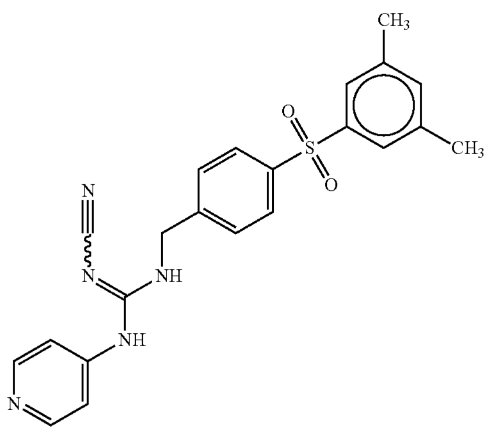 | 2-cyano-1-({4-[(3,5-dimethylbenzene)sulfonyl]phenyl}methyl)-3-(pyridin-4-yl)guanidine |
| 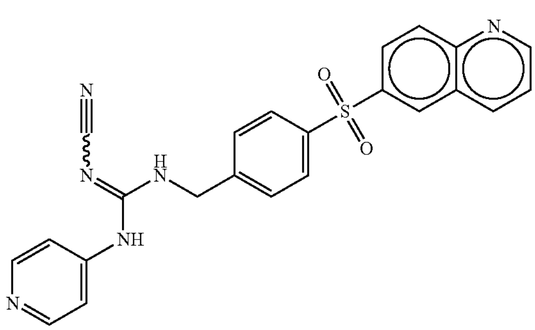 | 2-cyano-3-(pyridin-4-yl)-1-{[4-(quinoline-6-sulfonyl)phenyl]methyl}guanidine |

TABLE 2-continued

| Structure | Chemical Name |
|---|---|
| | 2-cyano-1-[(4-{[2-(morpholin-4-ylmethyl)benzene]sulfonyl}phenyl)methyl]-3-(pyridin-4-yl)guanidine |
| 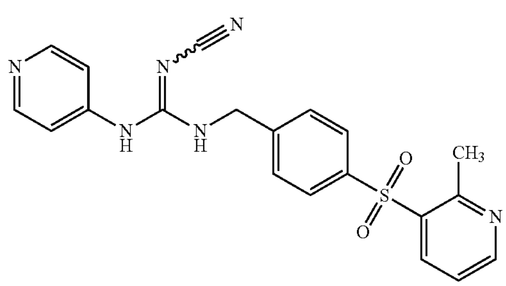 [SMILES: Cc1ncccc1S(=O)(=O)c1ccc(CNC(=NC#N)Nc2ccncc2)cc1] | 2-cyano-1-{[4-(2-methylpyridine-3-sulfonyl)phenyl]methyl}-3-(pyridin-4-yl)guanidine |
| 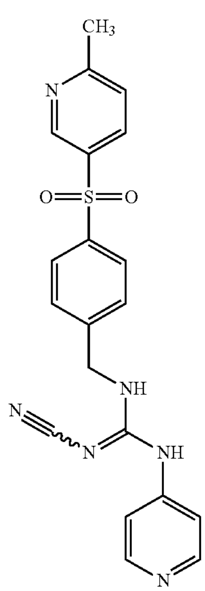 [SMILES: Cc1ccc(S(=O)(=O)c2ccc(CNC(=NC#N)Nc3ccncc3)cc2)cn1] | 2-cyano-1-{[4-(6-methylpyridine-3-sulfonyl)phenyl]methyl}-3-(pyridin-4-yl)guanidine |

TABLE 2-continued

| Structure | Chemical Name |
|---|---|
| 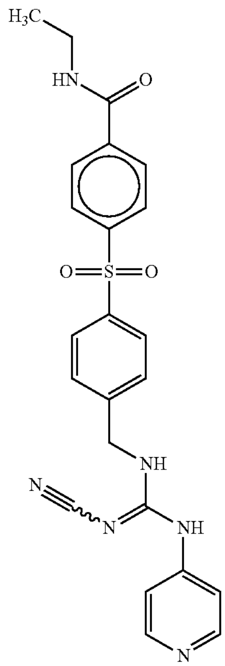 | 4-[(4-{[2-cyano-3-(pyridin-4-yl)carbamimidamido]methyl}benzene)sulfonyl]-N-ethylbenzamide |
| 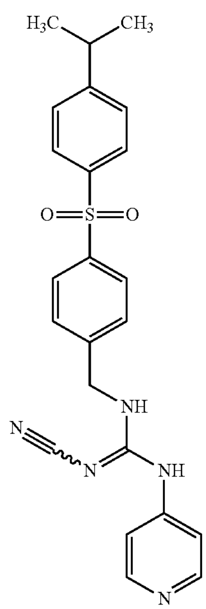 [SMILES: CC(C)c1ccc(S(=O)(=O)c2ccc(CNC(=NC#N)Nc3ccncc3)cc2)cc1] | 2-cyano-1-[(4-{[4-(propan-2-yl)benzene]sulfonyl}phenyl)methyl]-3-(pyridin-4-yl)guanidine |
| 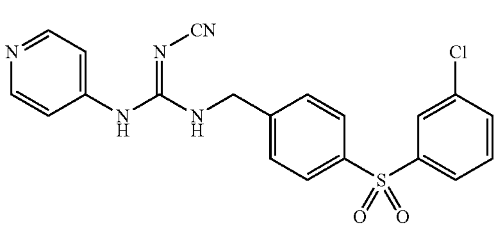 [SMILES: N#C/N=C(\NCc1ccc(S(=O)(=O)c2cccc(Cl)c2)cc1)Nc1ccncc1] | 3-({4-[(3-chlorobenzene)sulfonyl]phenyl}methyl)-2-cyano-1-(pyridin-4-yl)guanidine |

TABLE 2-continued
| Structure | Chemical Name |
|---|---|
| 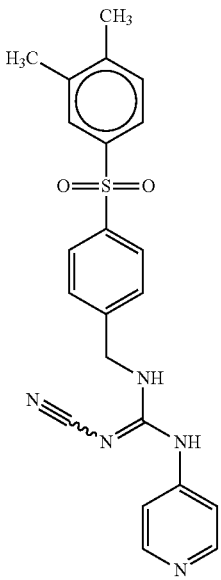 | 2-cyano-1-({4-[(3,4-dimethylbenzene)sulfonyl]phenyl}methyl)-3-(pyridin-4-yl)guanidine |
| 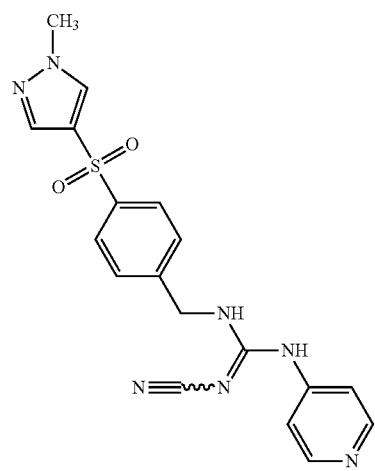 [SMILES: Cn1cc(S(=O)(=O)c2ccc(CNC(=NC#N)Nc3ccncc3)cc2)cn1] | 2-cyano-1-{[4-(1-methyl-1H-pyrazole-4-sulfonyl)phenyl]methyl}-3-(pyridin-4-yl)guanidine |
| 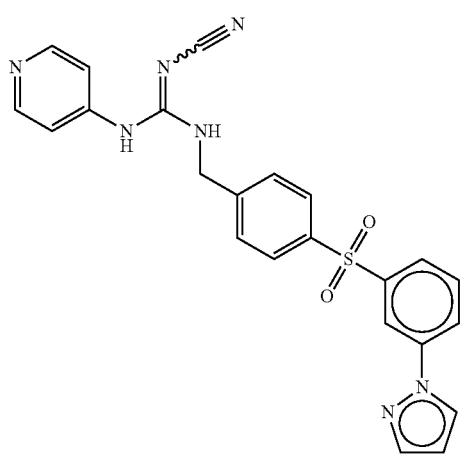 | 2-cyano-1-[(4-{[3-(1H-pyrazol-1-yl)benzene]sulfonyl}phenyl)methyl]-3-(pyridin-4-yl)guanidine |

TABLE 2-continued

| Structure | Chemical Name |
|---|---|
| 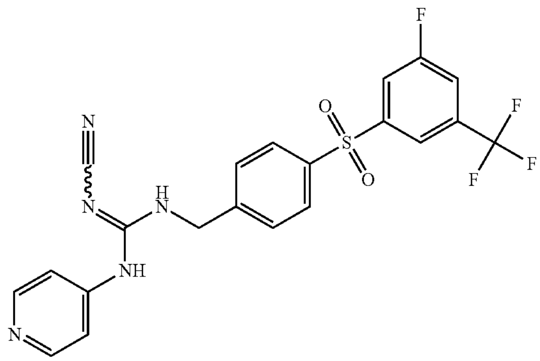 [SMILES: N#CN=C(NCc1ccc(S(=O)(=O)c2cc(F)cc(C(F)(F)F)c2)cc1)Nc1ccncc1] | 2-cyano-1-[(4-{[3-fluoro-5-(trifluoromethyl)benzene]sulfonyl}phenyl)methyl]-3-(pyridin-4-yl)guanidine |
| 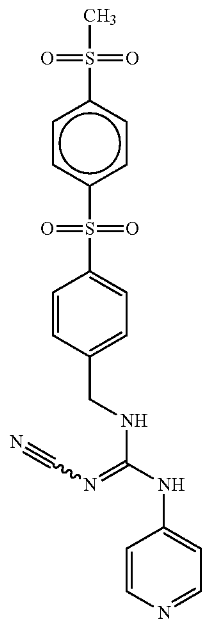 | 2-cyano-1-({4-[(4-methanesulfonylbenzene)sulfonyl]phenyl}methyl)-3-(pyridin-4-yl)guanidine |
| 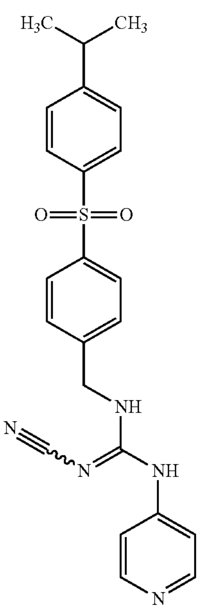 [SMILES: CC(C)c1ccc(S(=O)(=O)c2ccc(CNC(=NC#N)Nc3ccncc3)cc2)cc1] | 2-cyano-1-[(4-{[4-(propan-2-yl)benzene]sulfonyl}phenyl)methyl]-3-(pyridin-4-yl)guanidine |

TABLE 2-continued
| Structure | Chemical Name |
|---|---|
| 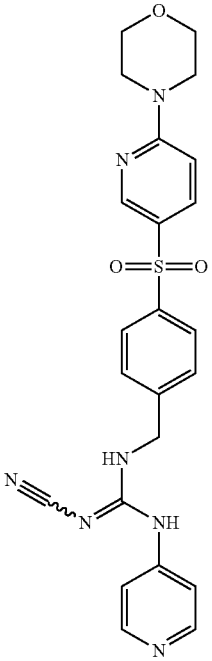 [SMILES: N#CN=C(NCc1ccc(S(=O)(=O)c2ccc(N3CCOCC3)nc2)cc1)Nc1ccncc1] | 2-cyano-1-({4-[6-(morpholin-4-yl)pyridine-3-sulfonyl]phenyl}methyl)-3-(pyridin-4-yl)guanidine |
| 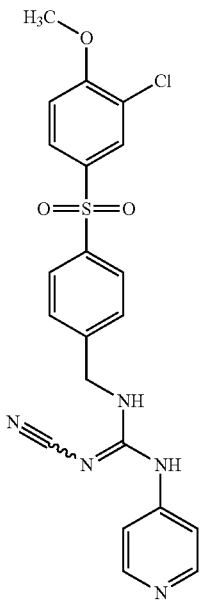 [SMILES: COc1ccc(S(=O)(=O)c2ccc(CNC(=NC#N)Nc3ccncc3)cc2)cc1Cl] | 1-({4-[(3-chloro-4-methoxybenzene)sulfonyl]phenyl}methyl)-2-cyano-3-(pyridin-4-yl)guanidine |

TABLE 2-continued

| Structure | Chemical Name |
|---|---|
| 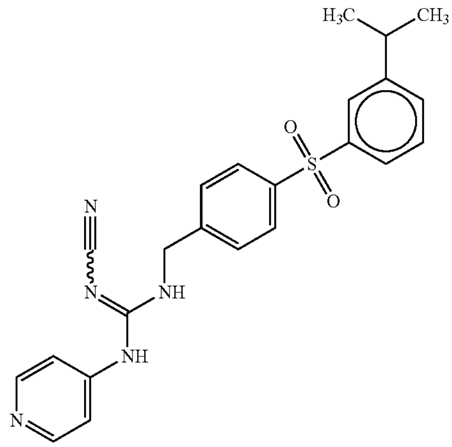 | 2-cyano-1-[(4-{[3-(propan-2-yl)benzene]sulfonyl}phenyl)methyl]-3-(pyridin-4-yl)guanidine |
| 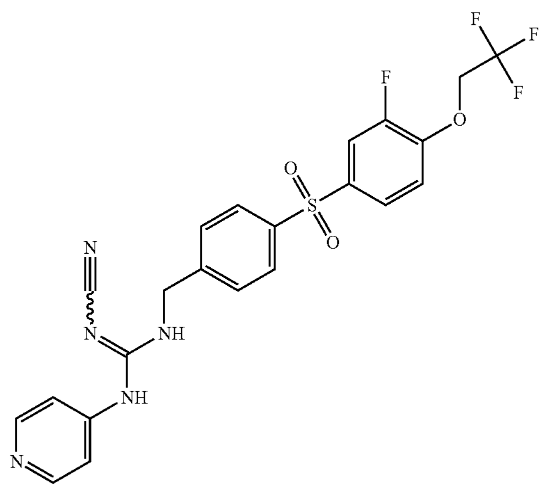 [SMILES: N#CN=C(NCc1ccc(S(=O)(=O)c2ccc(OCC(F)(F)F)c(F)c2)cc1)Nc1ccncc1] | 2-cyano-1-[(4-{[3-fluoro-4-(2,2,2-trifluoroethoxy)benzene]sulfonyl}phenyl)methyl]-3-(pyridin-4-yl)guanidine |
| 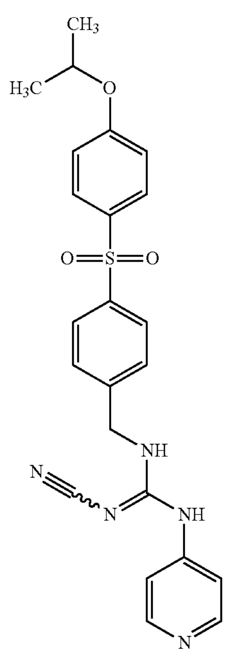 [SMILES: CC(C)Oc1ccc(S(=O)(=O)c2ccc(CNC(=NC#N)Nc3ccncc3)cc2)cc1] | 2-cyano-1-[(4-{[4-(propan-2-yloxy)benzene]sulfonyl}phenyl)methyl]-3-(pyridin-4-yl)guanidine |

TABLE 2-continued

| Structure | Chemical Name |
|---|---|
| 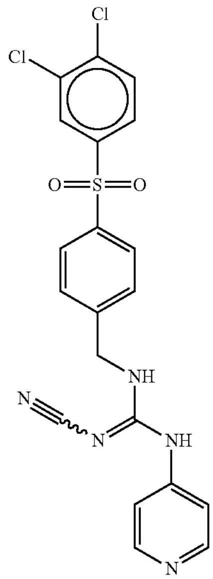 | 2-cyano-1-({4-[(3,4-dichlorobenzene)sulfonyl]phenyl}methyl)-3-(pyridin-4-yl)guanidine |
| 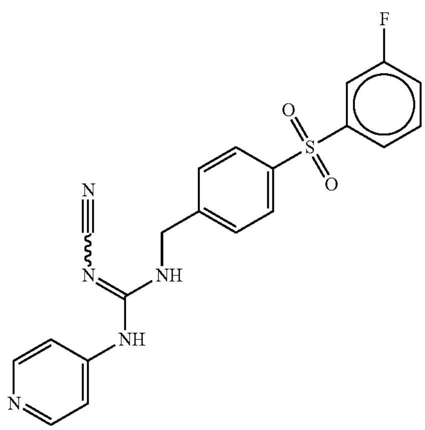 | 2-cyano-1-({4-[(3-fluorobenzene)sulfonyl]phenyl}methyl)-3-(pyridin-4-yl)guanidine |
| 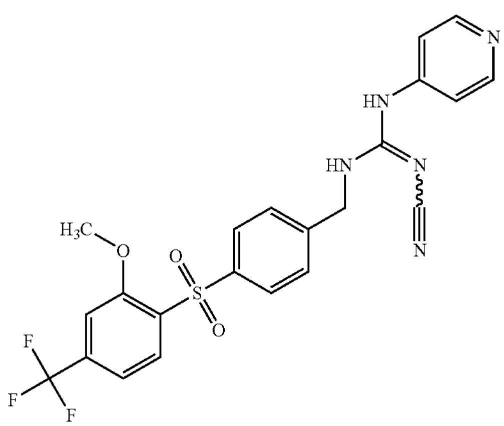 [SMILES: COc1cc(C(F)(F)F)ccc1S(=O)(=O)c1ccc(CNC(=NC#N)Nc2ccncc2)cc1] | 2-cyano-1-[(4-{[2-methoxy-4-(trifluoromethyl)benzene]sulfonyl}phenyl)methyl]-3-(pyridin-4-yl)guanidine |

TABLE 2-continued

| Structure | Chemical Name |
|---|---|
| 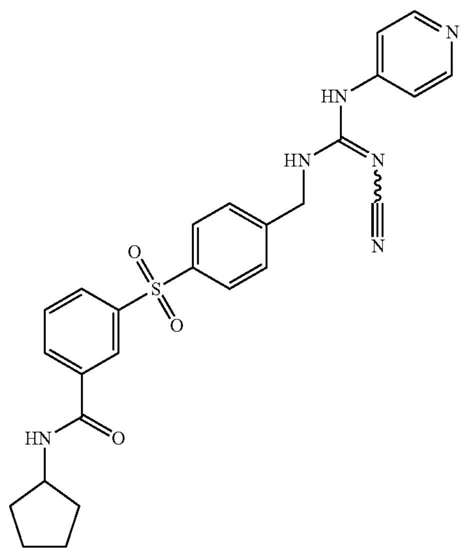 [SMILES: N#CN=C(NCc1ccc(S(=O)(=O)c2cccc(C(=O)NC3CCCC3)c2)cc1)Nc1ccncc1] | 3-[(4-{[2-cyano-3-(pyridin-4-yl)carbamimidamido]methyl}benzene)sulfonyl]-N-cyclopentylbenzamide |
| 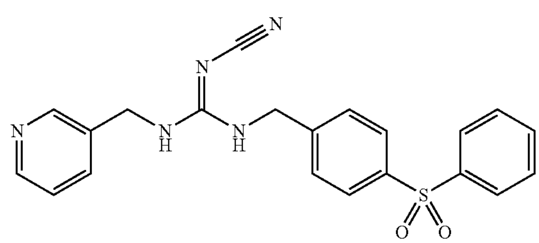 [SMILES: N#C/N=C(\NCc1ccc(S(=O)(=O)c2ccccc2)cc1)NCc1cccnc1] | (E)-3-{[4-(benzenesulfonyl)phenyl]methyl}-2-cyano-1-(pyridin-3-ylmethyl)guanidine |
| 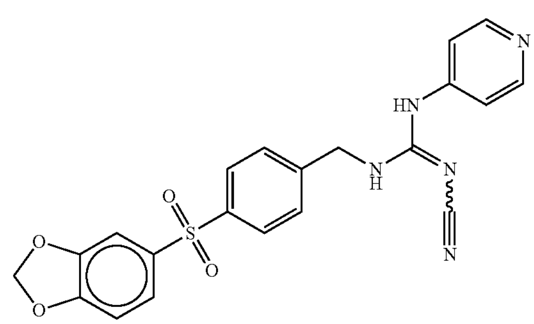 | 1-{[4-(2H-1,3-benzodioxole-5-sulfonyl)phenyl]methyl}-2-cyano-3-(pyridin-4-yl)guanidine |

TABLE 2-continued

| Structure | Chemical Name |
|---|---|
| 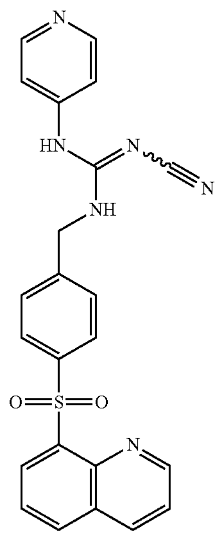 [SMILES: N#CN=C(NCc1ccc(S(=O)(=O)c2cccc3cccnc23)cc1)Nc1ccncc1] | 2-cyano-3-(pyridin-4-yl)-1-{[4-(quinoline-8-sulfonyl)phenyl]methyl}guanidine |
| 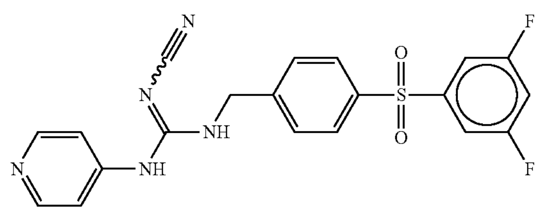 | 2-cyano-1-({4-[(3,5-difluorobenzene)sulfonyl]phenyl}methyl)-3-(pyridin-4-yl)guanidine |
| 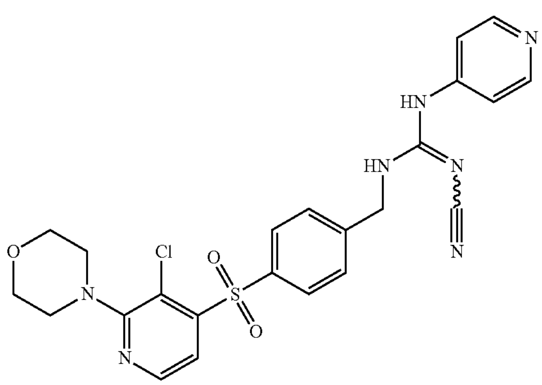 [SMILES: N#CN=C(NCc1ccc(S(=O)(=O)c2ccnc(N3CCOCC3)c2Cl)cc1)Nc1ccncc1] | 1-({4-[3-chloro-2-(morpholin-4-yl)pyridine-4-sulfonyl]phenyl}methyl)-2-cyano-3-(pyridin-4-yl)guanidine |
| 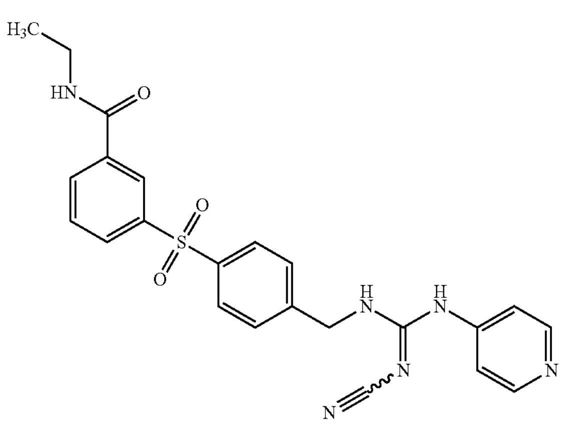 [SMILES: CCNC(=O)c1cccc(S(=O)(=O)c2ccc(CNC(=NC#N)Nc3ccncc3)cc2)c1] | 3-[(4-{[2-cyano-3-(pyridin-4-yl)carbamimidamido]methyl}benzene)sulfonyl]-N-ethylbenzamide |

TABLE 2-continued

| Structure | Chemical Name |
|---|---|
| 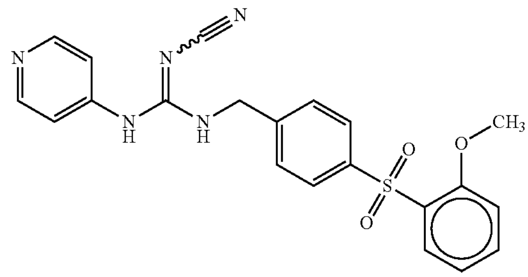 | 2-cyano-1-({4-[(2-methoxybenzene)sulfonyl]phenyl}methyl)-3-(pyridin-4-yl)guanidine |
| 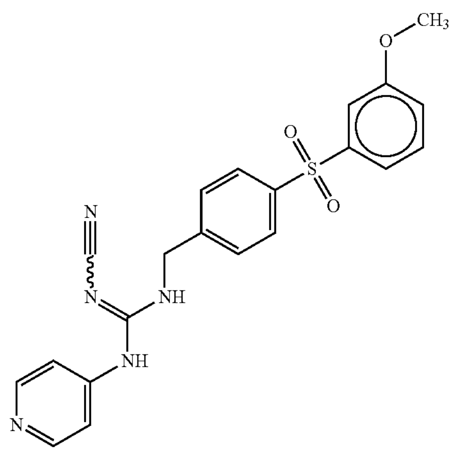 | 2-cyano-1-({4-[(3-methoxybenzene)sulfonyl]phenyl}methyl)-3-(pyridin-4-yl)guanidine |
| 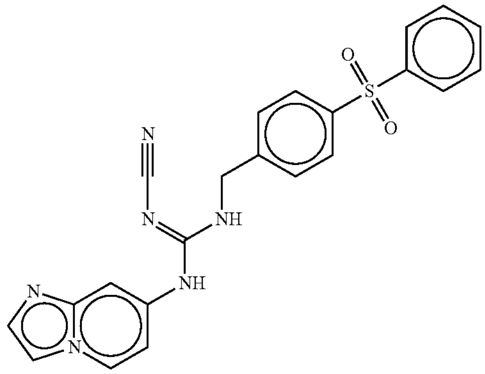 | 3-{[4-(benzenesulfonyl)phenyl]methyl}-2-cyano-1-{imidazo[1,2-a]pyridin-7-yl}guanidine |

TABLE 2-continued
| Structure | Chemical Name |
|---|---|
| 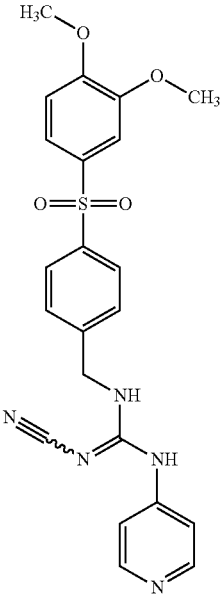 [SMILES: COc1ccc(S(=O)(=O)c2ccc(CNC(=NC#N)Nc3ccncc3)cc2)cc1OC] | 2-cyano-1-({4-[(3,4-dimethoxybenzene)sulfonyl]phenyl}methyl)-3-(pyridin-4-yl)guanidine |
| 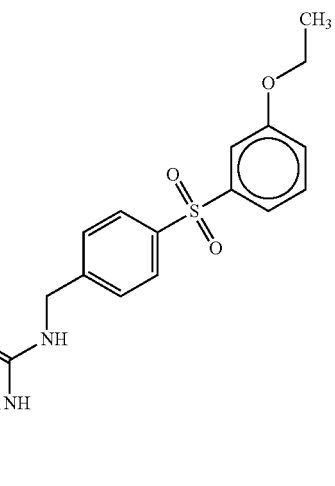 | 2-cyano-1-({4-[(3-ethoxybenzene)sulfonyl]phenyl}methyl)-3-(pyridin-4-yl)guanidine |
| 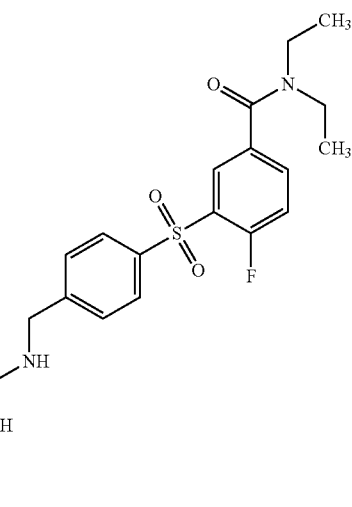 | 3-[(4-{[2-cyano-3-(pyridin-4-yl)carbamimidamido]methyl}benzene)sulfonyl]-N,N-diethyl-4-fluorobenzamide |

TABLE 2-continued

| Structure | Chemical Name |
|---|---|
| 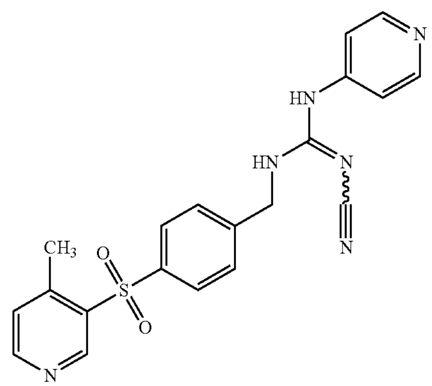 [SMILES: Cc1ccncc1S(=O)(=O)c1ccc(CNC(=NC#N)Nc2ccncc2)cc1] | 2-cyano-1-{[4-(4-methylpyridine-3-sulfonyl)phenyl]methyl}-3-(pyridin-4-yl)guanidine |
| 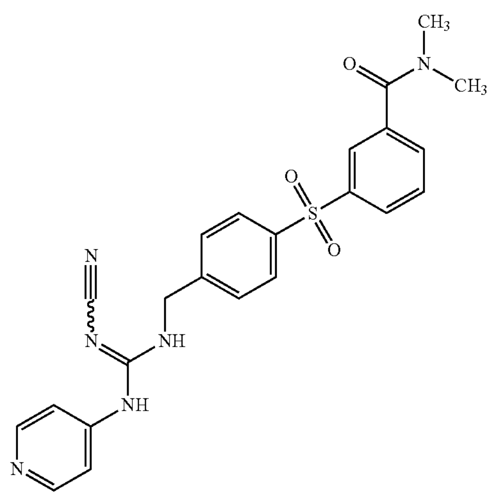 [SMILES: CN(C)C(=O)c1cccc(S(=O)(=O)c2ccc(CNC(=NC#N)Nc3ccncc3)cc2)c1] | 3-[(4-{[2-cyano-3-(pyridin-4-yl)carbamimidamido]methyl}benzene)sulfonyl]-N,N-dimethylbenzamide |
| 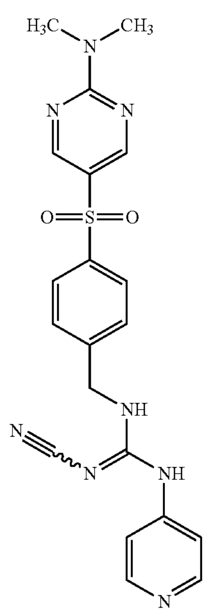 [SMILES: CN(C)c1ncc(S(=O)(=O)c2ccc(CNC(=NC#N)Nc3ccncc3)cc2)cn1] | 2-cyano-1-({4-[2-(dimethylamino)pyrimidine-5-sulfonyl]phenyl}methyl)-3-(pyridin-4-yl)guanidine |

TABLE 2-continued

| Structure | Chemical Name |
|---|---|
| 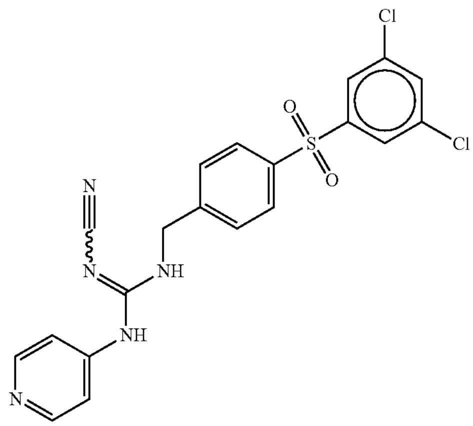 | 2-cyano-1-({4-[(3,5-dichlorobenzene)sulfonyl]phenyl}methyl)-3-(pyridin-4-yl)guanidine |
| 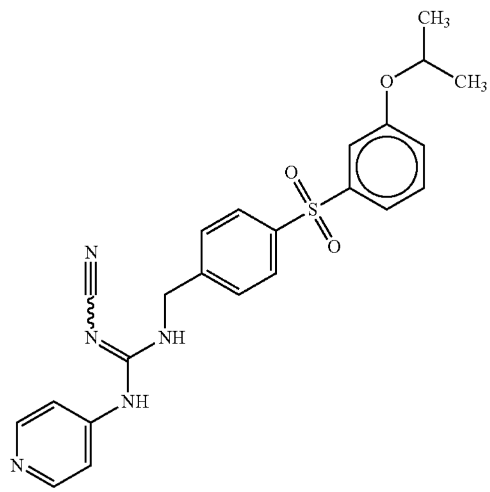 | 2-cyano-1-[(4-{[3-(propan-2-yloxy)benzene]sulfonyl}phenyl)methyl]-3-(pyridin-4-yl)guanidine |
| 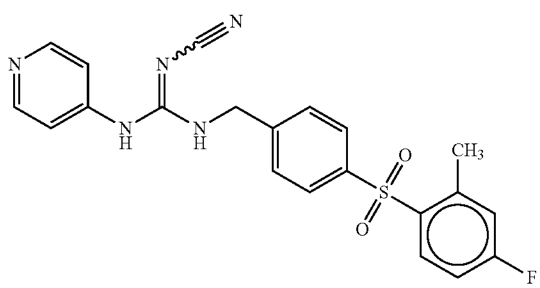 | 2-cyano-1-({4-[(4-fluoro-2-methylbenzene)sulfonyl]phenyl}methyl)-3-(pyridin-4-yl)guanidine |
| 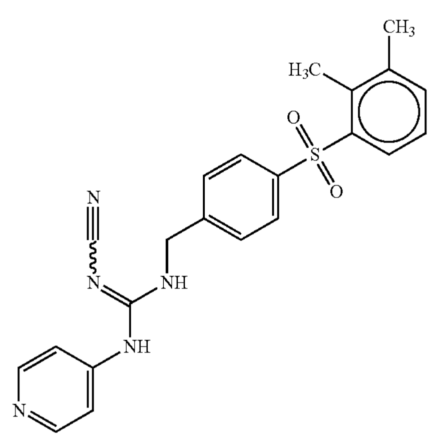 | 2-cyano-1-({4-[(2,3-dimethylbenzene)sulfonyl]phenyl}methyl)-3-(pyridin-4-yl)guanidine |

TABLE 2-continued

| Structure | Chemical Name |
|---|---|
| 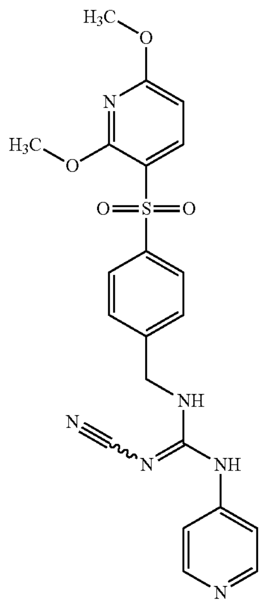 [SMILES: COc1ccc(S(=O)(=O)c2ccc(CNC(=NC#N)Nc3ccncc3)cc2)c(OC)n1] | 2-cyano-1-{[4-(2,6-dimethoxypyridine-3-sulfonyl)phenyl]methyl}-3-(pyridin-4-yl)guanidine |
| 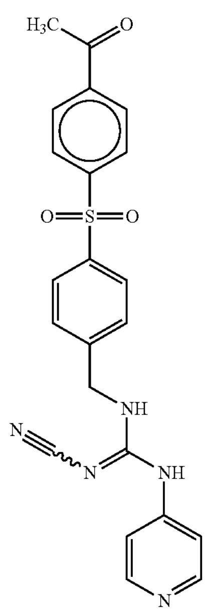 | 1-({4-[(4-acetylbenzene)sulfonyl]phenyl}methyl)-2-cyano-3-(pyridin-4-yl)guanidine |

TABLE 2-continued

| Structure | Chemical Name |
|---|---|
| 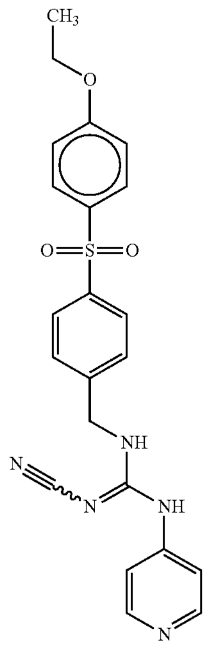 | 2-cyano-1-({4-[(4-ethoxybenzene)sulfonyl]phenyl}methyl)-3-(pyridin-4-yl)guanidine |
| 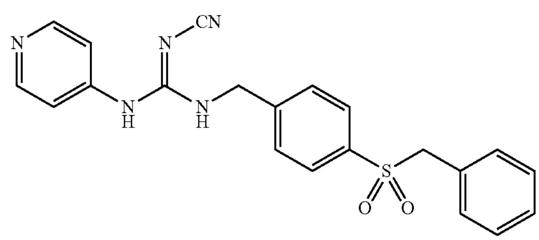 [SMILES: N#C/N=C(\NCc1ccc(S(=O)(=O)Cc2ccccc2)cc1)Nc1ccncc1] | 2-cyano-3-{[4-(phenylmethane)sulfonylphenyl]methyl}-1-(pyridin-4-yl)guanidine |
| 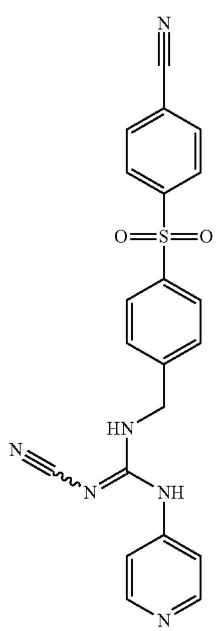 [SMILES: N#CN=C(NCc1ccc(S(=O)(=O)c2ccc(C#N)cc2)cc1)Nc1ccncc1] | 2-cyano-1-({4-[(4-cyanobenzene)sulfonyl]phenyl}methyl)-3-(pyridin-4-yl)guanidine |

TABLE 2-continued
| Structure | Chemical Name |
|---|---|
| 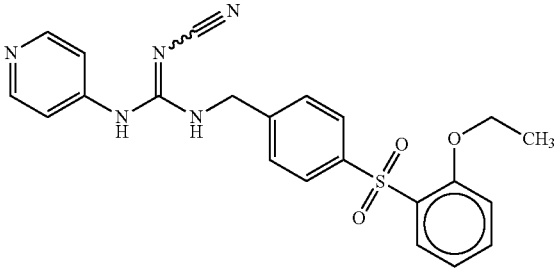 | 2-cyano-1-({4-[(2-ethoxybenzene)sulfonyl]phenyl}methyl)-3-(pyridin-4-yl)guanidine |
| 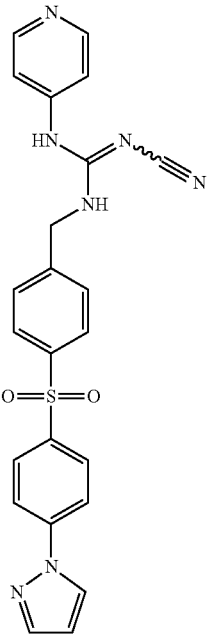 [SMILES: N#CN=C(NCc1ccc(S(=O)(=O)c2ccc(-n3cccn3)cc2)cc1)Nc1ccncc1] | 2-cyano-1-[(4-{[4-(1H-pyrazol-1-yl)benzene]sulfonyl}phenyl)methyl]-3-(pyridin-4-yl)guanidine |
| 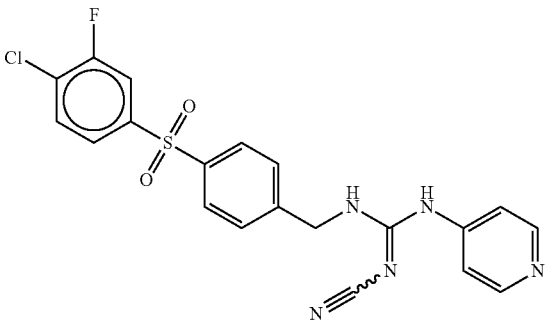 | 1-({4-[(4-chloro-3-fluorobenzene)sulfonyl]phenyl}methyl)-2-cyano-3-(pyridin-4-yl)guanidine |
| 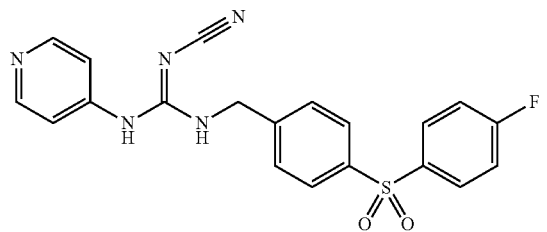 [SMILES: N#C/N=C(\NCc1ccc(S(=O)(=O)c2ccc(F)cc2)cc1)Nc1ccncc1] | 2-cyano-3-({4-[(4-fluorobenzene)sulfonyl]phenyl}methyl)-1-(pyridin-4-yl)guanidine |

TABLE 2-continued

| Structure | Chemical Name |
|---|---|
| 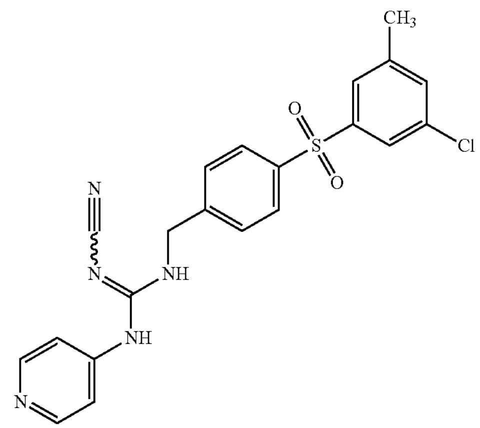 [SMILES: Cc1cc(Cl)cc(S(=O)(=O)c2ccc(CNC(=NC#N)Nc3ccncc3)cc2)c1] | 1-({4-[(3-chloro-5-methylbenzene)sulfonyl]phenyl}methyl)-2-cyano-3-(pyridin-4-yl)guanidine |
| 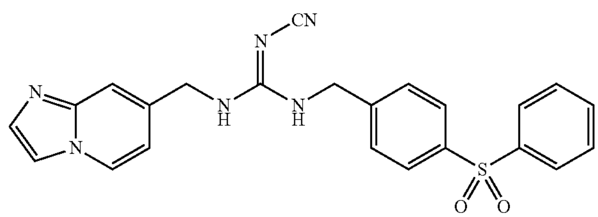 [SMILES: N#C/N=C(\NCc1ccc(S(=O)(=O)c2ccccc2)cc1)NCc1ccn2ccnc2c1] | 3-{[4-(benzenesulfonyl)phenyl]methyl}-2-cyano-1-{imidazo[1,2-a]pyridin-7-ylmethyl}guanidine |
| 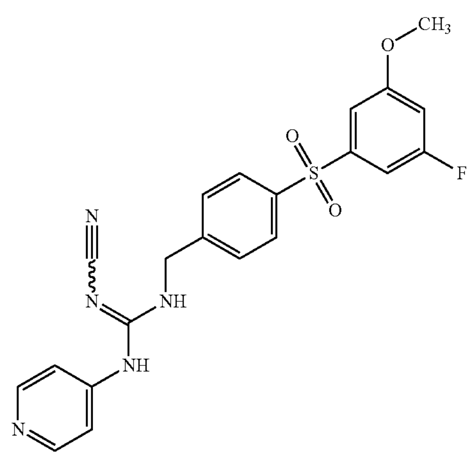 [SMILES: COc1cc(F)cc(S(=O)(=O)c2ccc(CNC(=NC#N)Nc3ccncc3)cc2)c1] | 2-cyano-1-({4-[(3-fluoro-5-methoxybenzene)sulfonyl]phenyl}methyl)-3-(pyridin-4-yl)guanidine |
| 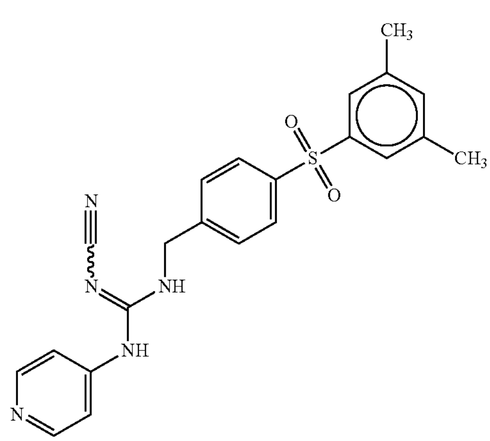 | 2-cyano-1-({4-[(3,5-dimethylbenzene)sulfonyl]phenyl}methyl)-3-(pyridin-4-yl)guanidine |

TABLE 2-continued

| Structure | Chemical Name |
|---|---|
| 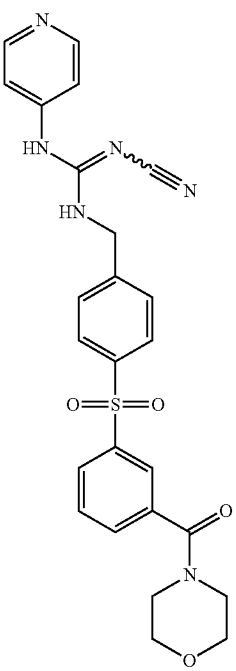 [SMILES: N#CN=C(NCc1ccc(S(=O)(=O)c2cccc(C(=O)N3CCOCC3)c2)cc1)Nc1ccncc1] | 2-cyano-1-{[4-({3-[(morpholin-4-yl)carbonyl]benzene}sulfonyl)phenyl]methyl}-3-(pyridin-4-yl)guanidine |
| 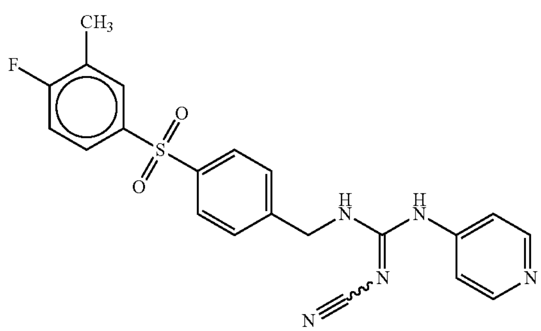 | 2-cyano-1-({4-[(4-fluoro-3-methylbenzene)sulfonyl]phenyl}methyl)-3-(pyridin-4-yl)guanidine |
| 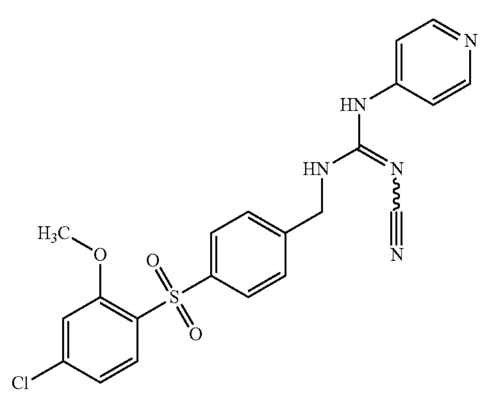 [SMILES: COc1cc(Cl)ccc1S(=O)(=O)c1ccc(CNC(=NC#N)Nc2ccncc2)cc1] | 1-({4-[(4-chloro-2-methoxybenzene)sulfonyl]phenyl}methyl)-2-cyano-3-(pyridin-4-yl)guanidine |

TABLE 2-continued

| Structure | Chemical Name |
|---|---|
| 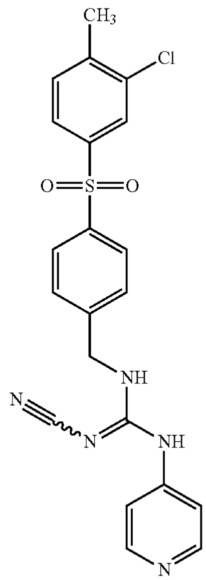 [SMILES: Cc1ccc(S(=O)(=O)c2ccc(CNC(=NC#N)Nc3ccncc3)cc2)cc1Cl] | 1-({4-[(3-chloro-4-methylbenzene) sulfonyl]phenyl}methyl)-2-cyano-3-(pyridin-4-yl)guanidine |
| 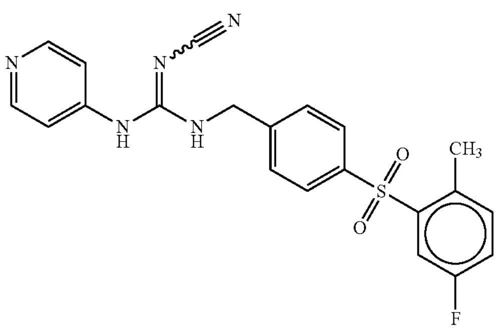 | 2-cyano-1-({4-[(5-fluoro-2-methylbenzene)sulfonyl]phenyl} methyl)-3-(pyridin-4-yl)guanidine |
| 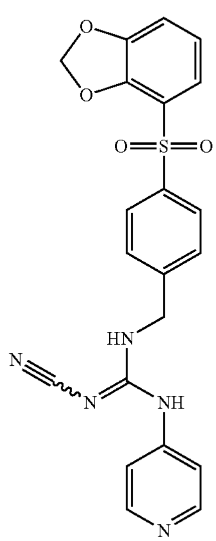 [SMILES: N#CN=C(NCc1ccc(S(=O)(=O)c2cccc3c2OCO3)cc1)Nc1ccncc1] | 1-{[4-(2H-1,3-benzodioxole-4-sulfonyl)phenyl]methyl}-2-cyano-3-(pyridin-4-yl)guanidine |

TABLE 2-continued

| Structure | Chemical Name |
| --- | --- |
| 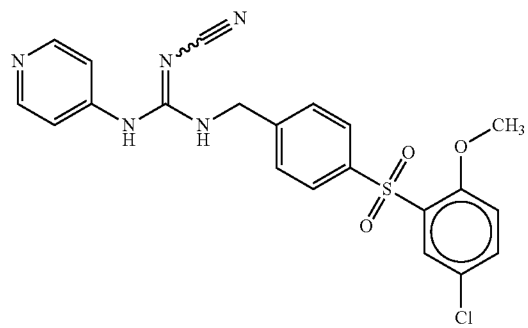 | 1-({4-[(5-chloro-2-methoxybenzene)sulfonyl]phenyl}methyl)-2-cyano-3-(pyridin-4-yl)guanidine |
| 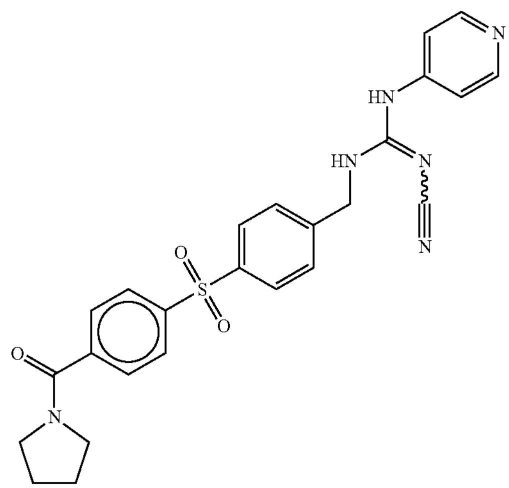 | 2-cyano-3-(pyridin-4-yl)-1-{[4-({4-[(pyrrolidin-1-yl)carbonyl]benzene}sulfonyl)phenyl]methyl}guanidine |
| 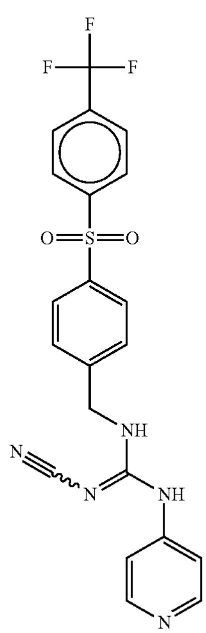 | 2-cyano-3-(pyridin-4-yl)-1-[(4-{[4-(trifluoromethyl)benzene]sulfonyl}phenyl)methyl]guanidine |

TABLE 2-continued
| Structure | Chemical Name |
|---|---|
| 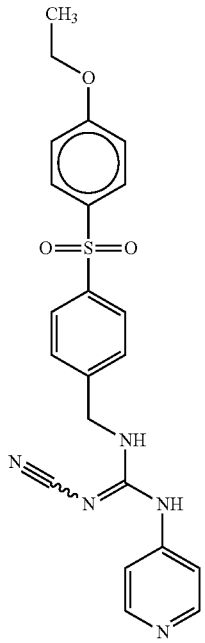 | 2-cyano-1-({4-[(4-ethoxybenzene)sulfonyl]phenyl}methyl)-3-(pyridin-4-yl)guanidine |
| 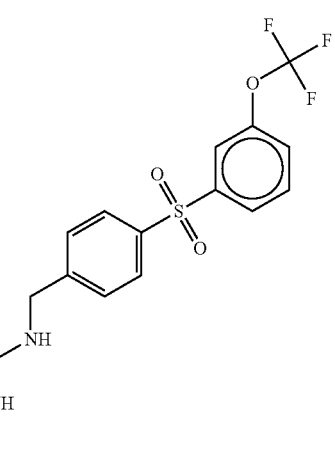 | 2-cyano-3-(pyridin-4-yl)-1-[(4-{[3-(trifluoromethoxy)benzene]sulfonyl}phenyl)methyl]guanidine |
| 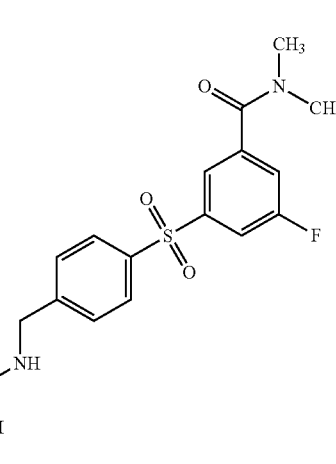 | 3-[(4-{[2-cyano-3-(pyridin-4-yl)carbamimidamido]methyl}benzene)sulfonyl]-5-fluoro-N,N-dimethylbenzamide |

TABLE 2-continued
| Structure | Chemical Name |
|---|---|
| 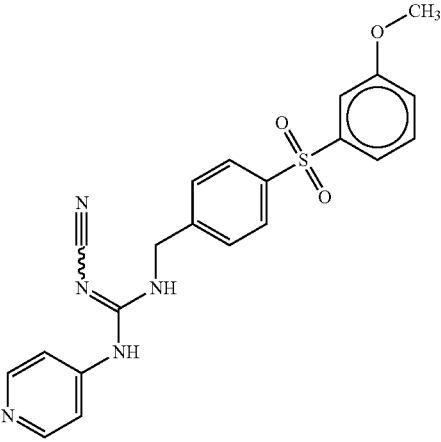 | 2-cyano-1-({4-[(3-methoxybenzene)sulfonyl]phenyl}methyl)-3-(pyridin-4-yl)guanidine |
| 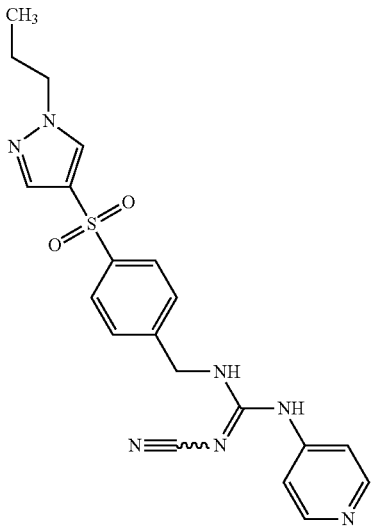 [SMILES: CCCn1cc(S(=O)(=O)c2ccc(CNC(=NC#N)Nc3ccncc3)cc2)cn1] | 2-cyano-1-{[4-(1-propyl-1H-pyrazole-4-sulfonyl)phenyl]methyl}-3-(pyridin-4-yl)guanidine |
| 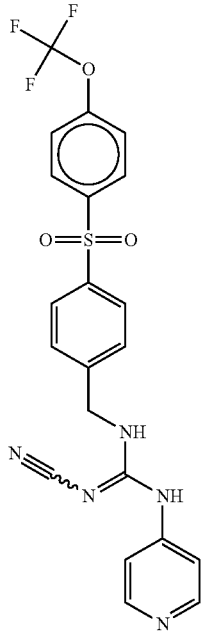 | 2-cyano-3-(pyridin-4-yl)-1-[(4-{[4-(trifluoromethoxy)benzene]sulfonyl}phenyl)methyl]guanidine |

TABLE 2-continued

| Structure | Chemical Name |
|---|---|
| 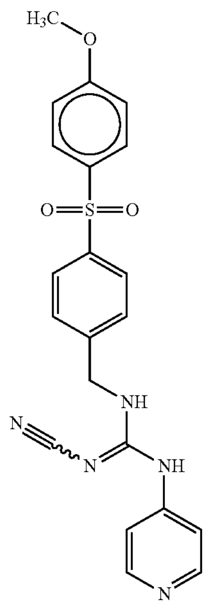 | 2-cyano-1-({4-[(4-ethylbenzene)sulfonyl]phenyl}methyl)-3-(pyridin-4-yl)guanidine |
| 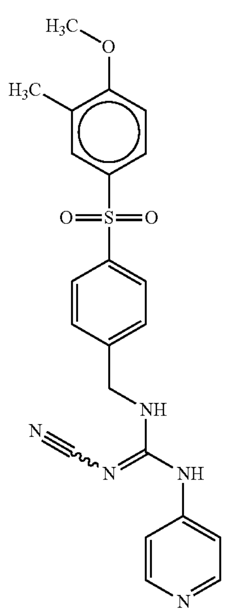 | 2-cyano-1-({4-[(4-methoxy-3-methylbenzene)sulfonyl]phenyl}methyl)-3-(pyridin-4-yl)guanidine |

TABLE 2-continued
| Structure | Chemical Name |
|---|---|
| 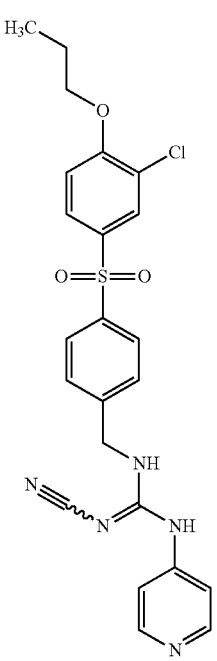 [SMILES: CCCOc1ccc(S(=O)(=O)c2ccc(CNC(=NC#N)Nc3ccncc3)cc2)cc1Cl] | 1-({4-[(3-chloro-4-propoxybenzene)sulfonyl]phenyl}methyl)-2-cyano-3-(pyridin-4-yl)guanidine |
| 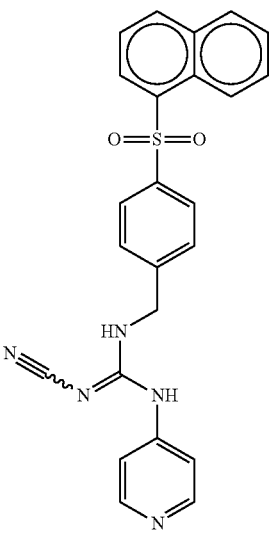 | 2-cyano-1-{[4-(naphthalene-1-sulfonyl)phenyl]methyl}-3-(pyridin-4-yl)guanidine |

TABLE 2-continued

| Structure | Chemical Name |
|---|---|
| 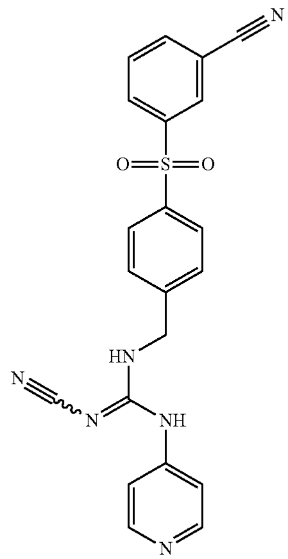 [SMILES: N#CN=C(NCc1ccc(S(=O)(=O)c2cccc(C#N)c2)cc1)Nc1ccncc1] | 2-cyano-1-({4-[(3-cyanobenzene)sulfonyl]phenyl}methyl)-3-(pyridin-4-yl)guanidine |
| 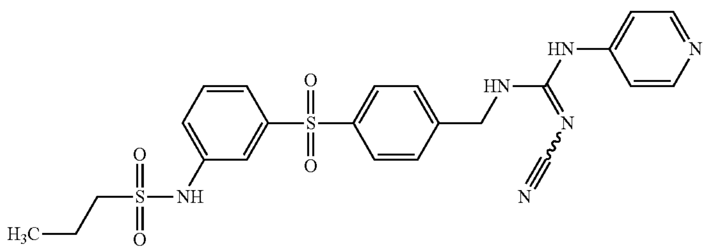 [SMILES: CCCS(=O)(=O)Nc1cccc(S(=O)(=O)c2ccc(CNC(=NC#N)Nc3ccncc3)cc2)c1] | 2-cyano-1-[(4-{[3-(propane-1-sulfonamido)benzene]sulfonyl}phenyl)methyl]-3-(pyridin-4-yl)guanidine |
| 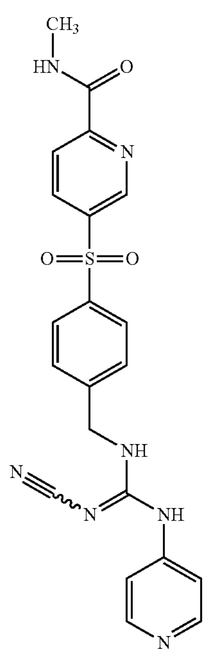 [SMILES: CNC(=O)c1ccc(S(=O)(=O)c2ccc(CNC(=NC#N)Nc3ccncc3)cc2)cn1] | 5-[4-{[2-cyano-3-(pyridin-4-yl)carbamimidamido]methyl}benzene)sulfonyl]-N-methylpyridine-2-carboxamide |

TABLE 2-continued

| Structure | Chemical Name |
|---|---|
| 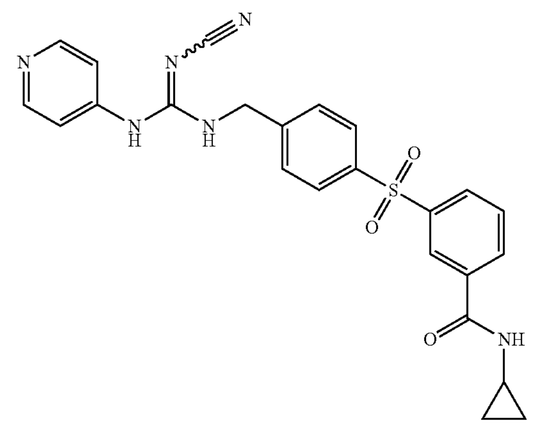 [SMILES: N#CN=C(NCc1ccc(S(=O)(=O)c2cccc(C(=O)NC3CC3)c2)cc1)Nc1ccncc1] | 3-[(4-{[2-cyano-3-(pyridin-4-yl)carbamimidamido]methyl}benzene)sulfonyl]-N-cyclopropylbenzamide |
| 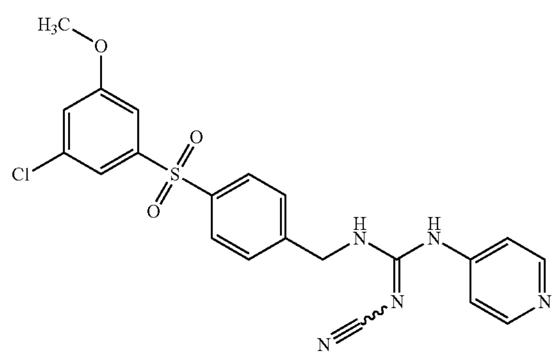 [SMILES: COc1cc(Cl)cc(S(=O)(=O)c2ccc(CNC(=NC#N)Nc3ccncc3)cc2)c1] | 1-({4-[(3-chloro-5-methoxybenzene)sulfonyl]phenyl}methyl)-2-cyano-3-(pyridin-4-yl)guanidine |
| 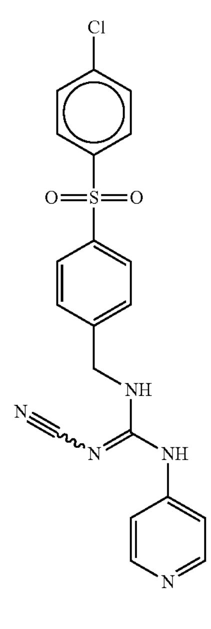 | 1-({4-[(4-chlorobenzene)sulfonyl]phenyl}methyl)-2-cyano-3-(pyridin-4-yl)guanidine |

TABLE 2-continued

| Structure | Chemical Name |
|---|---|
| 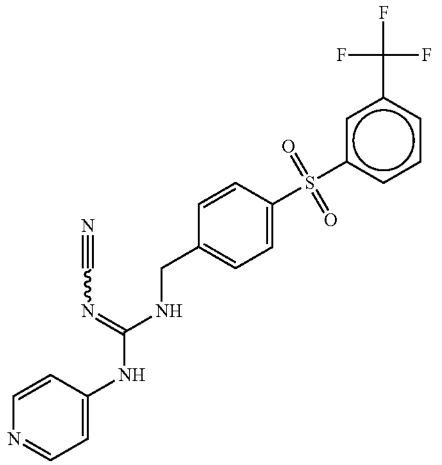 | 2-cyano-3-(pyridin-4-yl)-1-[(4-{[3-(trifluoromethyl)benzene]sulfonyl}phenyl)methyl]guanidine |
| 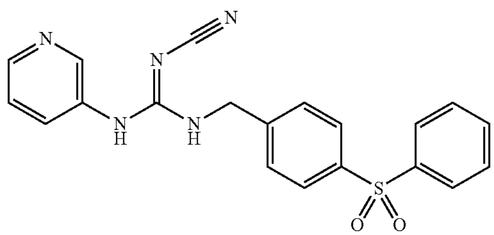 [SMILES: N#C/N=C(\NCc1ccc(S(=O)(=O)c2ccccc2)cc1)Nc1cccnc1] | 3-{[4-(benzenesulfonyl)phenyl]methyl}-2-cyano-1-(pyridin-3-yl)guanidine |
| 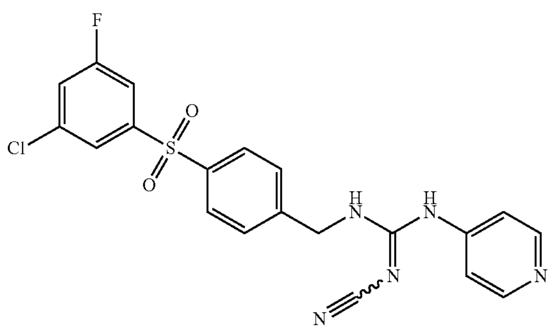 [SMILES: N#CN=C(NCc1ccc(S(=O)(=O)c2cc(F)cc(Cl)c2)cc1)Nc1ccncc1] | 1-({4-[(3-chloro-5-fluorobenzene)sulfonyl]phenyl}methyl)-2-cyano-3-(pyridin-4-yl)guanidine |
| 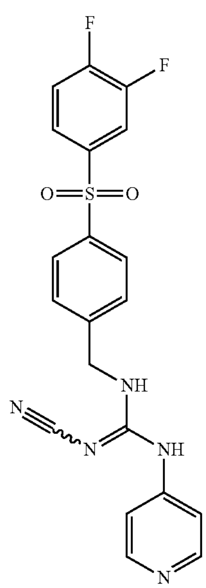 [SMILES: N#CN=C(NCc1ccc(S(=O)(=O)c2ccc(F)c(F)c2)cc1)Nc1ccncc1] | 2-cyano-1-({4-[(3,4-difluorobenzene)sulfonyl]phenyl}methyl)-3-(pyridin-4-yl)guanidine |

TABLE 2-continued

| Structure | Chemical Name |
|---|---|
| 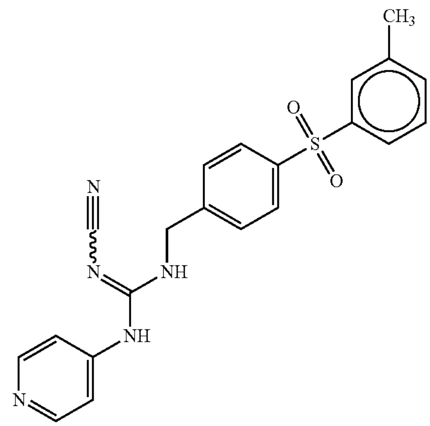 | 2-cyano-1-({4-[(3-methylbenzene)sulfonyl]phenyl}methyl)-3-(pyridin-4-yl)guanidine |
| 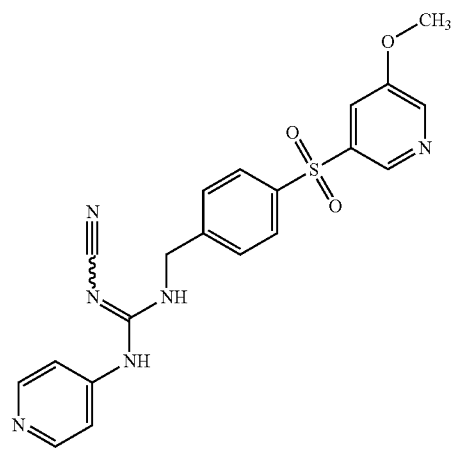 [SMILES: COc1cncc(S(=O)(=O)c2ccc(CNC(=NC#N)Nc3ccncc3)cc2)c1] | 2-cyano-1-{[4-(5-methoxypyridine-3-sulfonyl)phenyl]methyl}-3-(pyridin-4-yl)guanidine |
| 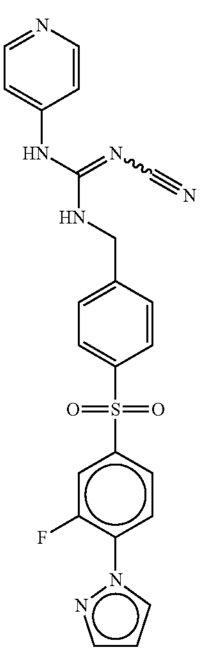 | 2-cyano-1-[(4-{[3-fluoro-4-(1H-pyrazol-1-yl)benzene]sulfonyl}phenyl)methyl]-3-(pyridin-4-yl)guanidine |

TABLE 2-continued

| Structure | Chemical Name |
|---|---|
| 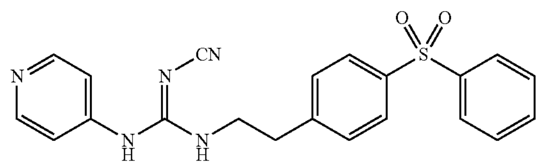 [SMILES: N#C/N=C(\NCCc1ccc(S(=O)(=O)c2ccccc2)cc1)Nc1ccncc1] | 1-{2-[4-(benzenesulfonyl)phenyl]ethyl}-2-cyano-3-(pyridin-4-yl)guanidine |
| | 2-cyano-1-({4-[(3-fluoro-4-methylbenzene)sulfonyl]phenyl}methyl)-3-(pyridin-4-yl)guanidine |
| | 2-cyano-1-({4-[(3-fluoro-4-methylbenzene)sulfonyl]phenyl}methyl)-3-(pyridin-4-yl)guanidine |
| 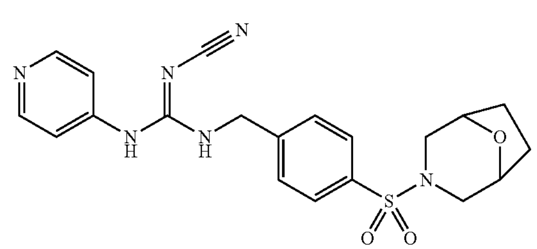 [SMILES: N#C/N=C(\NCc1ccc(S(=O)(=O)N2CC3CCC(C2)O3)cc1)Nc1ccncc1] | 2-cyano-3-[(4-{8-oxa-3-azabicyclo[3.2.1]octane-3-sulfonyl}phenyl)methyl]-1-(pyridin-4-yl)guanidine |

TABLE 2-continued

| Structure | Chemical Name |
|---|---|
| 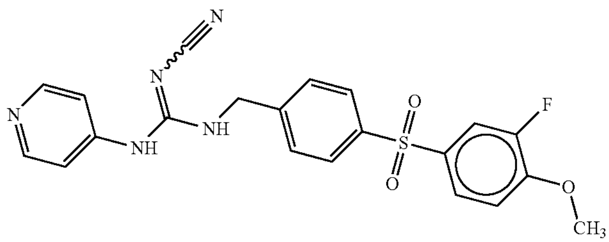 | 2-cyano-1-({4-[(3-fluoro-4-methoxybenzene)sulfonyl]phenyl}methyl)-3-(pyridin-4-yl)guanidine |
| 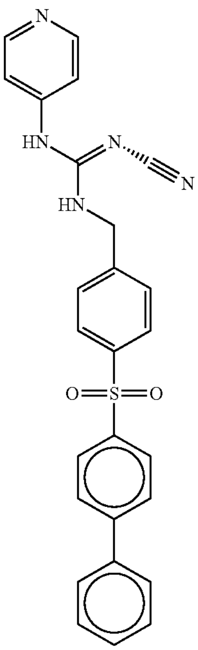 | 2-cyano-1-({4-[(4-phenylbenzene)sulfonyl]phenyl}methyl)-3-(pyridin-4-yl)guanidine |
| 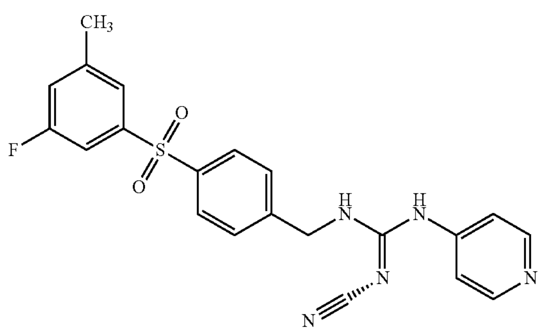 | 2-cyano-1-({4-[(3-fluoro-5-methylbenzene)sulfonyl]phenyl}methyl)-3-(pyridin-4-yl)guanidine |
| 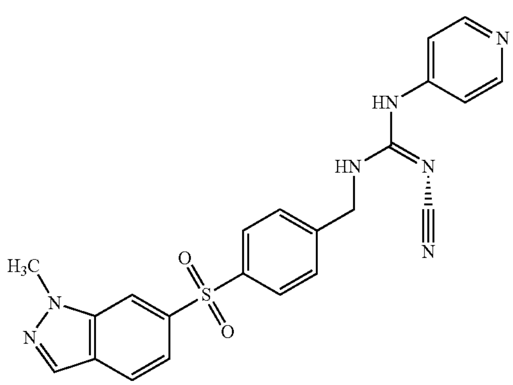 | 2-cyano-1-{[4-(1-methyl-1H-indazole-6-sulfonyl)phenyl]methyl}-3-(pyridin-4-yl)guanidine |

TABLE 2-continued

| Structure | Chemical Name |
|---|---|
| 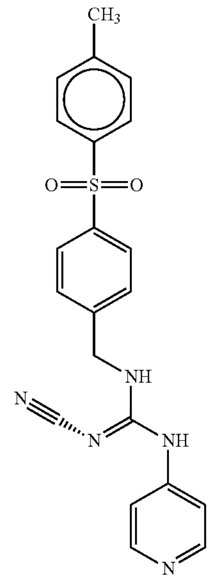 | 2-cyano-1-({4-[(4-methylbenzene)sulfonyl]phenyl}methyl)-3-(pyridin-4-yl)guanidine |
| 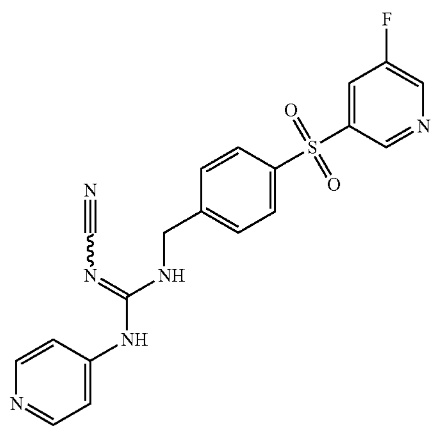 [SMILES: N#CN=C(NCc1ccc(S(=O)(=O)c2cncc(F)c2)cc1)Nc1ccncc1] | 2-cyano-1-{[4-(5-fluoropyridine-3-sulfonyl)phenyl]methyl}-3-(pyridin-4-yl)guanidine |
| 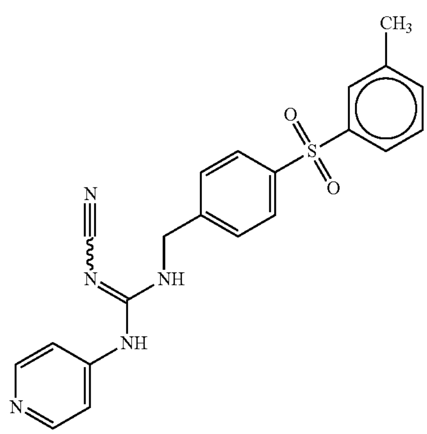 | 2-cyano-1-({4-[(3-methylbenzene)sulfonyl]phenyl}methyl)-3-(pyridin-4-yl)guanidine |

TABLE 2-continued

| Structure | Chemical Name |
|---|---|
| 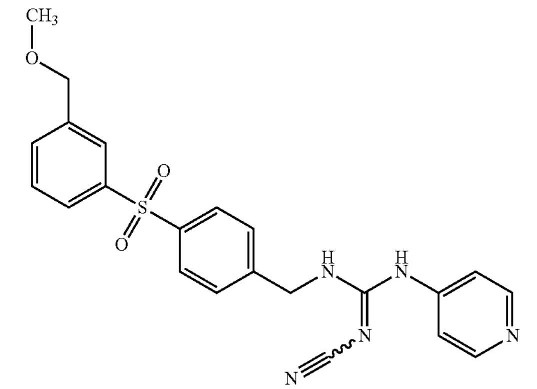 [SMILES: COCc1cccc(S(=O)(=O)c2ccc(CNC(=NC#N)Nc3ccncc3)cc2)c1] | 2-cyano-1-[(4-{[3-(methoxymethyl)benzene]sulfonyl}phenyl)methyl]-3-(pyridin-4-yl)guanidine |
| 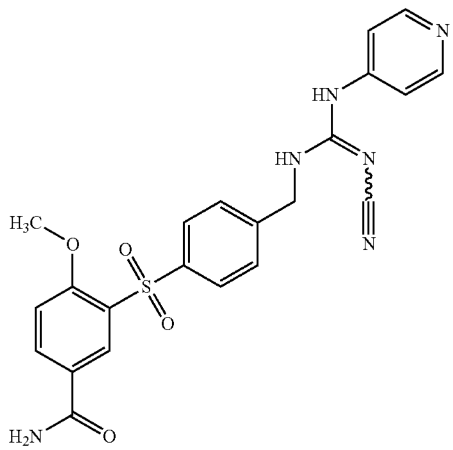 [SMILES: COc1ccc(C(N)=O)cc1S(=O)(=O)c1ccc(CNC(=NC#N)Nc2ccncc2)cc1] | 1-({4-[(5-acetyl-2-methoxybenzene)sulfonyl]phenyl}methyl)-2-cyano-3-(pyridin-4-yl)guanidine |
| 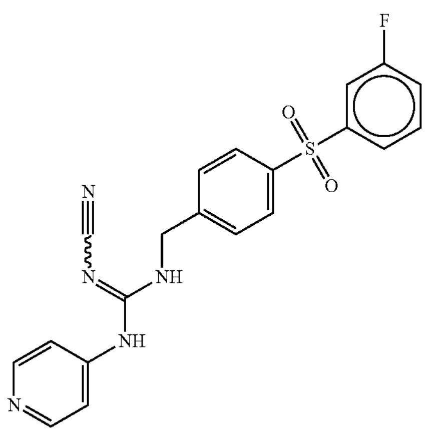 | 2-cyano-1-({4-[(3-fluorobenzene)sulfonyl]phenyl}methyl)-3-(pyridin-4-yl)guanidine |
| 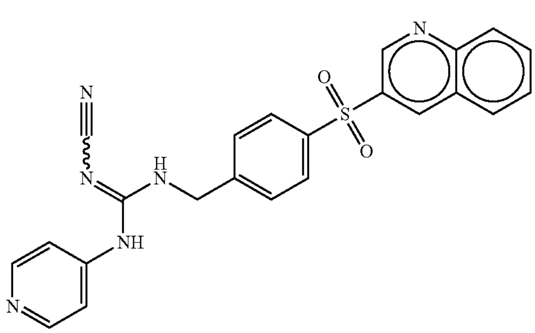 | 2-cyano-3-(pyridin-4-yl)-1-{[4-(quinoline-3-sulfonyl)phenyl]methyl}guanidine |

TABLE 2-continued

| Structure | Chemical Name |
|---|---|
| 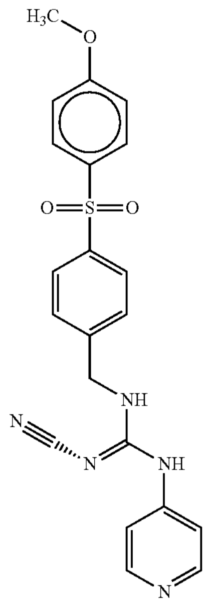 | 2-cyano-1-({4-[(4-methoxybenzene)sulfonyl]phenyl}methyl)-3-(pyridin-4-yl)guanidine |
| 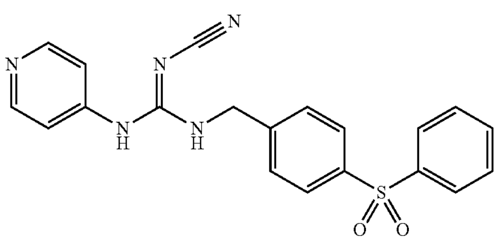 [SMILES: N#C/N=C(\NCc1ccc(S(=O)(=O)c2ccccc2)cc1)Nc1ccncc1] | 3-{[4-(benzenesulfonyl)phenyl]methyl}-2-cyano-1-(pyridin-4-yl)guanidine |
| 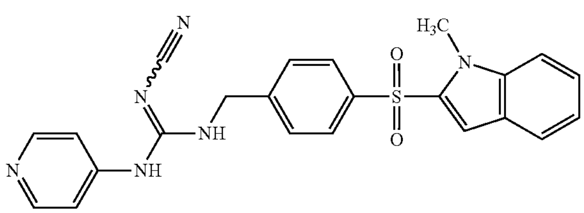 [SMILES: Cn1c(S(=O)(=O)c2ccc(CNC(=NC#N)Nc3ccncc3)cc2)cc2ccccc21] | 2-cyano-1-{[4-(1-methyl-1H-indole-2-sulfonyl)phenyl]methyl}-3-(pyridin-4-yl)guanidine |
| 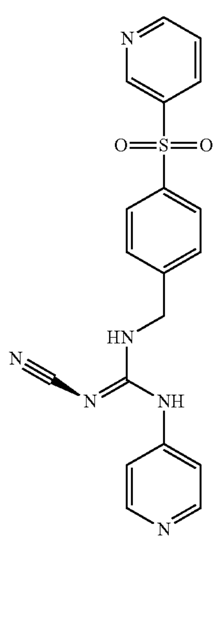 | 2-cyano-3-(pyridin-4-yl)-1-{[4-(pyridine-3-sulfonyl)phenyl]methyl}guanidine |

TABLE 2-continued

| Structure | Chemical Name |
|---|---|
| 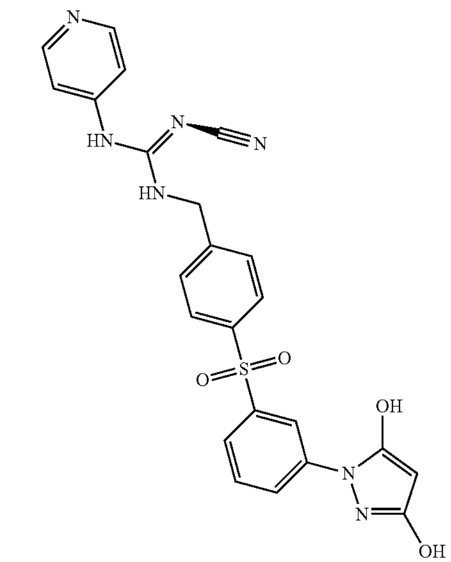 | 2-cyano-1-[(4-{[3-(3,5-dimethyl-1H-pyrazol-1-yl)benzene]sulfonyl}phenyl)methyl]-3-(pyridin-4-yl)guanidine |
| 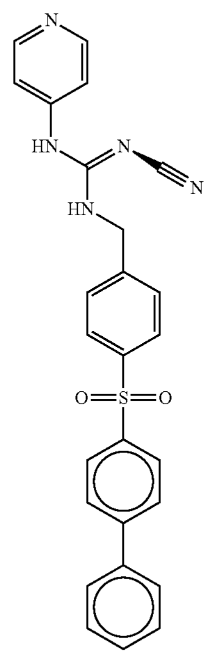 | 3-chloro-5-[(4-{[2-cyano-3-(pyridin-4-yl)carbamimidamido]methyl}benzene)sulfonyl]-N,N-diethylbenzamide |
| 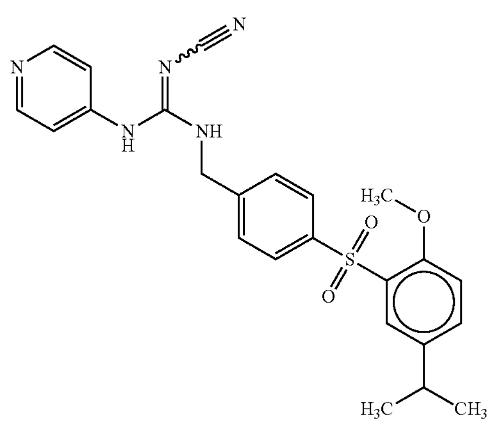 | 2-cyano-1-[(4-{[2-methoxy-5-(propan-2-yl)benzene]sulfonyl}phenyl)methyl]-3-(pyridin-4-yl)guanidine |

TABLE 2-continued

| Structure | Chemical Name |
|---|---|
| 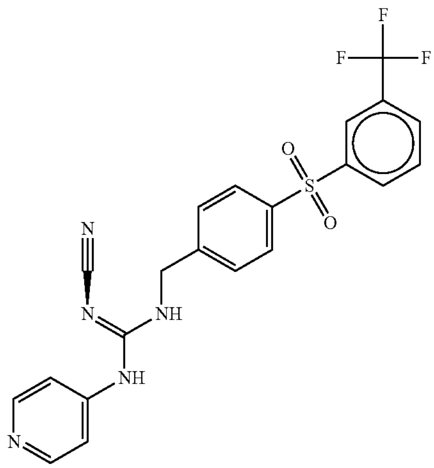 | 2-cyano-3-(pyridin-4-yl)-1-[(4-{[3-(trifluoromethyl)benzene]sulfonyl}phenyl)methyl]guanidine |
| 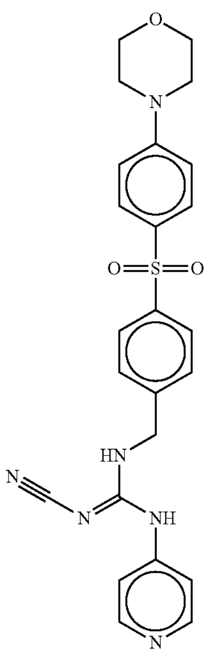 | 2-cyano-1-[(4-{[4-(morpholin-4-yl)benzene]sulfonyl}phenyl)methyl]-3-(pyridin-4-yl)guanidine |
| 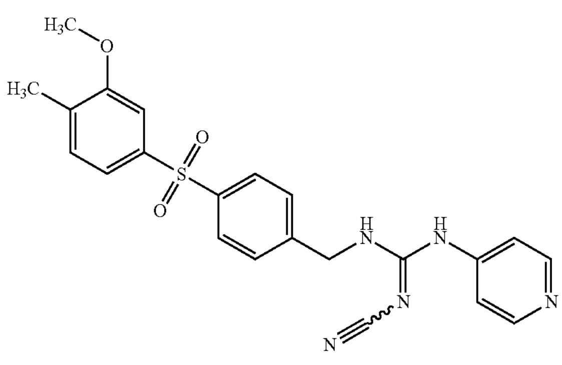 [SMILES: COc1cc(S(=O)(=O)c2ccc(CNC(=NC#N)Nc3ccncc3)cc2)ccc1C] | 2-cyano-1-({4-[(3-methoxy-4-methylbenzene)sulfonyl]phenyl}methyl)-3-(pyridin-4-yl)guanidine |

TABLE 2-continued

| Structure | Chemical Name |
|---|---|
| 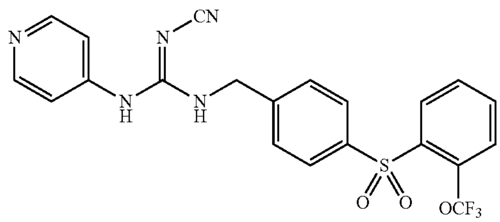 [SMILES: N#C/N=C(\NCc1ccc(S(=O)(=O)c2ccccc2OC(F)(F)F)cc1)Nc1ccncc1] | 2-cyano-1-(pyridin-4-yl)-3-[(4-{[2-(trifluoromethoxy)benzene]sulfonyl}phenyl)methyl]guanidine |
| 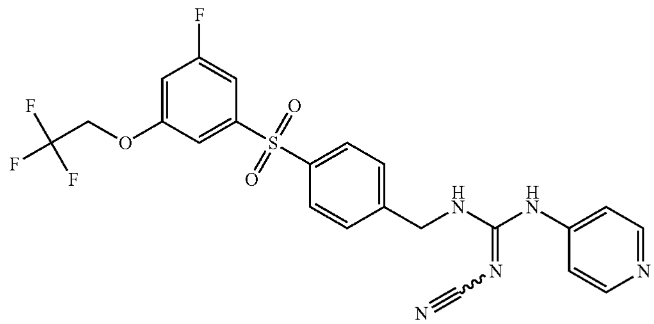 [SMILES: N#CN=C(NCc1ccc(S(=O)(=O)c2cc(F)cc(OCC(F)(F)F)c2)cc1)Nc1ccncc1] | 2-cyano-1-[(4-{[3-fluoro-5-(2,2,2-trifluoroethoxy)benzene]sulfonyl}phenyl)methyl]-3-(pyridin-4-yl)guanidine |
| 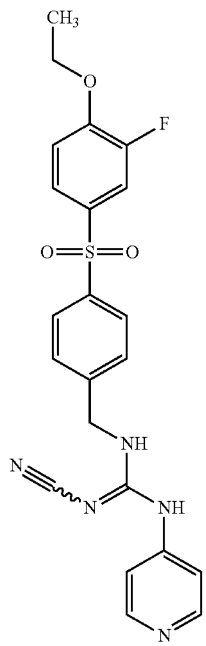 [SMILES: CCOc1ccc(S(=O)(=O)c2ccc(CNC(=NC#N)Nc3ccncc3)cc2)cc1F] | 2-cyano-1-({4-[(4-ethoxy-3-fluorobenzene)sulfonyl]phenyl}methyl)-3-(pyridin-4-yl)guanidine |
| 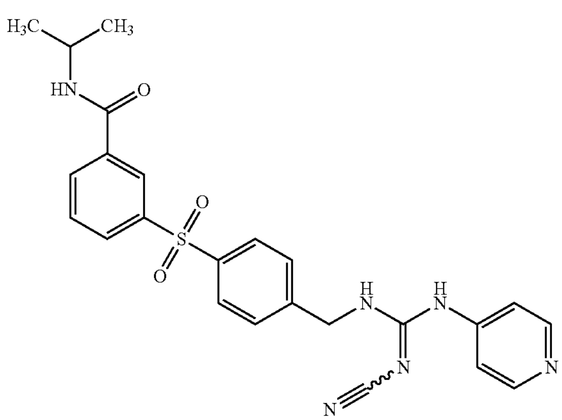 [SMILES: CC(C)NC(=O)c1cccc(S(=O)(=O)c2ccc(CNC(=NC#N)Nc3ccncc3)cc2)c1] | 3-[(4-{[2-cyano-3-(pyridin-4-yl)carbamimidamido]methyl}benzene)sulfonyl]-N-(propan-2-yl)benzamide |

TABLE 2-continued

| Structure | Chemical Name |
|---|---|
| 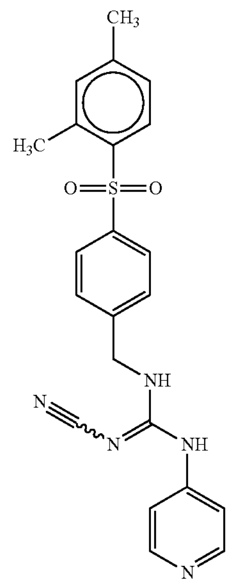 | 2-cyano-1-({4-[(2,4-dimethylbenzene)sulfonyl]phenyl}methyl)-3-(pyridin-4-yl)guanidine |
| 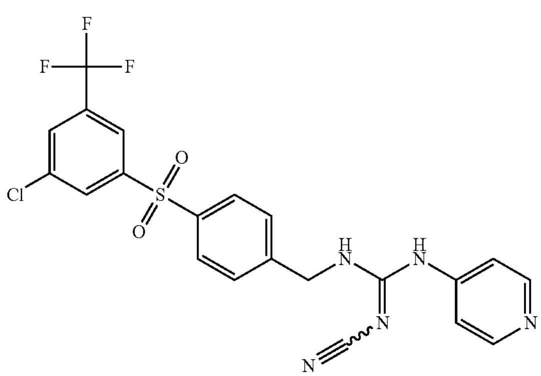 [SMILES: N#CN=C(NCc1ccc(S(=O)(=O)c2cc(Cl)cc(C(F)(F)F)c2)cc1)Nc1ccncc1] | 1-[(4-{[3-chloro-5-(trifluoromethyl)benzene]sulfonyl}phenyl)methyl]-2-cyano-3-(pyridin-4-yl)guanidine |
| 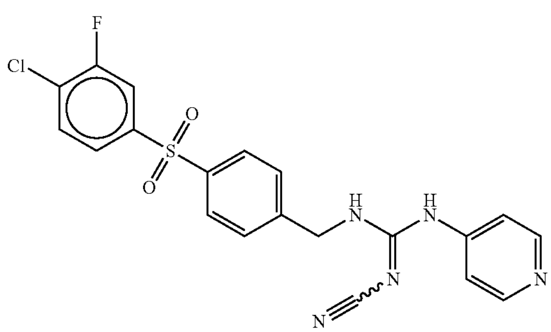 | 1-({4-[(4-chloro-3-fluorobenzene)sulfonyl]phenyl}methyl)-2-cyano-3-(pyridin-4-yl)guanidine |
| 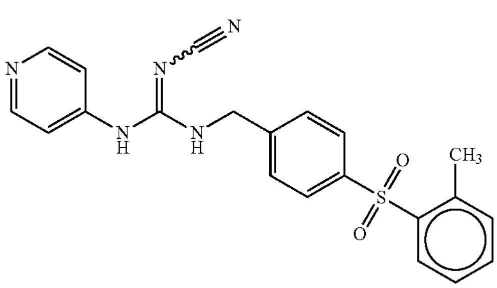 | 2-cyano-1-({4-[(2-methylbenzene)sulfonyl]phenyl}methyl)-3-(pyridin-4-yl)guanidine |

Examples

The following are illustrative, but non-limiting, examples of certain embodiments of the present invention.

Definitions Used in the Following Schemes and Elsewhere Herein are

BOP ammonium 4-(3-(pyridin-3-1methyl)ureido)benzenesulfinate
$CDCl_3$ deuterated chloroform
δ chemical shift (ppm)
DCM dichloromethane or methylene chloride
DIEA N,N-diisopropylethylamine
DMA N,N-dimethylacetamide
DMF N,N-dimethylformamide
DMSO dimethylsulfoxide
DMSO-$d_6$ deuterated dimethylsulfoxide
EDCI N1-((ethylimino)methylene)-N3,N3-dimethylpropane-1,3-diamine hydrochloride
EtOAc ethyl acetate
EtOH ethanol
GF/F glass microfiber filter
$^1$H NMR proton nuclear magnetic resonance
HOAc acetic acid
HATU 2-(3H-[1,2,3]triazolo[4,5-b]pyridin-3-yl)-1,1,3,3-tetramethylisouronium hexafluorophosphate
HOBT 1H-benzo[d][1,2,3]triazol-1-ol hydrate
HPLC high pressure liquid chromatography
MHz megahertz
KOAc potassium acetate
i-PrOH isopropanol
LC-MS liquid chromatography/mass spectrometry
(M+1) mass+1
m-CPBA m-chloroperbenzoic acid
MeOH methanol
$N_2$ nitrogen
$NaHCO_3$ sodium bicarbonate
$MgSO_4$ magnesium sulfate
PTLC preparative thin layer chromatography
TEA triethylamine
THF tetrahydrofuran
TLC thin layer chromatography

Examples

The invention is illustrated further by the following examples, which are not to be construed as limiting the invention in scope or spirit to the specific procedures described in them. Those having skill in the art will recognize that the starting materials may be varied and additional steps employed to produce compounds encompassed by the present inventions, as demonstrated by the following examples. In some cases, protection of certain reactive functionalities may be necessary to achieve some of the above transformations. In general, such need for protecting groups, as well as the conditions necessary to attach and remove such groups, will be apparent to those skilled in the art of organic synthesis.

Preparation of Compounds

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Preferred methods include but are not limited to those methods described below. Compounds of the present invention cyanoguandine (VI) can be synthesized by following the steps outlined in Scheme 1.

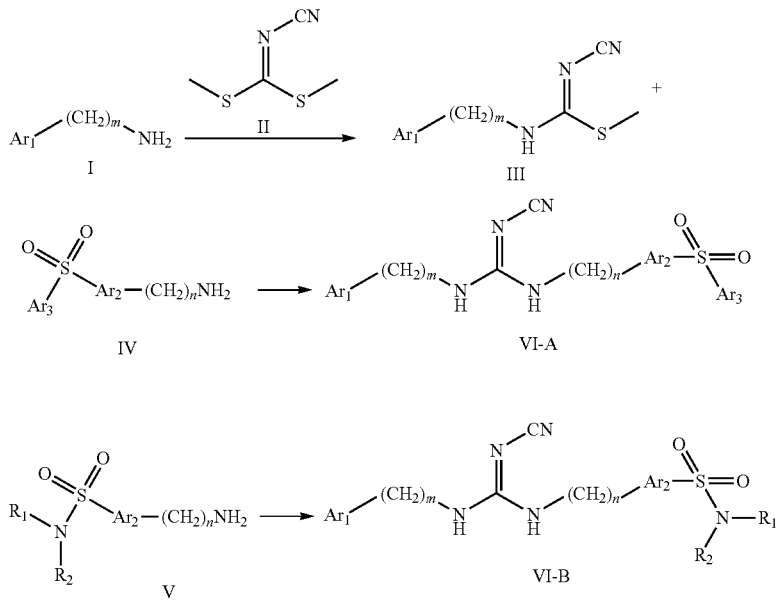

Intermediate III can be obtained by treating I with II in the present of base such as DMAP, DBU in a solvent such as DMF, DMA at temperatures ranging from −78° C. to 200° C. The compound of present invention VI can be obtained by treating compound III with either IV or V in the present of base such as DMAP in an organic solvent such as pyridine at temperatures ranging from −78° C. to 200° C.

Those having skill in the art will recognize that the starting materials may be varied and additional steps employed to produce compounds encompassed by the present inventions, as demonstrated by the following examples. Unless otherwise specified all reagents and solvent are of standard commercial grade and are used without further purification.

These examples illustrate the preparation of representative substituted cyanoguanidine analogues.

EXAMPLES

Preparation of Representative Cyanoguanidine-Sulfone Analogues

These examples illustrate the preparation of representative substituted urea-sulfonamide analogues.

Example 1

2-cyano-1-(4-(phenylsulfonyl)benzyl)-3-(pyridin-3-yl)guanidine

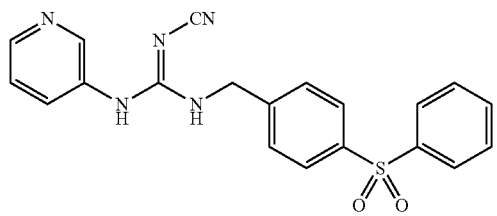 [SMILES: N#C/N=C(\NCc1ccc(S(=O)(=O)c2ccccc2)cc1)Nc1cccnc1]

A: 4-(phenylsulfonyl)benzonitrile

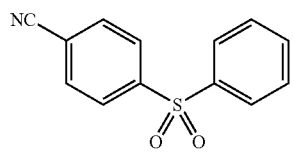 [SMILES: N#Cc1ccc(S(=O)(=O)c2ccccc2)cc1]

A mixture of 4-fluorobenzonitrile (5 g, 41.3 mmol) and sodium benzenesulfinate (7.45 g, 45.4 mmol) in DMSO (30 mL) was heated at 130° C. for 16 hours. The mixture was cooled to room temperature and poured onto 300 g of ice. The precipitate was collected, washed with water, and dried to afford the title compound.

$^1$H NMR (300 MHz, CDCl$_3$): δ 8.03-8.07 (m, 2H), 7.93-7.97 (m, 2H), 7.78-7.82 (m, 2H), 7.60 (m 7.65, 1H), 7.26-7.58 (m, 2H)

B: (4-[phenylsulfonyl]phenyl)methanamine

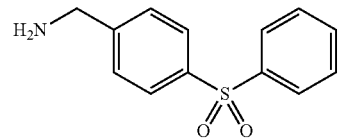 [SMILES: NCc1ccc(S(=O)(=O)c2ccccc2)cc1]

A mixture of 4-(phenylsulfonyl)benzonitrile (9.4 g, 38.64 mmol) and Raney Ni (500 mg) in 2N NH$_3$-MeOH (150 mL) was hydrogenated for 16 hours at 50 psi. Nitrogen gas was bubbled through the mixture, which was then filtered through a short Celite pad, and washed with methanol. The filtrate was concentrated and triturated with ether to afford the title compound.

$^1$H NMR (300 MHz, DMSO-d$_6$): δ 7.85-7.95 (m, 4H), 7.53-7.68 (m, 5H), 3.74 (s, 2H), 1.83 (br s, 2H)

C: methyl N'-cyano-N-(pyridin-3-yl)carbamimidothioate

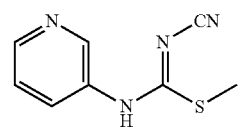

3-aminopyridine (2.0 g, 21.28 mmol) and dimethyl cyanocarbonimidodithioate (4.15 g, 25.2 mmol) were dissolved in DMF (8 mL) and DMAP (0.269 g, 2.13 mmol) was added. The resulting yellow solution was cooled to 0° C. in an ice bath then sodium hydride (0.88 g, 36.6 mmol) was added portionwise over 20 minutes at 0° C. The mixture was quenched with water (10 mL) and was extracted with 20% MeOH/DCM (5×20 mL). The combined organic layers were dried over Na$_2$SO$_4$, filtered and concentrated under reduced pressure to give a yellow residue. The crude material was purified by silica-gel chromatography (2% to 5% MeOH/DCM) to afford the title compound.

$^1$H NMR (300 MHz, DMSO-d$_6$): δ 10.27 (s, 1H), 8.61 (d, 1H), 8.47 (t, 1H), 7.90 (m, 1H), 7.45 (m, 1H), 2.73 (s, 3H)
LC-MS (ESI): 191.0 (M−1).

D: 2-cyano-1-(4-(phenylsulfonyl)benzyl)-3-(pyridin-3-yl)guanidine

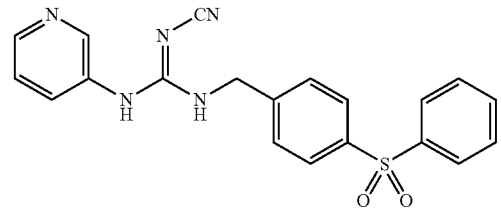 [SMILES: N#C/N=C(\NCc1ccc(S(=O)(=O)c2ccccc2)cc1)Nc1cccnc1]

To a solution of methyl N'-cyano-N-(pyridin-3-yl)carbamimidothioate (50 mg, 0.26 mmol) and (4-[phenylsulfonyl]phenyl)methanamine (81 mg, 0266 mmol) in pyridine (3 mL) was added TEA (73 µL, 0.520 mmol) and DMAP (3.18 mg, 0.026 mmol). The resulting mixture was stirred overnight at 60° C. The reaction mixture was cooled and concentrated under vacuo to afford an off white solid. The crude material was purified by silica-gel chromatography (2% MeOH/DCM to 6% MeOH/DCM) to afford the title compound.

$^1$H NMR (300 MHz, DMSO-d$_6$) δ 8.45 (s, 1H), 8.37 (d, 1H), 7.90 (m, 5H), 7.63 (m, 5H), 7.52 (d, 2H), 7.36 (m, 1H), 4.45 (d, 2H)

LC-MS (ESI): 389.9 (M−1).

Example 2

2-cyano-1-(imidazo[1,2-a]pyridin-7-yl)-3-(4-(phenylsulfonyl)benzyl)guanidine

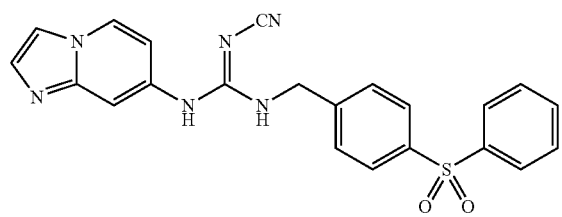 [SMILES: N#C/N=C(\NCc1ccc(S(=O)(=O)c2ccccc2)cc1)Nc1ccn2ccnc2c1]

A: methyl N'-cyano-N-(imidazo[1,2-a]pyridin-7-yl)carbamimidothioate

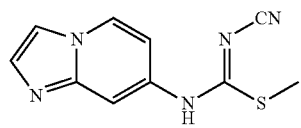 [SMILES: CS/C(=N\C#N)Nc1ccn2ccnc2c1]

In a 100 mL round-bottomed flask was added imidazo[1,2-a]pyridin-7-amine (1 g, 7.51 mmol), dimethyl cyanocarbonimidodithioate (1.318 g, 9.01 mmol), and DMAP (0.092 g, 0.75 mmol) in DMF (Volume: 10 mL) to give a yellow solution. The reaction was cooled to 0° C. and sodium hydride (0.323 g, 12.77 mmol) was added portionwise. The reaction was stirred at 0° C. for 4 hours and then allowed to warm to room temperature overnight. The reaction was then concentrated under reduced pressure and then diluted with methylene chloride and washed with sat. aq. NH$_4$Cl. A large amount of solid was formed in separatory funnel, so filtered entire mixture. Isolated 2.25 g of a yellow powder which showed product by NMR along with an impurity. Purified solid on Biotage to give the title compound.

$^1$H NMR (300 MHz, DMSO-d$_6$): δ 11.25 (br. s, 1H), 8.49 (d, 1H), 7.93 (s, 1H), 7.52 (d, 1H), 7.64 (s, 1H), 7.03 (dd, 1H), 2.82 (s, 3H);

LC-MS (ESI): 232.09 (M+1).

B: 2-cyano-1-(imidazo[1,2-a]pyridin-7-yl)-3-(4-(phenylsulfonyl)benzyl)guanidine

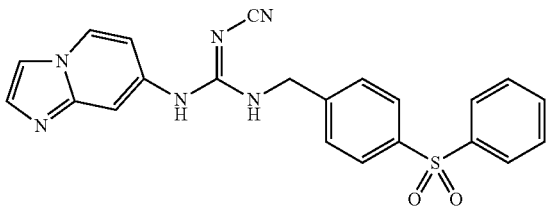 [SMILES: N#C/N=C(\NCc1ccc(S(=O)(=O)c2ccccc2)cc1)Nc1ccn2ccnc2c1]

In a 50 mL round-bottomed flask was added (Z)-methyl N'-cyano-N-(imidazo[1,2-a]pyridin-7-yl)carbamimidothioate (200 mg, 0.865 mmol), (4-(phenylsulfonyl)phenyl)methanamine (214 mg, 0.865 mmol), DMAP (10.56 mg, 0.086 mmol) and TEA (0.241 mL, 1.730 mmol) in Pyridine (Volume: 10 mL) followed by heating the mixture overnight to 70° C. The reaction was monitored by LCMS and then concentrated under reduced pressure and purified directly on the Biotage to give 281 mg of product plus starting amine (NMR FT00239-29-A). Material purified again on Biotage again to give the title compound.

$^1$H NMR (DMSO-d$_6$): δ 9.39 (br. s, 1H), 8.46 (d, 1H), 7.86-8.00 (m, 6H), 7.56-7.68 (m, 3H), 7.50 (m, 3H), 7.33 (d, 1H), 6.80 (dd, 1H), 4.44 (d, 2H);

LC-MS (ESI): 445.15 (M+1).

Example 3

2-cyano-1-(imidazo[1,2-a]pyridin-7-ylmethyl)-3-(4-(phenylsulfonyl)benzyl)guanidine

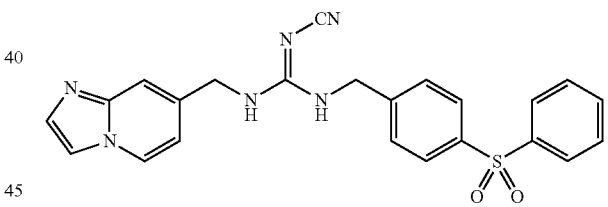

A: methyl N'-cyano-N-(imidazo[1,2-a]pyridin-7-ylmethyl)carbamimidothioate

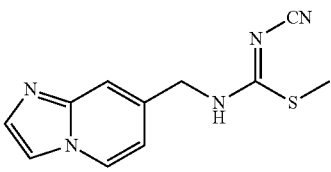 [SMILES: CS/C(=N\C#N)NCc1ccn2ccnc2c1]

In a 50 mL round-bottomed flask was added imidazo[1,2-a]pyridin-7-ylmethanamine (500 mg, 3.40 mmol), dimethyl cyanocarbonimidodithioate (621 mg, 4.25 mmol), DMAP (41.5 mg, 0.340 mmol) and DIEA (1.187 mL, 6.79 mmol) in Pyridine (Volume: 20 mL) followed by heating the mixture to 60° C. The reaction was stirred overnight and then cooled to room temperature. Methylene chloride was then added to the slurry and the mixture filtered and washed with methylene chloride to give the title compound.

¹H NMR (300 MHz, DMSO-d₆): δ 8.86 (br. S, 1H), 8.47 (s, 1H), 9.97 (s, 1H), 7.54 (m, 2H), 7.19 (dd, 1H), 4.41 (s, 2H), 2.61 (3H);

LC-MS (ESI): 246.10 (M+1).

B: 2-cyano-1-(imidazo[1,2-a]pyridin-7-ylmethyl)-3-(4-(phenylsulfonyl)benzyl)guanidine

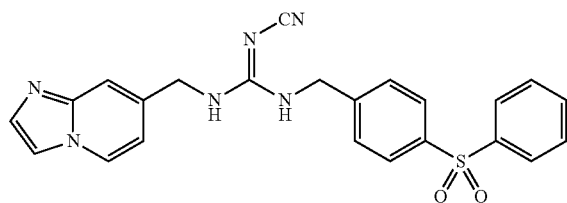 [SMILES: N#C/N=C(\NCc1ccc(S(=O)(=O)c2ccccc2)cc1)NCc1ccn2ccnc2c1]

In a 50 mL round-bottomed flask was added (Z)-methyl N'-cyano-N-(imidazo[1,2-a]pyridin-7-ylmethyl)carbamimidothioate (400 mg, 1.631 mmol), (4-(phenylsulfonyl)phenyl)methanamine (403 mg, 1.631 mmol), DMAP (19.92 mg, 0.163 mmol) and triethylamine (0.500 mL, 3.59 mmol) in Pyridine (Volume: 10 mL) followed by warming the reaction to 100° C. overnight. The reaction was then cooled, diluted with methylene chloride and filtered. The solid was washed with methylene chloride and then dried under vacuum to give 319.5 mg of starting cyanoimidate material. LCMS of the mother liquor only showed a trace of product. Took recovered material and added 1 eq. of benzyl amine, 2 eq. of triethylamine and catalytic DMAP in pyridine and refluxed overnight. LCMS showed approx. 50% completion, so continued heating over weekend to force completion. Reaction concentrated under reduced pressure and purified on Biotage to give 262.0 mg of product with minor impurity. Triturated material with methylene chloride and filtered to give the title compound.

¹H NMR (DMSO-d₆): δ 8.30 (s, 1H), 7.84-7.93 (m, 5H), 7.74 (t, 1H), 7.54-7.68 (m, 5H), 7.47 (d, 1H), 7.38 (d, 2H), 7.05 (d, 1H), 4.39 (d, 2H), 4.30 (d, 2H);

LC-MS (ESI): 445.15 (M+1).

Example 4

3-({4-[(3-chlorobenzene)sulfonyl]phenyl}methyl)-2-cyano-1-(pyridin-4-yl)guanidine

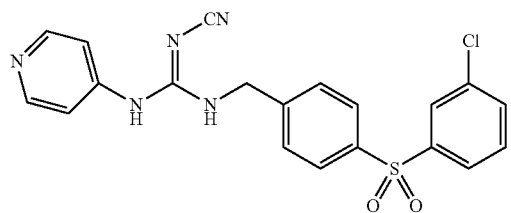 [SMILES: N#C/N=C(\NCc1ccc(S(=O)(=O)c2cccc(Cl)c2)cc1)Nc1ccncc1]

A: sodium 4-(acetamidomethyl)benzenesulfinate

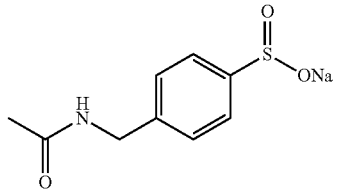

4-(Acetamidomethyl)benzene-1-sulfonyl chloride (1.24 g, 5 mmol) was added to a water-cooled solution of Na₂SO₃ (1.89 g, 15 mmol) in water (3.75 mL) then solid NaHCO₃ (850 mg, 10 mmol) was added in several small portions to keep the pH slightly basic. The mixture was stirred at ambient temperature for 2 hours, affording a thick white suspension. Brine (2 ml) was added and the mixture was stirred at ambient temperature for 15 minutes. The precipitate was collected by filtration and dried overnight under vacuum. The solid was ground up and stirred with 125 ml of MeOH for 30 min then the solid was filtered off, washing with MeOH (20 mL). The filtrate was concentrated to give the title compound as a white solid.

¹H NMR (400 MHz, CD₃OD): δ 7.61 (d, J=8.4 Hz, 2H), 7.34 (d, J=8.4 Hz, 2H), 4.38 (s, 2H), 1.98 (s, 3H).

B: (4-(3-chlorophenylsulfonyl)phenyl)methanamine

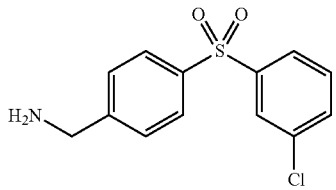 [SMILES: NCc1ccc(S(=O)(=O)c2cccc(Cl)c2)cc1]

A mixture of sodium 4-(acetamidomethyl)benzenesulfinate (23.5 mg, 0.1 mmol), 3-chlorobenzeneboronic acid (19.5 mg, 0.125 mmol), copper(II) acetate (22.7 mg, 0.125 mmol), and TEA (0.063 mL, 0.45 mmol) in DMSO (1.5 mL) was heated at 60° C. for 16 hours. The mixture was cooled to room temperature and partitioned between EtOAc-brine. The organic layer was separated and concentrated in vacuo. The crude was purified by PTLC (100% EtOAc) to afford the title compound as white solid which was mixed with 3N HCl (0.36 mL, 1.08 mmol) in 70% i-PrOH (0.2 mL) and heated at 100° C. for 5 hours. The mixture was concentrated to dryness to afford the title compound.

¹H NMR (300 HMz; DMSO-d₆): δ 8.04-8.10 (m, 2H), 8.01 (t, 1H), 7.91-7.94 (m, 1H), 7.74-7.78 (m, 1H), 7.61-7.69 (m, 3H), 4.11 (b, 2H).

C: 3-({4-[(3-chlorobenzene)sulfonyl]phenyl}methyl)-2-cyano-1-(pyridin-4-yl)guanidine

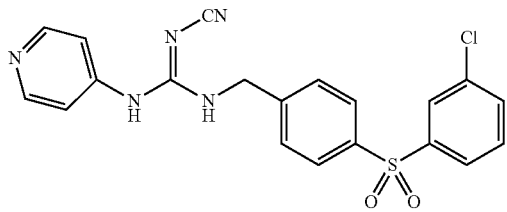 [SMILES: N#C/N=C(\NCc1ccc(S(=O)(=O)c2cccc(Cl)c2)cc1)Nc1ccncc1]

In a 100 ml flask was added methyl N'-cyano-N-(pyridin-4-yl)carbamimidothioate (1 g, 5.2 mmol) and (4-(3-chlorophenylsulfonyl)phenyl)methanamine trifluoro acetic acid (2.66 g, 6.76 mmol) in 50 ml of pyridine followed by addition of triethylamine (2.17 ml, 15.6 mmol) and N,N-dimethylpyridin-4-amine (32 mg). The mixture was heated to 60° C. for 16 hours. The mixture was concentrated and purified directly by the biotage to afford 1.224 g of product.

$^1$H NMR (300 HMz; DMSO-$d_6$): δ 9.63 (br s, 1H), 8.37 (m, 3H), 7.96-8.03 (m, 3H), 7.89-7.98 (m, 1H), 7.73-7.76 (m, 1H), 7.60-7.65 (m, 1H), 7.54-7.55 (d, 2H), 7.17 (s, 2H), 4.52 (d, 2H).

LC-MS: 426.18 (M+1).

Example 5

(E)-1-(4-(benzylsulfonyl)benzyl)-2-cyano-3-(pyridin-4-yl)guanidine

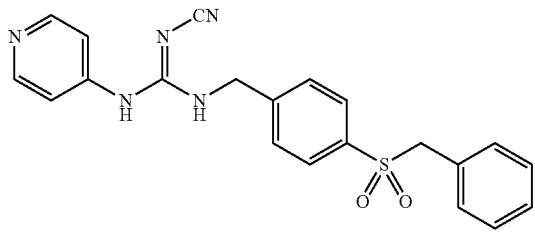 [SMILES: N#C/N=C(\NCc1ccc(S(=O)(=O)Cc2ccccc2)cc1)Nc1ccncc1]

A: N-(4-(benzylsulfonyl)benzyl)acetamide

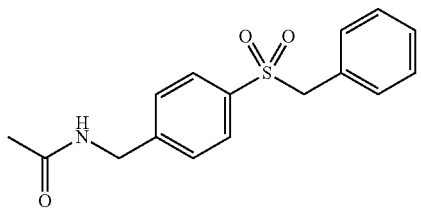 [SMILES: CC(=O)NCc1ccc(S(=O)(=O)Cc2ccccc2)cc1]

To a solution of sodium 4-(acetamidomethyl)benzenesulfinate (1 g, 4.25 mmol) in water (12 mL) were added tetrabutylammonium iodide (TBAI) (0.157 g, 0.425 mmol) and (bromomethyl)benzene (0.742 g, 4.34 mmol) under $N_2$ flow. The reaction mixture was heated to 70° C. for 2 h. The white solids were precipitated out. LC-MS analysis indicated that the reaction was completed. The white solids were filtered and washed with water and diethyl ether, then dried under reduced pressure to give 696 mg of desired product with 90% HPLC purity. The crude product was ready for next step without further purification.

$^1$H NMR (300 MHz, CDCl$_3$) δ 7.54 (d, 2H), 7.33-7.24 (d, 5H), 7.08 (d, 2H), 5.94 (bs, 1H), 4.50 (d, 2H), 4.29 (s, 2H), 2.07 (s, 3H).

LC-MS (ESI): M+H=304.12.

B: (4-(benzylsulfonyl)phenyl)methanamine

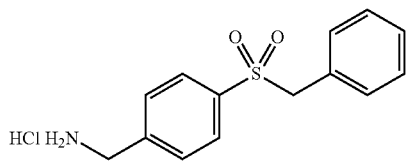

A mixture of N-(4-(benzylsulfonyl)benzyl)acetamide (300 mg, 0.989 mmol) and 3N HCl (11.87 ml, 35.6 mmol) in $^i$PrOH (12 mL) was heated to 100° C. The cloudy mixture turned to a clear solution as temperature was elevated. The reaction mixture was stirred for 16 h at 100° C. The white solids were precipitated after the mixture was cooled to room temperature. The solids were filtered and washed with a small amount of cold water and ether, then filtered and dried under reduced pressure, yielding the title compound as hydrochloride salt.

$^1$H NMR (300 MHz, DMSO-$d_6$) δ 8.44 (bs, 3H), 7.75 (d, 2H), 7.66 (d, 2H), 7.29 (m, 3H), 7.15 (m, 2H), 4.69 (s, 2H), 4.12 (s, 2H).

LC-MS (ESI): M+H=262.11.

C: (E)-1-(4-(benzylsulfonyl)benzyl)-2-cyano-3-(pyridin-4-yl)guanidine

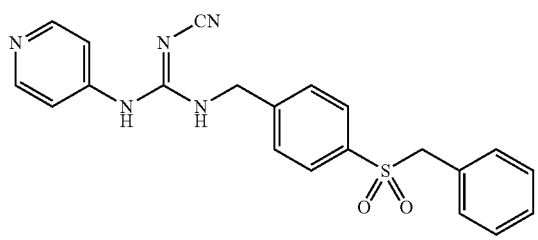 [SMILES: N#C/N=C(\NCc1ccc(S(=O)(=O)Cc2ccccc2)cc1)Nc1ccncc1]

In a 50 mL round-bottomed flask was added (Z)-methyl N'-cyano-N-(pyridin-4-yl)carbamimidothioate (47.6 mg, 0.248 mmol), (4-(benzylsulfonyl)phenyl)methanamine (65 mg, 0.249 mmol), DMAP (3.02 mg, 0.025 mmol) and TEA (0.069 ml, 0.495 mmol) in pyridine (10 mL) followed by heating the mixture overnight at 80° C. The reaction was monitored by LC-MS and then concentrated under reduced pressure. The residue was dissolved in dichloromethane and purified on a Biotage to give the title compound (31.6 mg, 32% yield).

$^1$H NMR (DMSO-$d_6$): δ 9.62 (s, 1H), 8.41 (s, 3H), 7.68 (d, 2H), 7.48 (d, 2H), 7.26-7.21 (m, 5H), 7.11 (d, 2H), 4.64 (s, 2H), 4.54 (d, 2H).

LCMS (ESI): M+H=406.22.

Assays

Assay Example 1

Biochemical Inhibition Assay
NAMPT Protein Purification

Recombinant His-tagged NAMPT was produced in *E. coli* cells, purified over a Ni column, and further purified over a size-exclusion column by XTAL Biostructures.
The NAMPT Enzymatic Reaction The NAMPT enzymatic reactions were carried out in Buffer A (50 mM Hepes pH 7.5, 50 mM NaCl, 5 mM $MgCl_2$, and 1 mM THP) in 96-well V-bottom plates. The compound titrations were performed in a separate dilution plate by serially diluting the compounds in DMSO to make a 100× stock. Buffer A (89 µL) containing 33 nM of NAMPT protein was added to 1 µL of 100× compound plate containing controls (e.g. DMSO or blank). The compound and enzyme mix was incubated for 15 minutes at room temperature, then 10 µL of 10× substrate and co-factors in Buffer A were added to the test well to make a final concentration of 1 µM NAM, 100 µM 5-Phospho-D-ribose 1-diphosphate (PRPP), and 2.5 mM Adenosine 5'-triphosphate (ATP). The reaction was allowed to proceed for 30 minutes at room temperature, then was quenched with the addition of 11 µL of a solution of formic acid and L-Cystathionine to make a final concentration of 1% formic acid and 10 µM L-Cystathionine. Background and signal strength was determined by addition (or non-addition) of a serial dilution of NMN to a pre-quenched enzyme and cofactor mix.
Quantification of NMN A mass spectrometry-based assay was used to measure the NAMPT reaction product (NMN) and the internal control (L-Cystathionine). NMN and L-Cystathionine were detected using the services of Biocius Lifesciences with the RapidFire system. In short, the NMN and L-Cystathionine are bound to a graphitic carbon cartridge in 0.1% formic acid, eluted in 30% acetonitrile buffer, and injected into a Sciex 4000 mass spectrometer. The components of the sample were ionized with electrospray ionization and the positive ions were detected. The Q1 (parent ion) and Q3 (fragment ion) masses of NMN were 334.2 and 123.2, respectively. The Q1 and Q3 for L-Cystathionine were 223.1 and 134.1, respectively. The fragments are quantified and the analyzed by the following method.

% Inhibitions are Determined Using this Method.

First the NMN signal is normalized to the L-Cystathionine signal by dividing the NMN signal by the L-Cystathionine signal for each well. The signal from the background wells are averaged and subtracted from the test plates. The compound treated cells re then assayed for % inhibition by using this formula.

$$\%Inh=100-100*x/y$$

wherein x denotes the average signal of the compound treated wells and y denotes the average signal of the DMSO treated wells.
IC50s are Determined Using Excel and this Formula.

$$IC50=10^{\wedge}(LOG\ 10(X)+(((50-\%Inh\ at\ Cmpd\ Concentration\ 1)/(XX-YY)*(LOG\ 10(X)-LOG\ 10(Y))))$$

wherein X denotes the compound concentration 1, Y denotes the compound concentration 2, XX denotes the % inhibition at compound concentration 1 (X), and YY denotes the % inhibition at compound concentration 2 (Y).
The NAMPT-inhibitor compounds of this invention have IC50 values that are below 10 µM, preferably below 1 µM, more preferably below 0.1 µM and most preferably below 0.01 µM. Results for the compounds are provided below in Table 3.

Assay Example 2

In-Vitro Cell Proliferation Assay

A2780 cells were seeded in 96-well plates at $1\times10^3$ cells/well in 180 µL of culture medium (10% FBS, 1% Pen/Strep Amphotecricin B, RPMI-1640) with and without the addition of either β-nicotinamide mononucleotide (NMN) or nicotinamide (NAM). After overnight incubation at 37° C. and 5% $CO_2$, the compound titrations were performed in a separate dilution plate by serially diluting the compounds in DMSO to make a 1000× stock. The compounds were then further diluted to 10× final concentration in culture media, whereupon 20 µL of each dilution was added to the plated cells with controls (e.g. DMSO and blank) to make a final volume of 200 µL. The final DMSO concentration in each well was 0.1%. The plates were then incubated for 72 hours at 37° C. in a 5% $CO_2$ incubator. The number of viable cells was then assessed using sulforhodamine B (SRB) assay. Cells were fixed at 4° C. for 1 hour with the addition of 50 µL 30% trichloroacetic acid (TCA) to make a final concentration of 6% TCA. The plates were washed four times with $H_2O$ and allowed to dry for at least 1 hour, whereupon 100 µL of a 4% SRB in 1% acetic acid solution was added to each well and incubated at room temperature for at least 30 minutes. The plates were then washed three times with 1% acetic acid, dried, and treated with 100 µL of 10 mM Tris-Base solution. The plates were then read in a microplate reader at an absorbance of 570 nm. Background was generated on a separate plate with media only.
Method for Determining % Inhibition
First, the signals from the background plate are averaged, then the background was subtracted from the test plates. The compound-treated cells were then assayed for % inhibition by using the following formula:

$$\%Inh=100-100*x/y$$

wherein x denotes the average signal of the compound-treated cells and y denotes the average signal of the DMSO-treated cells.
Formula for Determining $IC_{50}$ Values:

$$IC50=10^{\wedge}(LOG\ 10(X)+(((50-\%\ Inh\ at\ Cmpd\ Concentration\ 1)/(XX-YY)*(LOG\ 10(X)-LOG\ 10(Y))))$$

wherein X denotes the compound concentration 1, Y denotes the compound concentration 2, XX denotes the % inhibition at compound concentration 1 (X), and YY denotes the % inhibition at compound concentration 2 (Y).
Specificity of Cytotoxicity.

Inhibition of NAMPT could be reversed by the addition of NAM or NMN. The specificity of the compounds were determined via cell viability assay in the presence of the compound and either NAM or NMN. Percent inhibitions were determined using the method given above.
The NAMPT-inhibitor compounds of this invention have IC50 values that are below 10 µM, preferably below 1 µM, more preferably below 0.1 µM and most preferably below 0.01 µM. Results for the compounds are provided below in Table 3.

TABLE 3

| Compound | Biochem IC50 uM | A2780 IC50 uM |
| --- | --- | --- |
| (E)-3-({4-[(3-chlorobenzene)sulfonyl]phenyl}methyl)-2-cyano-1-(pyridin-4-yl)guanidine | 0.0026 | 0.0041 |
| (E)-3-{[4-(benzenesulfonyl)phenyl]methyl}-2-cyano-1-(pyridin-3-ylmethyl)guanidine | 0.017 | 0.678 |
| 1-({4-[(3-chloro-4-methoxybenzene)sulfonyl]phenyl}methyl)-2-cyano-3-(pyridin-4-yl)guanidine | 0.0026 | 0.0049 |
| 1-({4-[(3-chloro-4-methylbenzene)sulfonyl]phenyl}methyl)-2-cyano-3-(pyridin-4-yl)guanidine | 0.0019 | 0.0016 |
| 1-({4-[(3-chloro-4-propoxybenzene)sulfonyl]phenyl}methyl)-2-cyano-3-(pyridin-4-yl)guanidine | 0.0049 | 0.0058 |
| 1-({4-[(3-chloro-5-fluorobenzene)sulfonyl]phenyl}methyl)-2-cyano-3-(pyridin-4-yl)guanidine | 0.0051 | 0.0069 |
| 1-({4-[(3-chloro-5-methoxybenzene)sulfonyl]phenyl}methyl)-2-cyano-3-(pyridin-4-yl)guanidine | 0.0046 | 0.0016 |
| 1-({4-[(3-chloro-5-methylbenzene)sulfonyl]phenyl}methyl)-2-cyano-3-(pyridin-4-yl)guanidine | 0.0033 | 0.0016 |
| 1-({4-[(4-acetylbenzene)sulfonyl]phenyl}methyl)-2-cyano-3-(pyridin-4-yl)guanidine | 0.0050 | 0.0073 |
| 1-({4-[(4-chloro-2-methoxybenzene)sulfonyl]phenyl}methyl)-2-cyano-3-(pyridin-4-yl)guanidine | 0.0030 | 0.0019 |
| 1-({4-[(4-chloro-3-fluorobenzene)sulfonyl]phenyl}methyl)-2-cyano-3-(pyridin-4-yl)guanidine | 0.0020 | 0.0019 |
| 1-({4-[(4-chlorobenzene)sulfonyl]phenyl}methyl)-2-cyano-3-(pyridin-4-yl)guanidine | 0.0036 | 0.0037 |
| 1-({4-[(5-acetyl-2-methoxybenzene)sulfonyl]phenyl}methyl)-2-cyano-3-(pyridin-4-yl)guanidine | 0.0146 | 0.0417 |
| 1-({4-[(5-chloro-2-methoxybenzene)sulfonyl]phenyl}methyl)-2-cyano-3-(pyridin-4-yl)guanidine | 0.0050 | 0.0064 |
| 1-({4-[3-chloro-2-(morpholin-4-yl)pyridine-4-sulfonyl]phenyl}methyl)-2-cyano-3-(pyridin-4-yl)guanidine | 0.0034 | 0.0041 |
| 1-[(4-{[3-chloro-5-(trifluoromethyl)benzene]sulfonyl}phenyl)methyl]-2-cyano-3-(pyridin-4-yl)guanidine | 0.0033 | 0.0016 |
| 1-[(4-{[4-chloro-3-(trifluoromethyl)benzene]sulfonyl}phenyl)methyl]-2-cyano-3-(pyridin-4-yl)guanidine | 0.0010 | 0.0015 |
| 1-[4-(benzenesulfonyl)phenyl]-2-cyano-3-(pyridin-3-ylmethyl)guanidine | 0.032 | 2.709 |
| 1-{[4-(2H-1,3-benzodioxole-4-sulfonyl)phenyl]methyl}-2-cyano-3-(pyridin-4-yl)guanidine | 0.0051 | 0.0094 |
| 1-{[4-(2H-1,3-benzodioxole-5-sulfonyl)phenyl]methyl}-2-cyano-3-(pyridin-4-yl)guanidine | 0.0018 | 0.0033 |
| 1-{2-[4-(benzenesulfonyl)phenyl]ethyl}-2-cyano-3-(pyridin-4-yl)guanidine | 0.001 | 0.0053 |
| 2-cyano-1-({4-[(2,3-dimethylbenzene)sulfonyl]phenyl}methyl)-3-(pyridin-4-yl)guanidine | 0.0040 | 0.0035 |
| 2-cyano-1-({4-[(2,4-dimethylbenzene)sulfonyl]phenyl}methyl)-3-(pyridin-4-yl)guanidine | 0.0024 | 0.0015 |
| 2-cyano-1-({4-[(2-ethoxybenzene)sulfonyl]phenyl}methyl)-3-(pyridin-4-yl)guanidine | 0.0071 | 0.0035 |
| 2-cyano-1-({4-[(2-methoxybenzene)sulfonyl]phenyl}methyl)-3-(pyridin-4-yl)guanidine | 0.0072 | 0.0039 |
| 2-cyano-1-({4-[(2-methylbenzene)sulfonyl]phenyl}methyl)-3-(pyridin-4-yl)guanidine | 0.0079 | 0.0056 |
| 2-cyano-1-({4-[(3,4-dichlorobenzene)sulfonyl]phenyl}methyl)-3-(pyridin-4-yl)guanidine | 0.0017 | 0.0010 |
| 2-cyano-1-({4-[(3,4-difluorobenzene)sulfonyl]phenyl}methyl)-3-(pyridin-4-yl)guanidine | 0.0008 | 0.0025 |
| 2-cyano-1-({4-[(3,4-dimethoxybenzene)sulfonyl]phenyl}methyl)-3-(pyridin-4-yl)guanidine | 0.0040 | 0.0034 |
| 2-cyano-1-({4-[(3,4-dimethylbenzene)sulfonyl]phenyl}methyl)-3-(pyridin-4-yl)guanidine | 0.0022 | 0.0012 |
| 2-cyano-1-({4-[(3,5-dichlorobenzene)sulfonyl]phenyl}methyl)-3-(pyridin-4-yl)guanidine | 0.0112 | 0.0016 |

TABLE 3-continued

| Compound | Biochem IC50 uM | A2780 IC50 uM |
| --- | --- | --- |
| 2-cyano-1-({4-[(3,5-difluorobenzene)sulfonyl]phenyl}methyl)-3-(pyridin-4-yl)guanidine | 0.001 | 0.002 |
| 2-cyano-1-({4-[(3,5-dimethylbenzene)sulfonyl]phenyl}methyl)-3-(pyridin-4-yl)guanidine | 0.0033 | 0.0016 |
| 2-cyano-1-({4-[(3-cyanobenzene)sulfonyl]phenyl}methyl)-3-(pyridin-4-yl)guanidine | 0.0017 | 0.0062 |
| 2-cyano-1-({4-[(3-ethoxybenzene)sulfonyl]phenyl}methyl)-3-(pyridin-4-yl)guanidine | 0.0043 | 0.0065 |
| 2-cyano-1-({4-[(3-fluoro-4-methoxybenzene)sulfonyl]phenyl}methyl)-3-(pyridin-4-yl)guanidine | 0.001 | 0.002 |
| 2-cyano-1-({4-[(3-fluoro-4-methylbenzene)sulfonyl]phenyl}methyl)-3-(pyridin-4-yl)guanidine | 0.0148 | 0.0062 |
| 2-cyano-1-({4-[(3-fluoro-5-methoxybenzene)sulfonyl]phenyl}methyl)-3-(pyridin-4-yl)guanidine | 0.0023 | 0.0021 |
| 2-cyano-1-({4-[(3-fluoro-5-methylbenzene)sulfonyl]phenyl}methyl)-3-(pyridin-4-yl)guanidine | 0.0017 | 0.0033 |
| 2-cyano-1-({4-[(3-fluorobenzene)sulfonyl]phenyl}methyl)-3-(pyridin-4-yl)guanidine | 0.0032 | 0.0145 |
| 2-cyano-1-({4-[(3-methoxy-4-methylbenzene)sulfonyl]phenyl}methyl)-3-(pyridin-4-yl)guanidine | 0.0012 | 0.0008 |
| 2-cyano-1-({4-[(3-methoxybenzene)sulfonyl]phenyl}methyl)-3-(pyridin-4-yl)guanidine | 0.0015 | 0.0034 |
| 2-cyano-1-({4-[(3-methylbenzene)sulfonyl]phenyl}methyl)-3-(pyridin-4-yl)guanidine | 0.0052 | 0.0046 |
| 2-cyano-1-({4-[(4-cyanobenzene)sulfonyl]phenyl}methyl)-3-(pyridin-4-yl)guanidine | 0.0059 | 0.0137 |
| 2-cyano-1-({4-[(4-ethoxy-3-fluorobenzene)sulfonyl]phenyl}methyl)-3-(pyridin-4-yl)guanidine | 0.0060 | 0.0032 |
| 2-cyano-1-({4-[(4-ethoxybenzene)sulfonyl]phenyl}methyl)-3-(pyridin-4-yl)guanidine | 0.0056 | 0.0033 |
| 2-cyano-1-({4-[(4-ethylbenzene)sulfonyl]phenyl}methyl)-3-(pyridin-4-yl)guanidine | 0.0047 | 0.0015 |
| 2-cyano-1-({4-[(4-fluoro-2-methylbenzene)sulfonyl]phenyl}methyl)-3-(pyridin-4-yl)guanidine | 0.0054 | 0.0054 |
| 2-cyano-1-({4-[(4-fluoro-3-methylbenzene)sulfonyl]phenyl}methyl)-3-(pyridin-4-yl)guanidine | 0.0031 | 0.0039 |
| 2-cyano-1-({4-[(4-methanesulfonylbenzene)sulfonyl]phenyl}methyl)-3-(pyridin-4-yl)guanidine | 0.0045 | 0.0131 |
| 2-cyano-1-({4-[(4-methoxy-3-methylbenzene)sulfonyl]phenyl}methyl)-3-(pyridin-4-yl)guanidine | 0.0204 | 0.0150 |
| 2-cyano-1-({4-[(4-methoxybenzene)sulfonyl]phenyl}methyl)-3-(pyridin-4-yl)guanidine | 0.0065 | 0.0100 |
| 2-cyano-1-({4-[(4-methylbenzene)sulfonyl]phenyl}methyl)-3-(pyridin-4-yl)guanidine | 0.0025 | 0.0026 |
| 2-cyano-1-({4-[(4-phenylbenzene)sulfonyl]phenyl}methyl)-3-(pyridin-4-yl)guanidine | 0.0035 | 0.0062 |
| 2-cyano-1-({4-[(5-fluoro-2-methylbenzene)sulfonyl]phenyl}methyl)-3-(pyridin-4-yl)guanidine | 0.0045 | 0.0033 |
| 2-cyano-1-({4-[2-(dimethylamino)pyrimidine-5-sulfonyl]phenyl}methyl)-3-(pyridin-4-yl)guanidine | 0.0086 | 0.0070 |
| 2-cyano-1-({4-[6-(morpholin-4-yl)pyridine-3-sulfonyl]phenyl}methyl)-3-(pyridin-4-yl)guanidine | 0.0019 | 0.0033 |
| 2-cyano-1-(pyridin-4-yl)-3-[(4-{[2-(trifluoromethoxy)benzene]sulfonyl}phenyl)methyl]guanidine | 0.004 | 0.0006 |
| 2-cyano-1-[(4-{[2-(morpholin-4-ylmethyl)benzene]sulfonyl}phenyl)methyl]-3-(pyridin-4-yl)guanidine | 0.0117 | 0.0075 |
| 2-cyano-1-[(4-{[2-methoxy-4-(trifluoromethyl)benzene]sulfonyl}phenyl)methyl]-3-(pyridin-4-yl)guanidine | 0.0057 | 0.0060 |
| 2-cyano-1-[(4-{[2-methoxy-5-(propan-2-yl)benzene]sulfonyl}phenyl)methyl]-3-(pyridin-4-yl)guanidine | 0.0053 | 0.0035 |

TABLE 3-continued

| Compound | Biochem IC50 uM | A2780 IC50 uM |
|---|---|---|
| 2-cyano-1-[(4-{[3-(1H-pyrazol-1-yl)benzene]sulfonyl}phenyl)methyl]-3-(pyridin-4-yl)guanidine | 0.0035 | 0.0029 |
| 2-cyano-1-[(4-{[3-(3,5-dimethyl-1H-pyrazol-1-yl)benzene]sulfonyl}phenyl)methyl]-3-(pyridin-4-yl)guanidine | 0.0030 | 0.0030 |
| 2-cyano-1-[(4-{[3-(dimethylsulfamoyl)benzene]sulfonyl}phenyl)methyl]-3-(pyridin-4-yl)guanidine | 0.0013 | 0.0061 |
| 2-cyano-1-[(4-{[3-(ethanesulfonyl)benzene]sulfonyl}phenyl)methyl]-3-(pyridin-4-yl)guanidine | 0.0018 | 0.0133 |
| 2-cyano-1-[(4-{[3-(methoxymethyl)benzene]sulfonyl}phenyl)methyl]-3-(pyridin-4-yl)guanidine | 0.0072 | 0.0059 |
| 2-cyano-1-[(4-{[3-(propan-2-yl)benzene]sulfonyl}phenyl)methyl]-3-(pyridin-4-yl)guanidine | 0.0029 | 0.0011 |
| 2-cyano-1-[(4-{[3-(propan-2-yloxy)benzene]sulfonyl}phenyl)methyl]-3-(pyridin-4-yl)guanidine | 0.0032 | 0.0057 |
| 2-cyano-1-[(4-{[3-(propane-1-sulfonamido)benzene]sulfonyl}phenyl)methyl]-3-(pyridin-4-yl)guanidine | 0.0021 | 0.0233 |
| 2-cyano-1-[(4-{[3-fluoro-4-(1H-pyrazol-1-yl)benzene]sulfonyl}phenyl)methyl]-3-(pyridin-4-yl)guanidine | 0.0061 | 0.0094 |
| 2-cyano-1-[(4-{[3-fluoro-4-(2,2,2-trifluoroethoxy)benzene]sulfonyl}phenyl)methyl]-3-(pyridin-4-yl)guanidine | 0.0051 | 0.0059 |
| 2-cyano-1-[(4-{[3-fluoro-5-(2,2,2-trifluoroethoxy)benzene]sulfonyl}phenyl)methyl]-3-(pyridin-4-yl)guanidine | 0.0053 | 0.0019 |
| 2-cyano-1-[(4-{[3-fluoro-5-(trifluoromethyl)benzene]sulfonyl}phenyl)methyl]-3-(pyridin-4-yl)guanidine | 0.0060 | 0.0015 |
| 2-cyano-1-[(4-{[4-(1H-pyrazol-1-yl)benzene]sulfonyl}phenyl)methyl]-3-(pyridin-4-yl)guanidine | 0.0033 | 0.0034 |
| 2-cyano-1-[(4-{[4-(morpholin-4-yl)benzene]sulfonyl}phenyl)methyl]-3-(pyridin-4-yl)guanidine | 0.0015 | 0.0028 |
| 2-cyano-1-[(4-{[4-(propan-2-yl)benzene]sulfonyl}phenyl)methyl]-3-(pyridin-4-yl)guanidine | 0.0038 | 0.0028 |
| 2-cyano-1-[(4-{[4-(propan-2-yloxy)benzene]sulfonyl}phenyl)methyl]-3-(pyridin-4-yl)guanidine | 0.0026 | 0.0015 |
| 2-cyano-1-{[4-({3-[(morpholin-4-yl)carbonyl]benzene}sulfonyl)phenyl]methyl}-3-(pyridin-4-yl)guanidine | 0.0017 | 0.0705 |
| 2-cyano-1-{[4-(1-methyl-1H-indazole-6-sulfonyl)phenyl]methyl}-3-(pyridin-4-yl)guanidine | 0.0010 | 0.0016 |
| 2-cyano-1-{[4-(1-methyl-1H-indole-2-sulfonyl)phenyl]methyl}-3-(pyridin-4-yl)guanidine | 0.0021 | 0.0012 |
| 2-cyano-1-{[4-(1-methyl-1H-pyrazole-4-sulfonyl)phenyl]methyl}-3-(pyridin-4-yl)guanidine | 0.0043 | 0.0493 |
| 2-cyano-1-{[4-(1-propyl-1H-pyrazole-4-sulfonyl)phenyl]methyl}-3-(pyridin-4-yl)guanidine | 0.0041 | 0.0064 |
| 2-cyano-1-{[4-(2,6-dimethoxypyridine-3-sulfonyl)phenyl]methyl}-3-(pyridin-4-yl)guanidine | 0.0068 | 0.0034 |
| 2-cyano-1-{[4-(2-methylpyridine-3-sulfonyl)phenyl]methyl}-3-(pyridin-4-yl)guanidine | 0.0048 | 0.0075 |
| 2-cyano-1-{[4-(4-methylpyridine-3-sulfonyl)phenyl]methyl}-3-(pyridin-4-yl)guanidine | 0.0023 | 0.0085 |
| 2-cyano-1-{[4-(5-fluoropyridine-3-sulfonyl)phenyl]methyl}-3-(pyridin-4-yl)guanidine | 0.0052 | 0.0119 |
| 2-cyano-1-{[4-(5-methoxypyridine-3-sulfonyl)phenyl]methyl}-3-(pyridin-4-yl)guanidine | 0.0043 | 0.0091 |
| 2-cyano-1-{[4-(6-methylpyridine-3-sulfonyl)phenyl]methyl}-3-(pyridin-4-yl)guanidine | 0.0014 | 0.0063 |
| 2-cyano-1-{[4-(naphthalene-1-sulfonyl)phenyl]methyl}-3-(pyridin-4-yl)guanidine | 0.0038 | 0.0030 |
| 2-cyano-3-({4-[(4-fluorobenzene)sulfonyl]phenyl}methyl)-1-(pyridin-4-yl)guanidine | 0.002 | 0.013 |
| 2-cyano-3-(pyridin-4-yl)-1-[(4-{[3-(trifluoromethoxy)benzene]sulfonyl}phenyl)methyl]guanidine | 0.0062 | 0.0033 |

TABLE 3-continued

| Compound | Biochem IC50 uM | A2780 IC50 uM |
| --- | --- | --- |
| 2-cyano-3-(pyridin-4-yl)-1-[(4-{[3-(trifluoromethyl)benzene]sulfonyl}phenyl)methyl]guanidine | 0.0025 | 0.0012 |
| 2-cyano-3-(pyridin-4-yl)-1-[(4-{[4-(trifluoromethoxy)benzene]sulfonyl}phenyl)methyl]guanidine | 0.0035 | 0.0118 |
| 2-cyano-3-(pyridin-4-yl)-1-[(4-{[4-(trifluoromethyl)benzene]sulfonyl}phenyl)methyl]guanidine | 0.0163 | 0.0076 |
| 2-cyano-3-(pyridin-4-yl)-1-{[4-({4-[(pyrrolidin-1-yl)carbonyl]benzene}sulfonyl)phenyl]methyl}guanidine | 0.0048 | 0.0134 |
| 2-cyano-3-(pyridin-4-yl)-1-{[4-(pyridine-3-sulfonyl)phenyl]methyl}guanidine | 0.0207 | 0.0669 |
| 2-cyano-3-(pyridin-4-yl)-1-{[4-(quinoline-3-sulfonyl)phenyl]methyl}guanidine | 0.0010 | 0.0018 |
| 2-cyano-3-(pyridin-4-yl)-1-{[4-(quinoline-6-sulfonyl)phenyl]methyl}guanidine | 0.0062 | 0.0066 |
| 2-cyano-3-(pyridin-4-yl)-1-{[4-(quinoline-8-sulfonyl)phenyl]methyl}guanidine | 0.0029 | 0.0141 |
| 2-cyano-3-[(4-{8-oxa-3-azabicyclo[3.2.1]octane-3-sulfonyl}phenyl]methyl]-1-(pyridin-4-yl)guanidine | 0.003 | 0.011 |
| 3-[(4-{[2-cyano-3-(pyridin-4-yl)carbamimidamido]methyl}benzene)sulfonyl]-5-fluoro-N,N-dimethylbenzamide | 0.0046 | 0.0128 |
| 3-[(4-{[2-cyano-3-(pyridin-4-yl)carbamimidamido]methyl}benzene)sulfonyl]-N-(propan-2-yl)benzamide | 0.0043 | 0.0169 |
| 3-[(4-{[2-cyano-3-(pyridin-4-yl)carbamimidamido]methyl}benzene)sulfonyl]-N,N-diethyl-4-fluorobenzamide | 0.0177 | 0.0542 |
| 3-[(4-{[2-cyano-3-(pyridin-4-yl)carbamimidamido]methyl}benzene)sulfonyl]-N,N-dimethylbenzamide | 0.0034 | 0.0640 |
| 3-[(4-{[2-cyano-3-(pyridin-4-yl)carbamimidamido]methyl}benzene)sulfonyl]-N-cyclopentylbenzamide | 0.0066 | 0.0283 |
| 3-[(4-{[2-cyano-3-(pyridin-4-yl)carbamimidamido]methyl}benzene)sulfonyl]-N-cyclopropylbenzamide | 0.0022 | 0.0200 |
| 3-[(4-{[2-cyano-3-(pyridin-4-yl)carbamimidamido]methyl}benzene)sulfonyl]-N-ethylbenzamide | 0.0054 | 0.0270 |
| 3-{[4-(benzenesulfonyl)phenyl]methyl}-2-cyano-1-(pyridin-4-yl)guanidine | 0.002 | 0.012 |
| 3-chloro-5-[(4-{[2-cyano-3-(pyridin-4-yl)carbamimidamido]methyl}benzene)sulfonyl]-N,N-diethylbenzamide | 0.0026 | 0.0035 |
| 4-[(4-{[2-cyano-3-(pyridin-4-yl)carbamimidamido]methyl}benzene)sulfonyl]-N-ethylbenzamide | 0.0065 | 0.0658 |
| 2-cyano-1-(imidazol[1,2-a]pyridin-7-ylmethyl)-3-(4-phenylsulfonyl)benzyl)guanidine | 0.2660 | 0.3260 |
| 5-[(4-{[2-cyano-3-(pyridin-4-yl)carbamimidamido]methyl}benzene)sulfonyl]-N-methylpyridine-2-carboxamide | 0.0065 | 0.0278 |

In Vivo Xenograft Studies:

C.B-17-Igh-1b-Prkdc$^{scid}$ mice (female) were injected s.c. with 5×10$^6$ A2780 cells (NCI) in the left flank. 10-12 days later when tumors reached 100-200 mm3 in size, mice were randomized into treatment groups of 8 mice per group including vehicle control and reference standard groups. The compounds were formulated in 60:30:10 PEG-400:D5W:Ethanol and administered p.o., at the dose volume of 10 ml/kg BID for a duration of 5 or 10 days. The dose used for efficacy was selected from the MTD (Maximum Tolerated Dose) study. Mice were weighed and tumors measured using vernier calipers every alternate day. Tumor volume was calculated according to the formula (length×width$^2$)/2. All animal work was approved by the Institutional Animal Care and Use Committee of Biological Resource Centre, Singapore.

Results:
The following compounds produced tumor regression:
31494713-({4-[(3-chlorobenzene)sulfonyl]phenyl}methyl)-2-cyano-1-(pyridin-4-yl)guanidine;
31540272-cyano-3-(pyridin-4-yl)-1-[(4-{[3-trifluoromethyl)benzene]sulfonyl}phenyl)methyl]guanidine; and
31540282-cyano-3-(pyridin-4-yl)-1-[(4-{[3-(trifluoromethoxy)benzene]sulfonyl}phenyl)methyl]guanidine.
The following compound delayed tumor growth.
31430462-cyano-1-({4-[(2-ethoxybenzene)sulfonyl]phenyl}methyl)-3-(pyridin-4-yl)guanidine While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

We claim:
1. Compounds of the Formula II:

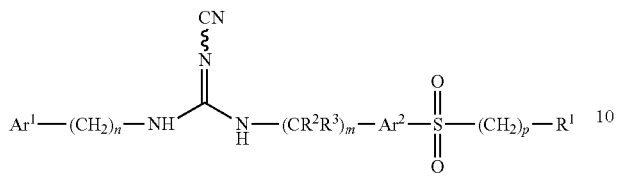

wherein
Ar¹ is unsubstituted pyridine or imidazopyridine;
Ar² is phenyl;
R¹ is cycloalkyl, aryl, heterocycloalkyl, or heteroaryl, wherein said cycloalkyl or aryl is 5 to 13 membered monocyclic or bicyclic cycloalkyl or aryl, and said heterocycloalkyl or heteroaryl is 5 to 13 membered monocyclic or bicyclic heterocycloalkyl or heteroaryl comprising 1, 2 or 3 heteroatoms selected from the group consisting of N, S and O with the proviso that no two adjacent ring heteroatoms on a ring are both S or both O; and
  (i) wherein each of said cycloalkyl, aryl, heterocycloalkyl and heteroaryl is either unsubstituted or optionally independently substituted with 1, 2, 3, 4 or 5 substituents which can be the same or different and are independently selected from the group consisting of:
    deuterium, halo, cyano, alkyl, hydroxyalkyl, cyanoalkyl, haloalkyl, alkenyl, alkynyl, alkoxy, alkylalkoxy, haloalkoxy, aryloxy, —NR$^a$R$^b$, —CONR$^a$R$^b$, —S(O)$_2$-alkyl, —S(O)$_2$-aryl, —S(O)$_2$N(alkyl)$_2$, —S(O)$_2$—CF$_3$, —C(O)alkyl, —NH—C(O)alkyl, —NH—C(O)aryl, methylenedioxy, —(CH$_2$)$_q$cycloalkyl, —(CH$_2$)$_q$aryl, —(CH$_2$)$_q$heteroaryl, and —(CH$_2$)$_q$heterocycloalkyl,
R$^a$ and R$^b$ are independently H, alkyl, alkoxy, aryl, alkoxyalkyl, —S(O)$_2$alkyl or cycloalkyl, or R$^a$ and R$^b$ can form a 5 or 6 membered heterocycloalkyl group together with the nitrogen atom to which they are attached, wherein said heterocycloalkyl group may contain one or more additional heteroatom(s) selected from the group consisting of N, S and O;
R² and R³ are H or deuterium; and
m, n, p and q are independently 0, 1 or 2;
and stereoisomers thereof;
and pharmaceutically acceptable salts thereof.

2. The compounds of claim 1, wherein Ar¹ is unsubstituted pyridine.

3. The compounds of claim 1, wherein Ar¹ is imidazopyridine.

4. The compounds of claim 1, wherein R¹ is heteroaryl that is unsubstituted or substituted by one or more substituents selected from the group consisting of halo, alkyl, alkoxy, heterocycloalkyl, —N(R$^a$R$^b$), wherein R$^a$ and R$^b$ are as defined in claim 1.

5. The compounds of claim 4, wherein the heteroaryl is 5 to 13 membered monocyclic or bicyclic heteroaryl comprising 1, 2 or 3 heteroatoms selected from the group consisting of N, S and O with the proviso that no two adjacent ring heteroatoms are both S or both O.

6. The compounds of claim 5, wherein the heteroaryl is selected from the group consisting of pyridine, quinolone, benzodioxole, and indazole.

7. A compound selected from the group consisting of:
2-cyano-1-[(4-{[3-(dimethylsulfamoyl)benzene]sulfonyl}phenyl)methyl]-3-(pyridin-4-yl)guanidine;
(E)-3-({4-[(3-chlorobenzene)sulfonyl]phenyl}methyl)-2-cyano-1-(pyridin-4-yl)guanidine;
1-[(4-{[4-chloro-3-(trifluoromethyl)benzene]sulfonyl}phenyl)methyl]-2-cyano-3-(pyridin-4-yl)guanidine;
2-cyano-1-[(4-{[3-(ethanesulfonyl)benzene]sulfonyl}phenyl)methyl]-3-(pyridin-4-yl)guanidine;
1-[4-(benzenesulfonyl)phenyl]-2-cyano-3-(pyridin-3-ylmethyl)guanidine;
2-cyano-3-(pyridin-4-yl)-1-[(4-{[3-(trifluoromethoxy)benzene]sulfonyl}phenyl)methyl]guanidine;
2-cyano-3-(pyridin-4-yl)-1-{[4-(quinoline-8-sulfonyl)phenyl]methyl}guanidine;
2-cyano-1-({4-[(3,5-dimethylbenzene)sulfonyl]phenyl}methyl)-3-(pyridin-4-yl)guanidine;
2-cyano-3-(pyridin-4-yl)-1-{[4-(quinoline-6-sulfonyl)phenyl]methyl}guanidine;
2-cyano-1-[(4-{[2-(morpholin-4-ylmethyl)benzene]sulfonyl}phenyl)methyl]-3-(pyridin-4-yl)guanidine;
2-cyano-1-{[4-(2-methylpyridine-3-sulfonyl)phenyl]methyl}-3-(pyridin-4-yl)guanidine;
2-cyano-1-{[4-(6-methylpyridine-3-sulfonyl)phenyl]methyl}-3-(pyridin-4-yl)guanidine;
4-[(4-{[2-cyano-3-(pyridin-4-yl)carbamimidamido]methyl}benzene)sulfonyl]-N-ethylbenzamide;
2-cyano-1-[(4-{[4-(propan-2-yl)benzene]sulfonyl}phenyl)methyl]-3-(pyridin-4-yl)guanidine;
3-({4-[(3-chlorobenzene)sulfonyl]phenyl}methyl)-2-cyano-1-(pyridin-4-yl)guanidine;
2-cyano-1-({4-[(3,4-dimethylbenzene)sulfonyl]phenyl}methyl)-3-(pyridin-4-yl)guanidine;
2-cyano-1-{[4-(1-methyl-1H-pyrazole-4-sulfonyl)phenyl]methyl}-3-(pyridin-4-yl)guanidine;
2-cyano-1-[(4-{[3-(1H-pyrazol-1-yl)benzene]sulfonyl}phenyl)methyl]-3-(pyridin-4-yl)guanidine;
2-cyano-1-[(4-{[3-fluoro-5-(trifluoromethyl)benzene]sulfonyl}phenyl)methyl]-3-(pyridin-4-yl)guanidine;
2-cyano-1-({4-[(4-methanesulfonylbenzene)sulfonyl]phenyl}methyl)-3-(pyridin-4-yl)guanidine;
2-cyano-1-({4-[6-(morpholin-4-yl)pyridine-3-sulfonyl]phenyl}methyl)-3-(pyridin-4-yl)guanidine;
1-({4-[(3-chloro-4-methoxybenzene)sulfonyl]phenyl}methyl)-2-cyano-3-(pyridin-4-yl)guanidine;
2-cyano-1-[(4-{[3-(propan-2-yl)benzene]sulfonyl}phenyl)methyl]-3-(pyridin-4-yl)guanidine;
2-cyano-1-[(4-{[3-fluoro-4-(2,2,2-trifluoroethoxy)benzene]sulfonyl}phenyl)methyl]-3-(pyridin-4-yl)guanidine;
2-cyano-1-[(4-{[4-(propan-2-yloxy)benzene]sulfonyl}phenyl)methyl]-3-(pyridin-4-yl)guanidine;
2-cyano-1-({4-[(3,4-dichlorobenzene)sulfonyl]phenyl}methyl)-3-(pyridin-4-yl)guanidine;
2-cyano-1-({4-[(3-fluorobenzene)sulfonyl]phenyl}methyl)-3-(pyridin-4-yl)guanidine;
2-cyano-1-[(4-{[2-methoxy-4-(trifluoromethyl)benzene]sulfonyl}phenyl)methyl]-3-(pyridin-4-yl)guanidine;
3-[(4-{[2-cyano-3-(pyridin-4-yl)carbamimidamido]methyl}benzene)sulfonyl]-N-cyclopentylbenzamide;
(E)-3-{[4-(benzenesulfonyl)phenyl]methyl}-2-cyano-1-(pyridin-3-ylmethyl)guanidine;
1-{[4-(2H-1,3-benzodioxole-5-sulfonyl)phenyl]methyl}-2-cyano-3-(pyridin-4-yl)guanidine;
2-cyano-1-({4-[(3,5-difluorobenzene)sulfonyl]phenyl}methyl)-3-(pyridin-4-yl)guanidine;

1-({4-[3-chloro-2-(morpholin-4-yl)pyridine-4-sulfonyl]phenyl}methyl)-2-cyano-3-(pyridin-4-yl)guanidine;
3-[(4-{[2-cyano-3-(pyridin-4-yl)carbamimidamido]methyl}benzene)sulfonyl]-N-ethylbenzamide;
2-cyano-1-({4-[(2-methoxybenzene)sulfonyl]phenyl}methyl)-3-(pyridin-4-yl)guanidine;
2-cyano-1-({4-[(3-methoxybenzene)sulfonyl]phenyl}methyl)-3-(pyridin-4-yl)guanidine
2-cyano-1-(imidazo[1,2-a]pyridin-7-ylmethyl)-3-(4-(phenylsulfonyl)benzyl)guanidine;
3-{[4-(benzenesulfonyl)phenyl]methyl}-2-cyano-1-{imidazo[1,2-a]pyridin-7-yl}guanidine;
2-cyano-1-({4-[(3,4-dimethoxybenzene)sulfonyl]phenyl}methyl)-3-(pyridin-4-yl)guanidine;
2-cyano-1-({4-[(3-ethoxybenzene)sulfonyl]phenyl}methyl)-3-(pyridin-4-yl)guanidine;
3-[(4-{[2-cyano-3-(pyridin-4-yl)carbamimidamido]methyl}benzene)sulfonyl]-N,N-diethyl-4-fluorobenzamide;
2-cyano-1-{[4-(4-methylpyridine-3-sulfonyl)phenyl]methyl}-3-(pyridin-4-yl)guanidine;
3-[(4-{[2-cyano-3-(pyridin-4-yl)carbamimidamido]methyl}benzene)sulfonyl]-N,N-dimethylbenzamide;
2-cyano-1-({4-[2-(dimethylamino)pyrimidine-5-sulfonyl]phenyl}methyl)-3-(pyridin-4-yl)guanidine;
2-cyano-1-({4-[(3,5-dichlorobenzene)sulfonyl]phenyl}methyl)-3-(pyridin-4-yl)guanidine;
2-cyano-1-[(4-{[3-(propan-2-yloxy)benzene]sulfonyl}phenyl)methyl]-3-(pyridin-4-yl)guanidine;
2-cyano-1-({4-[(4-fluoro-2-methylbenzene)sulfonyl]phenyl}methyl)-3-(pyridin-4-yl)guanidine;
2-cyano-1-({4-[(2,3-dimethylbenzene)sulfonyl]phenyl}methyl)-3-(pyridin-4-yl)guanidine;
2-cyano-1-{[4-(2, 6-dimethoxypyridine-3-sulfonyl)phenyl]methyl}-3-(pyridin-4-yl)guanidine;
1-({4-[(4-acetylbenzene)sulfonyl]phenyl}methyl)-2-cyano-3-(pyridin-4-yl)guanidine;
2-cyano-1-({4-[(4-ethoxybenzene)sulfonyl]phenyl}methyl)-3-(pyridin-4-yl)guanidine;
2-cyano-3-{[4-(phenylmethane)sulfonylphenyl]methyl}-1-(pyridin-4-yl)guanidine;
2-cyano-1-({4-[(4-cyanobenzene)sulfonyl]phenyl}methyl)-3-(pyridin-4-yl)guanidine;
2-cyano-1-({4-[(2-ethoxybenzene)sulfonyl]phenyl}methyl)-3-(pyridin-4-yl)guanidine;
2-cyano-1-[(4-{[4-(1H-pyrazol-1-yl)benzene]sulfonyl}phenyl)methyl]-3-(pyridin-4-yl)guanidine;
1-({4-[(4-chloro-3-fluorobenzene)sulfonyl]phenyl}methyl)-2-cyano-3-(pyridin-4-yl)guanidine;
2-cyano-3-({4-[(4-fluorobenzene)sulfonyl]phenyl}methyl)-1-(pyridin-4-yl)guanidine;
1-({4-[(3-chloro-5-methylbenzene)sulfonyl]phenyl}methyl)-2-cyano-3-(pyridin-4-yl)guanidine;
3-{[4-(benzenesulfonyl)phenyl]methyl}-2-cyano-1-{imidazo[1,2-a]pyridin-7-ylmethyl}guanidine;
2-cyano-1-({4-[(3-fluoro-5-methoxybenzene)sulfonyl]phenyl}methyl)-3-(pyridin-4-yl)guanidine;
2-cyano-1-{[4-({3-[(morpholin-4-yl)carbonyl]benzene}sulfonyl)phenyl]methyl}-3-(pyridin-4-yl)guanidine;
2-cyano-1-({4-[(4-fluoro-3-methylbenzene)sulfonyl]phenyl}methyl)-3-(pyridin-4-yl)guanidine;
1-({4-[(4-chloro-2-methoxybenzene)sulfonyl]phenyl}methyl)-2-cyano-3-(pyridin-4-yl)guanidine;
1-({4-[(3-chloro-4-methylbenzene)sulfonyl]phenyl}methyl)-2-cyano-3-(pyridin-4-yl)guanidine;
2-cyano-1-({4-[(5-fluoro-2-methylbenzene)sulfonyl]phenyl}methyl)-3-(pyridin-4-yl)guanidine;
1-{[4-(2H-1,3-benzodioxole-4-sulfonyl)phenyl]methyl}-2-cyano-3-(pyridin-4-yl)guanidine;
1-({4-[(5-chloro-2-methoxybenzene)sulfonyl]phenyl}methyl)-2-cyano-3-(pyridin-4-yl)guanidine;
2-cyano-3-(pyridin-4-yl)-1-{[4-({4-[(pyrrolidin-1-yl)carbonyl]benzene}sulfonyl)phenyl]methyl}guanidine;
2-cyano-3-(pyridin-4-yl)-1-[(4-{[4-(trifluoromethyl)benzene]sulfonyl}phenyl)methyl]guanidine;
3-[(4-{[2-cyano-3-(pyridin-4-yl)carbamimidamido]methyl}benzene)sulfonyl]-5-fluoro-N,N-dimethylbenzamide;
2-cyano-1-{[4-(1-propyl-1H-pyrazole-4-sulfonyl)phenyl]methyl}-3-(pyridin-4-yl)guanidine;
2-cyano-3-(pyridin-4-yl)-1-[(4-{[4-(trifluoromethoxy)benzene]sulfonyl}phenyl)methyl]guanidine;
2-cyano-1-({4-[(4-ethylbenzene)sulfonyl]phenyl}methyl)-3-(pyridin-4-yl)guanidine;
2-cyano-1-({4-[(4-methoxy-3-methylbenzene)sulfonyl]phenyl}methyl)-3-(pyridin-4-yl)guanidine;
1-({4-[(3-chloro-4-propoxybenzene)sulfonyl]phenyl}methyl)-2-cyano-3-(pyridin-4-yl)guanidine;
2-cyano-1-{[4-(naphthalene-1-sulfonyl)phenyl]methyl}-3-(pyridin-4-yl)guanidine;
2-cyano-1-({4-[(3-cyanobenzene)sulfonyl]phenyl}methyl)-3-(pyridin-4-yl)guanidine;
2-cyano-1-[(4-{[3-(propane-1-sulfonamido)benzene]sulfonyl}phenyl)methyl]-3-(pyridin-4-yl)guanidine;
5-[(4-{[2-cyano-3-(pyridin-4-yl)carbamimidamido]methyl}benzene)sulfonyl]-N-methylpyridine-2-carboxamide;
3-[(4-{[2-cyano-3-(pyridin-4-yl)carbamimidamido]methyl}benzene)sulfonyl]-N-cyclopropylbenzamide;
1-({4-[(3-chloro-5-methoxybenzene)sulfonyl]phenyl}methyl)-2-cyano-3-(pyridin-4-yl)guanidine;
1-({4-[(4-chlorobenzene)sulfonyl]phenyl}methyl)-2-cyano-3-(pyridin-4-yl)guanidine;
2-cyano-3-(pyridin-4-yl)-1-[(4-{[3-(trifluoromethyl)benzene]sulfonyl}phenyl)methyl]guanidine;
3-{[4-(benzenesulfonyl)phenyl]methyl}-2-cyano-1-(pyridin-3-yl)guanidine;
1-({4-[(3-chloro-5-fluorobenzene)sulfonyl]phenyl}methyl)-2-cyano-3-(pyridin-4-yl)guanidine;
2-cyano-1-({4-[(3,4-difluorobenzene)sulfonyl]phenyl}methyl)-3-(pyridin-4-yl)guanidine;
2-cyano-1-({4-[(3-methylbenzene)sulfonyl]phenyl}methyl)-3-(pyridin-4-yl)guanidine;
2-cyano-1-{[4-(5-methoxypyridine-3-sulfonyl)phenyl]methyl}-3-(pyridin-4-yl)guanidine;
2-cyano-1-[(4-{[3-fluoro-4-(1H-pyrazol-1-yl)benzene]sulfonyl}phenyl)methyl]-3-(pyridin-4-yl)guanidine;
1-{2-[4-(benzenesulfonyl)phenyl]ethyl}-2-cyano-3-(pyridin-4-yl)guanidine;
2-cyano-1-({4-[(3-fluoro-4-methylbenzene)sulfonyl]phenyl}methyl)-3-(pyridin-4-yl)guanidine
2-cyano-3-[(4-{8-oxa-3-azabicyclo[3.2.1]octane-3-sulfonyl}phenyl)methyl]-1-(pyridin-4-yl)guanidine;
2-cyano-1-({4-[(3-fluoro-4-methoxybenzene)sulfonyl]phenyl}methyl)-3-(pyridin-4-yl)guanidine;
2-cyano-1-({4-[(4-phenylbenzene)sulfonyl]phenyl}methyl)-3-(pyridin-4-yl)guanidine;
2-cyano-1-({4-[(3-fluoro-5-methylbenzene)sulfonyl]phenyl}methyl)-3-(pyridin-4-yl)guanidine
2-cyano-1-{[4-(1-methyl-1H-indazole-6-sulfonyl)phenyl]methyl}-3-(pyridin-4-yl)guanidine;

2-cyano-1-({4-[(4-methylbenzene)sulfonyl]phenyl}methyl)-3-(pyridin-4-yl)guanidine;
2-cyano-1-{[4-(5-fluoropyridine-3-sulfonyl)phenyl]methyl}-3-(pyridin-4-yl)guanidine;
2-cyano-1-[(4-{[3-(methoxymethyl)benzene]sulfonyl}phenyl)methyl]-3-(pyridin-4-yl)guanidine;
1-({4-[(5-acetyl-2-methoxybenzene)sulfonyl]phenyl}methyl)-2-cyano-3-(pyridin-4-yl)guanidine;
2-cyano-3-(pyridin-4-yl)-1-{[4-(quinoline-3-sulfonyl)phenyl]methyl}guanidine;
2-cyano-1-({4-[(4-methoxybenzene)sulfonyl]phenyl}methyl)-3-(pyridin-4-yl)guanidine;
3-{[4-(benzenesulfonyl)phenyl]methyl}-2-cyano-1-(pyridin-4-yl)guanidine;
2-cyano-1-{[4-(1-methyl-1H-indole-2-sulfonyl)phenyl]methyl}-3-(pyridin-4-yl)guanidine;
2-cyano-3-(pyridin-4-yl)-1-{[4-(pyridine-3-sulfonyl)phenyl]methyl}guanidine;
2-cyano-1-[(4-{[3-(3,5-dimethyl-1H-pyrazol-1-yl)benzene]sulfonyl}phenyl)methyl]-3-(pyridin-4-yl)guanidine;
3-chloro-5-[(4-{[2-cyano-3-(pyridin-4-yl)carbamimidamido]methyl}benzene)sulfonyl]-N,N-diethylbenzamide;
2-cyano-1-[(4-{[2-methoxy-5-(propan-2-yl)benzene]sulfonyl}phenyl)methyl]-3-(pyridin-4-yl)guanidine;
2-cyano-1-[(4-{[4-(morpholin-4-yl)benzene]sulfonyl}phenyl)methyl]-3-(pyridin-4-yl)guanidine;
2-cyano-1-({4-[(3-methoxy-4-methylbenzene)sulfonyl]phenyl}methyl)-3-(pyridin-4-yl)guanidine;
2-cyano-1-(pyridin-4-yl)-3-[(4-{[2-(trifluoromethoxy)benzene]sulfonyl}phenyl)methyl]guanidine;
2-cyano-1-[(4-{[3-fluoro-5-(2,2,2-trifluoroethoxy)benzene]sulfonyl}phenyl)methyl]-3-(pyridin-4-yl)guanidine;
2-cyano-1-({4-[(4-ethoxy-3-fluorobenzene)sulfonyl]phenyl}methyl)-3-(pyridin-4-yl)guanidine;
3-[(4-{[2-cyano-3-(pyridin-4-yl)carbamimidamido]methyl}benzene)sulfonyl]-N-(propan-2-yl)benzamide;
2-cyano-1-({4-[(2,4-dimethylbenzene)sulfonyl]phenyl}methyl)-3-(pyridin-4-yl)guanidine;
1-[(4-{[3-chloro-5-(trifluoromethyl)benzene]sulfonyl}phenyl)methyl]-2-cyano-3-(pyridin-4-yl)guanidine; and
2-cyano-1-({4-[(2-methylbenzene)sulfonyl]phenyl}methyl)-3-(pyridin-4-yl)guanidine;
and pharmaceutically acceptable salts thereof.

\* \* \* \* \*